US008008012B2

(12) United States Patent
Guyon

(10) Patent No.: US 8,008,012 B2
(45) Date of Patent: Aug. 30, 2011

(54) BIOMARKERS DOWNREGULATED IN PROSTATE CANCER

(75) Inventor: Isabelle Guyon, Berkeley, CA (US)

(73) Assignee: Health Discovery Corporation, Savannah, GA (US)

( * ) Notice: Subject to any disclaimer, the term of this patent is extended or adjusted under 35 U.S.C. 154(b) by 60 days.

(21) Appl. No.: 12/242,912

(22) Filed: Sep. 30, 2008

(65) Prior Publication Data

US 2009/0305257 A1  Dec. 10, 2009

Related U.S. Application Data

(63) Continuation-in-part of application No. 12/025,724, filed on Feb. 4, 2008, which is a continuation-in-part of application No. 11/274,931, filed on Nov. 14, 2005, now abandoned.

(60) Provisional application No. 60/976,791, filed on Oct. 1, 2007, provisional application No. 60/627,626, filed on Nov. 12, 2004, provisional application No. 60/651,340, filed on Feb. 9, 2005, provisional application No. 60/888,070, filed on Feb. 2, 2007.

(51) Int. Cl.
*C12Q 1/68* (2006.01)

(52) U.S. Cl. .......................................................... 435/6

(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. |
| 5,552,277 A | 9/1996 | Nelson et al. |
| 5,837,832 A | 11/1998 | Chee et al. |
| 5,972,615 A | 10/1999 | An et al. |
| 6,107,103 A | 8/2000 | Xuan et al. |
| 6,128,608 A | 10/2000 | Barnhill |
| 6,171,796 B1 | 1/2001 | An et al. |
| 6,395,479 B1 | 5/2002 | Reichardt et al. |
| 6,427,141 B1 | 7/2002 | Barnhill |
| 6,511,806 B1 | 1/2003 | Freuhauf et al. |
| 6,566,130 B1 | 5/2003 | Srivastava et al. |
| 6,685,395 B1 | 2/2004 | Busby |
| 6,692,916 B2 | 2/2004 | Bevilacqua et al. |
| 6,714,925 B1 | 3/2004 | Barnhill et al. |
| 6,760,715 B1 | 7/2004 | Barnhill et al. |
| 6,789,069 B1 | 9/2004 | Barnhill et al. |
| 6,882,990 B1 | 4/2005 | Barnhill et al. |
| 6,949,342 B2 | 9/2005 | Golub et al. |
| 6,960,439 B2 | 11/2005 | Bevilacqua et al. |
| 7,252,935 B2 | 8/2007 | Sidransky |
| 2001/0007748 A1 | 7/2001 | An et al. |
| 2002/0151681 A1 | 10/2002 | Rosen |
| 2002/0168638 A1 | 11/2002 | Schlegel et al. |
| 2003/0049645 A1 | 3/2003 | Mu et al. |
| 2003/0087818 A1 | 5/2003 | Jiang |
| 2003/0108963 A1 | 6/2003 | Schlegel |
| 2003/0113762 A1 | 6/2003 | Warrington |
| 2003/0138793 A1 | 7/2003 | Su et al. |
| 2003/0172043 A1 | 9/2003 | Guyon et al. |
| 2003/0175736 A1 | 9/2003 | Chinnaiyan et al. |
| 2003/0180738 A1 | 9/2003 | Rees et al. |
| 2003/0215835 A1 | 11/2003 | Sun et al. |
| 2004/0009481 A1 | 1/2004 | Schlegel et al. |
| 2004/0029151 A1 | 2/2004 | Mahadevappa et al. |
| 2004/0092469 A1 | 5/2004 | Srivastava et al. |
| 2004/0110221 A1 | 6/2004 | Twine et al. |
| 2004/0121413 A1 | 6/2004 | Aebersold et al. |
| 2004/0133352 A1 | 7/2004 | Bevilacqua et al. |
| 2004/0137455 A1 | 7/2004 | Dong et al. |
| 2004/0175743 A1 | 9/2004 | Burczinski et al. |
| 2004/0203012 A1 | 10/2004 | Diamandis |
| 2004/0225449 A1 | 11/2004 | Bevilacqua et al. |
| 2004/0235071 A1 | 11/2004 | Lightcap et al. |
| 2004/0259086 A1 | 12/2004 | Schlegel et al. |
| 2005/0009771 A1 | 1/2005 | Levanon et al. |
| 2005/0032065 A1 | 2/2005 | Afar et al. |
| 2005/0112134 A1 | 5/2005 | Graddis et al. |
| 2005/0112678 A1 | 5/2005 | Yang |
| 2005/0119210 A1 | 6/2005 | Be et al. |
| 2005/0136493 A1 | 6/2005 | Rubin et al. |
| 2005/0191673 A1 | 9/2005 | Schlegel et al. |
| 2005/0227917 A1 | 10/2005 | Williams |
| 2005/0244843 A1 | 11/2005 | Chen et al. |
| 2005/0244973 A1 | 11/2005 | Andel et al. |
| 2005/0259483 A1 | 11/2005 | Nakamura et al. |
| 2005/0272061 A1 | 12/2005 | Petroziello et al. |
| 2006/0019256 A1 | 1/2006 | Clarke et al. |
| 2006/0134688 A1 | 6/2006 | Welsh |

(Continued)

FOREIGN PATENT DOCUMENTS

WO  0055174  9/2000

(Continued)

OTHER PUBLICATIONS

Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Goessl et al (Cancer Research, 2000, 60(21):5941-5945).*
Aerts, H., "Chitotriosidase—New Biochemical Marker", *Gauchers News*, Mar. 1996.
Albrecht, et al., "Expression, localization and activity of neutral endopeptidase in cultured cells of benign prostatic hyperplasia and prostate cancer", *J Urol.*, Jul. 2002, pp. 336-342, vol. 168(1) (Abstract).
Alizadeh, et al., "Distinct types of diffuse large B-cell lymphoma identified by gene expression profiling", *Nature*, Feb. 3, 2000, vol. 403(6769) (Abstract).
Alon, et al., "Broad patterns of gene expression revealed by clustering analysis of tumor and normal colon cancer tissues probed by oligonucleotide arrays", *PNAS, Cell Biology*, Jun. 1999, pp. 6745-6750, vol. 96.

(Continued)

*Primary Examiner* — Sean Aeder
(74) *Attorney, Agent, or Firm* — Eleanor M. Musick; Procopio, Cory, Hargreaves & Savitch, LLP

(57) ABSTRACT

Biomarkers are identified by analyzing gene expression data using support vector machines (SVM), recursive feature elimination (RFE) and/or linear ridge regression classifiers to rank genes according to their ability to separate prostate cancer from normal tissue. Proteins expressed by identified genes are detected in patient samples to screen, predict and monitor prostate cancer.

6 Claims, 29 Drawing Sheets

U.S. PATENT DOCUMENTS

| | | | |
|---|---|---|---|
| 2006/0211017 | A1 | 9/2006 | Chinnaiyan et al. |
| 2006/0269546 | A1 | 11/2006 | Srivastava et al. |
| 2007/0014801 | A1 | 1/2007 | Gish |
| 2007/0041944 | A1 | 2/2007 | Iavarone |
| 2007/0048738 | A1* | 3/2007 | Donkena et al. ............ 435/6 |
| 2007/0059712 | A1 | 3/2007 | Gish |
| 2007/0065856 | A1 | 3/2007 | Belacel et al. |
| 2007/0099209 | A1 | 5/2007 | Clarke et al. |
| 2007/0105133 | A1 | 5/2007 | Clarke et al. |
| 2007/0212702 | A1 | 9/2007 | Tomlins et al. |
| 2008/0254455 | A1 | 10/2008 | Wang et al. |

FOREIGN PATENT DOCUMENTS

| | | |
|---|---|---|
| WO | 02053223 | 7/2002 |
| WO | 2004090163 | 10/2004 |
| WO | 2005015236 | 2/2005 |

OTHER PUBLICATIONS

Bauer, et al., "Elevated levels of apoptosis regulator proteins p53 and bcl-2 are independent prognostic biomarkers in surgically treated clinically localized prostate cancer", *J Urol.*, Oct. 1996, pp. 1511-1516, vol. 156(4) (Abstract).

Beer, et al., "Polymorphisms of GSTP1 and related genes and prostate cancer risk", *Prostate Cancer Prostatic Dis.*, 2002, pp. 22-27, vol. 5(1) (Abstract).

Borre, et al., "p53 accumulation associated with bcl-2, the proliferation marker MIB-1 and survival in patients with prostate cancer subjected to watchful waiting", *J Urol.*, Sep. 2000, pp. 716-721, vol. 164(3 Pt 1) (Abstract).

Burns-Cox, et al., "Changes in collagen metabolism in prostate cancer: a host response that may alter progression", *J Urol.*, Nov. 2001, pp. 1698-1701, vol. 166(5) (Abstract).

Caine, et al., "Plasma angiopoietin-1, angiopoietin-2 and Tie-2 in breast and prostate cancer: a comparison with VEGF and Flt-1", *Eur J Clin Invest.*, Oct. 2003, pp. 883-890, vol. 33(10) (Abstract).

Depinieux, et al., "Clinical and experimental progression of a new model of human prostate cancer and therapeutic approach", *Am J Pathol.*, Aug. 2001, pp. 753-764, vol. 159(2).

Deprimo, et al., "Transcriptional Programs Activated by Exposure of Human Prostate Cancer Cells to Androgen", *Genome Biology*, 2002, vol. 3(7).

Dhanasekaran, et al., "Delineation of prognostic biomarkers in prostate cancer", *Nature*, Aug. 23, 2001, pp. 822-826, vol. 412(6849) (Abstract).

Ernst, et al., "Decrease and gain of gene expression are equally discriminatory markers for prostate carcinoma: a gene expression analysis on total and microdissected prostate tissue", *Am J Pathol.*, Jun. 2002, pp. 2169-2180, vol. 160(6).

Febbo et al., "Use of expression analysis to predict outcome after radical prostatectomy", *The journal of urology*, Dec. 2003, pp. 811-820, vol. 170.

Floryk, et al., "Differentiation of Human Prostate Cancer PC-3 Cells Induced by Inhibitors of Inosine 5'-Monophosphate Dehydrogenase", *Cancer Research*, Dec. 15, 2004, pp. 9049-9056, vol. 64.

Fujarewicz, et al., "Selecting differentially expressed genes for colon tumor classification", *Int. J. Appl. Math. Comput. Sci.*, 2003, pp. 327-335, vol. 13, No. 3.

Gelmann, et al., "Expression of genes and proteins specific for prostate cancer", *J Urol.*, Nov. 2004, pp. S23-6;, vol. 172(5 Pt 2), discussion S26-7, (Abstract).

Ghigna, et al., "Altered Expression of Heterogeneous Nuclear Ribonucleoproteins and SR Factors in Human", *Cancer Research*, pp. 9212-9217, vol. 58, 5818-5824 (Abstract).

Glinsky, et al., "Gene expression profiling predicts clinical outcome of prostate cancer", *J Clin Invest.*, Mar. 2004. pp. 806-808, vol. 113(6).

Golub, et al., "Molecular Classification of Cancer: Class Discovery and Class Prediction by Gene Expression Monitoring", *Science*, Oct. 15, 1999, pp. 531-537, vol. 286.

Guyon, et al., "Gene Selection for Cancer Classification using Support Vector Machines", *Machine Learning*, 2002, pp. 389-422, vol. 46.

Harden, et al., "Quantitative GSTP1 methylation clearly distinguishes benign prostatic tissue and limited prostate adenocarcinoma", *J Urol.*, 2003, pp. 1138-1142, vol. 169(3) (Abstract).

Karakiulakis, G., "Increased Type IV Collagen-Degrading Activity in Metastases Originating from Primary Tumors of the Human Colon", *Invasion and Metastasis*, 1997, pp. 158-168, vol. 17, No. 3 (Abstract).

Kishino, et al., "Correspondence analysis of genes and tissue types and finding genetic links from microarray data", *Genome Inform Ser Workshop Genome Inform*, 2000, pp. 83-95, vol. 11.

Kramer, et al., "Loss of CD38 correlates with simultaneous up-regulation of human leukocyte antigen-DR in benign prostatic glands, but not in fetal or androgen-ablated glands, and is strongly related to gland atrophy", *BJU International*, Mar. 2003, vol. 91, Issue 4.

Kuefer, et al., "alpha-Methylacyl-CoA racemase: expression levels of this novel cancer biomarker depend on tumor differentiation", *Am J Pathol.*, Sep. 2002, pp. 841-848, vol. 161(3).

Lai, et al., "A statistical method for identifying differential gene-gene co-expression patterns", *Bioinformatics*, vol. 20 issue 17 (Abstract).

Lapointe, et al., "Gene expression profiling identifies clinically relevant subtypes of prostate cancer", *Proc Natl Acad Sci USA*, Jan. 20, 2004, pp. 811-816, vol. 101(3).

Latulippe, et al., "Comprehensive gene expression analysis of prostate cancer reveals distinct transcriptional programs associated with metastatic disease", *Cancer Res.*, Aug. 1 2002, pp. 4499-4506, vol. 62(15).

Liu, et al., "Analysis of prostate cancer by proteomics using tissue specimens", *J Urol.*, Jan. 2005, pp. 73-78, vol. 173(1) (Abstract).

Lodygin, et al., "Induction of the Cdk inhibitor p21 by LY83583 inhibits tumor cell proliferation in a p53-independent manner", *J. Clin. Invest.*, 2002, pp. 1717-1727, vol. 110.

Luo, et al., "Gene expression analysis of prostate cancers", *Mol Carcinog.*, Jan. 2002, pp. 25-35, vol. 33(1) (Abstract).

Luo, et al., "Human prostate cancer and benign prostatic hyperplasia: molecular dissection by gene expression profiling", *Cancer Res.*, Jun. 15, 2001, pp. 4683-4688, vol. 61(12).

Magee, et al., "Expression profiling reveals hepsin overexpression in prostate cancer", *Cancer Res.*, Aug. 1, 2001, pp. 5692-5696, vol. 61(15).

Miyake, et al., "Overexpression of insulin-like growth factor binding protein-5 helps accelerate progression to androgen-independence in the human prostate LNCaP tumor model through activation of phosphatidylinositol 3'-kinase pathway", *Endocrinology*, Jun. 2000, pp. 2257-2265, vol. 141(6).

Mobasheri, et al., "Epithelial Na, K-ATPase expression is down-regulated in canine prostate cancer; a possible consequence of metabolic transformation in the process of prostate malignancy", *Cancer Cell International*, 2003, p. 8, vol. 3.

Nogushi, et al., "An analysis of 148 consecutive transition zone cancers: clinical and histological characteristics", *The journal of urology*, Jun. 2000, pp. 1751-1755, vol. 163 (Abstract).

Oliveira, "Chronic Trypanosoma cruzi infection associated to colon cancer. An experimental study in rats", *Resumo di Tese. Revista da Sociedade Brasileira de Medicina Tropical*, Jan.-Feb. 1999, pp. 81-82, vol. 32(1).

Perou, et al., "Distinctive gene expression patterns in human mammar epithelial cells and breast cancers", *Proc. Natl. Acad. Sci. USA, Genetics*, Aug. 1999, pp. 9212-9217, vol. 96.

Prtilo, et al., "Tissue microarray analysis of hMSH2 expression predicts outcome in men with prostate cancer", *J Urol.*, Nov. 2005, pp. 1814-1818, vol. 174(5) (Abstract).

Ramaswamy, et al., "Multiclass cancer diagnosis using tumor gene expression signatures", *Proc. Natl. Acad. Sci. USA*, Dec. 2001, pp. 15149-15154, vol. 98.

Ramaswamy, et al., "A molecular signature of metastasis in primary solid tumors", *Nat Genet.*, Jan. 2003, pp. 49-54, vol. 33(1).

Reese, et al., "HER2 protein expression and gene amplification in androgen-independent prostate cancer", *Am J Clin Pathol.*, Aug. 2001, pp. 234-239, vol. 116(2) (Abstract).

Rao, et al., "Huntingtin-interacting protein 1 is overexpressed in prostate and colon cancer and is critical for cellular survival", *J Clin Invest.*, Aug. 2002, pp. 351-60, vol. 110(3).

Rubin, et al., "alpha-Methylacyl coenzyme A racemase as a tissue biomarker for prostate cancer", *JAMA*, Apr. 3, 2002, pp. 1662-1670, vol. 287(13) (Abstract).

Savinainen, et al., "Expression and gene copy number analysis of ERBB2 oncogene in prostate cancer", *Am J Pathol.*, Jan. 2002, pp. 339-345, vol. 160(1).

Schölkopf, et al., "Estimating the Support of a High-Dimensional Distribution", Proceeding of *NIPS*, 1999.

Singh, et al., "Gene expression correlates of clinical prostate cancer behavior", *Cancer Cell*, Mar. 1, 2002, pp. 203-209, vol. 2.

Stamey, et al., "Biological determinants of cancer progression in men with prostate cancer", *J. Amer. Med. Assoc.*, 1999, pp. 1395-4000, vol. 281.

Stamey, et al., "Genetic profiling of Gleason grade 4/5 prostate cancer: which is the best prostatic control?", *J. Urol*, 2003, p. 2263, vol. 170 (Abstract).

Stamey, et al., "Molecular genetic profiling of Gleason grade 4/5 cancers compared to benign prostate hyperplasia", *J. Urol.* 2001, p. 2171, vol. 166 (Abstract).

Steiner, et al., "Gene therapy for prostate cancer: where are we now?", *J Urol.*, Oct. 2000, pp. 1121-1136, vol. 164(4) (Abstract).

Stephan, et al., "Hepsin is highly over expressed in and a new candidate for a prognostic indicator in prostate cancer", *J Urol.*, Jan. 2004, pp. 187-191, vol. 171(1) (Abstract).

Stephan, et al., "Quantitative analysis of kallikrein 15 gene expression in prostate tissue", *J Urol.*, Jan. 2003, pp. 361-364, vol. 169(1), (Abstract).

Su, et al., "Molecular classification of human carcinomas by use of gene expression signatures", *Cancer Res.*, Oct. 15, 2001, pp. 7388-7393, vol. 61(20).

Thorsteinsdottir, et al., "The oncoprotein E2A-Pbx1a collaborates with Hoxa9 to acutely transform primary bone marrow cells", *Molecular Cell Biology*, Sep. 1999, pp. 6355-6366, vol. 19, Issue 9.

Tibshirani, et al., "Diagnosis of multiple cancer types by shrunken centroids of gene expression", *PNAS*, May 14, 2002, pp. 6567-6572, vol. 99.

Tokugawa, et al., "Lipocalin-type prostaglandin D synthase in human male reproductive organs and seminal plasma", *Biology of Reproduction*, 1998, pp. 600-607, vol. 58.

Tsui, et al., "Down-regulation of the prostate specific antigen promoter by p53 in human prostate cancer cells", *J Urol.*, Nov. 2004, pp. 2035-2039, vol. 172(5 Pt 1) (Abstract).

Verma, et al., "Proteomic analysis of cancer-cell mitochondria", *Nature Reviews Cancer*, 2003, pp. 789-795, vol. 3 (Abstract).

Welsh, et al., "Analysis of gene expression identifies candidate markers and pharmacological targets in prostate cancer", *Cancer Res.*, Aug. 15, 2001, pp. 5974-5978, vol. 61(16).

Yap, et al., "Classification between normal and tumor tissues based on the pair-wise gene expression ratio", *BMC Cancer*, 2004, p. 72, vol. 4.

Yu, et al., "Modulation of prostate carcinoma cell growth and apoptosis by chromogranin A", *J Urol.*, Nov. 2003, pp. 2031-2035, vol. 170(5) (Abstract).

Bhaskar et al., "E-selectin up-regulation allows for targeted drug delivery in prostate cancer", Cancer Research, Oct. 2003, 63:6387-6394.

Bhandari, et al., "Prostate cancer therapeutic target identification via meta analysis of prostate cancer microarray data using ONCOMINE", 2005 Prostate Cancer Symposium, American Society of Clinical Oncology, Abstract No. 195.

Rhodes, et al., Oncomine 3.0: Genes, Pathways, and Networks in a Collection of 18,000 Cancer Gene Expression Profiles, Neoplasia, 2007, 9(2):166-180.

\* cited by examiner

| Rank | Gene ID | Unigene ID | Under Expr. In tumor | AUC | Pval | FDR | Ave. rank |
|---|---|---|---|---|---|---|---|
| 1 | 9459 | Hs.128749 | -1 | 0.9458 | 0.02 | 0.025 | 1.16 |
| 2 | 9458 | Hs.128749 | -1 | 0.9425 | 0.02 | 0.012 | 2.48 |
| 3 | 9457 | Hs.128749 | -1 | 0.9423 | 0.02 | 0.0083 | 2.51 |
| 4 | 11911 | Hs.279009 | 1 | 0.9253 | 0.02 | 0.0062 | 4.31 |
| 5 | 12337 | Hs.7780 | -1 | 0.9125 | 0.02 | 0.005 | 7.23 |
| 6 | 983 | Hs.226795 | 1 | 0.9076 | 0.02 | 0.0042 | 8.42 |
| 7 | 18792 | Hs.6823 | -1 | 0.9047 | 0.02 | 0.0036 | 10.04 |
| 8 | 1908 | Hs.692 | -1 | 0.9044 | 0.02 | 0.0031 | 10.03 |
| 9 | 19589 | Hs.45140 | 1 | 0.9033 | 0.02 | 0.0028 | 10.47 |
| 10 | 6519 | Hs.243960 | 1 | 0.8996 | 0.02 | 0.0025 | 12.67 |
| 11 | 17714 | Hs.5216 | -1 | 0.8985 | 0.02 | 0.0023 | 13.93 |
| 12 | 18122 | Hs.106747 | 1 | 0.8985 | 0.02 | 0.0021 | 13.86 |
| 13 | 18237 | Hs.283719 | 1 | 0.8961 | 0.02 | 0.0019 | 16.61 |
| 14 | 3059 | Hs.771 | 1 | 0.8942 | 0.02 | 0.0018 | 17.86 |
| 15 | 16533 | Hs.110826 | -1 | 0.8921 | 0.02 | 0.0017 | 19.44 |
| 16 | 18598 | Hs.9728 | 1 | 0.8904 | 0.02 | 0.0016 | 19.43 |
| 17 | 12434 | Hs.250723 | 1 | 0.8899 | 0.02 | 0.0015 | 20.19 |
| 18 | 4922 | Hs.55279 | 1 | 0.884 | 0.02 | 0.0014 | 27.23 |
| 19 | 13862 | Hs.66744 | -1 | 0.8832 | 0.02 | 0.0013 | 30.59 |
| 20 | 9976 | Hs.103665 | 1 | 0.8824 | 0.02 | 0.0012 | 30.49 |
| 21 | 18835 | Hs.44278 | -1 | 0.8824 | 0.02 | 0.0012 | 30.94 |
| 22 | 3331 | Hs.54697 | 1 | 0.8802 | 0.02 | 0.0011 | 32.35 |
| 23 | 18969 | Hs.20814 | -1 | 0.8797 | 0.02 | 0.0011 | 35.89 |
| 24 | 9373 | Hs.21293 | -1 | 0.8786 | 0.02 | 0.001 | 35.52 |
| 25 | 15294 | Hs.288649 | -1 | 0.8786 | 0.02 | 0.001 | 35.69 |
| 26 | 4497 | Hs.33084 | 1 | 0.8776 | 0.02 | 0.00096 | 37.77 |
| 27 | 5001 | Hs.823 | -1 | 0.8765 | 0.02 | 0.00093 | 40.25 |
| 28 | 9765 | Hs.22599 | 1 | 0.8765 | 0.02 | 0.00089 | 39.32 |
| 29 | 4479 | Hs.198760 | 1 | 0.8759 | 0.02 | 0.00086 | 40.82 |
| 30 | 239 | Hs.198760 | 1 | 0.8749 | 0.02 | 0.00083 | 43.04 |
| 31 | 6666 | Hs.90911 | 1 | 0.8749 | 0.02 | 0.00081 | 42.53 |
| 32 | 12655 | Hs.10587 | 1 | 0.8749 | 0.02 | 0.00078 | 41.56 |
| 33 | 19264 | Hs.31608 | -1 | 0.8743 | 0.02 | 0.00076 | 44.66 |
| 34 | 5923 | Hs.171731 | 1 | 0.8738 | 0.02 | 0.00074 | 44.3 |
| 35 | 1889 | Hs.195850 | 1 | 0.8727 | 0.02 | 0.00071 | 46.1 |
| 36 | 21568 | Hs.111676 | 1 | 0.8716 | 0.02 | 0.00069 | 48.3 |
| 37 | 3264 | Hs.139336 | -1 | 0.8714 | 0.02 | 0.00068 | 51.17 |
| 38 | 14738 | Hs.8198 | 1 | 0.8706 | 0.02 | 0.00066 | 52.7 |
| 39 | 1867 | Hs.234680 | 1 | 0.8695 | 0.02 | 0.00064 | 52.99 |
| 40 | 4467 | Hs.24587 | 1 | 0.8695 | 0.02 | 0.00062 | 52.25 |
| 41 | 9614 | Hs.8583 | 1 | 0.8695 | 0.02 | 0.00061 | 53.62 |
| 42 | 18659 | Hs.73625 | -1 | 0.8692 | 0.02 | 0.0006 | 56.86 |
| 43 | 20137 | Hs.249727 | 1 | 0.8692 | 0.02 | 0.00058 | 55.2 |
| 44 | 12023 | Hs.74034 | 1 | 0.869 | 0.02 | 0.00057 | 55.69 |
| 45 | 12435 | Hs.82432 | 1 | 0.869 | 0.02 | 0.00056 | 56.63 |
| 46 | 14626 | Hs.23960 | -1 | 0.8687 | 0.02 | 0.00054 | 58.95 |
| 47 | 7082 | Hs.95197 | 1 | 0.8684 | 0.02 | 0.00053 | 56.27 |
| 48 | 15022 | Hs.110826 | -1 | 0.8679 | 0.02 | 0.00052 | 59.51 |
| 49 | 20922 | Hs.0 | -1 | 0.8679 | 0.02 | 0.00051 | 59.93 |

FIG. 4a

| Rank | Gene ID | Unigene ID | Under Expr. In tumor | AUC | Pval | FDR | Ave. rank |
|---|---|---|---|---|---|---|---|
| 50 | 4361 | Hs.102 | 1 | 0.8673 | 0.02 | 0.0005 | 60.94 |
| 51 | 18392 | Hs.1227 | 1 | 0.8671 | 0.02 | 0.00049 | 59.16 |
| 52 | 5199 | Hs.118127 | 1 | 0.8657 | 0.02 | 0.00048 | 62.89 |
| 53 | 4781 | Hs.30054 | -1 | 0.8652 | 0.02 | 0.00047 | 66.67 |
| 54 | 19167 | Hs.9238 | 1 | 0.8652 | 0.02 | 0.00046 | 67.82 |
| 55 | 19573 | Hs.232165 | 1 | 0.8652 | 0.02 | 0.00045 | 66.61 |
| 56 | 4524 | Hs.65029 | 1 | 0.8641 | 0.02 | 0.00045 | 68.12 |
| 57 | 21444 | Hs.262958 | 1 | 0.8641 | 0.02 | 0.00044 | 68.16 |
| 58 | 13307 | Hs.7000 | 1 | 0.8639 | 0.02 | 0.00043 | 69.32 |
| 59 | 17019 | Hs.128749 | -1 | 0.8639 | 0.02 | 0.00042 | 70.9 |
| 60 | 3699 | Hs.242407 | 1 | 0.8636 | 0.02 | 0.00042 | 68.07 |
| 61 | 14522 | Hs.285508 | 1 | 0.8636 | 0.02 | 0.00041 | 69.6 |
| 62 | 1190 | Hs.90061 | 1 | 0.8631 | 0.02 | 0.0004 | 69.94 |
| 63 | 876 | Hs.79037 | -1 | 0.8625 | 0.02 | 0.0004 | 70.66 |
| 64 | 1051 | Hs.118796 | 1 | 0.862 | 0.02 | 0.00039 | 73.7 |
| 65 | 5040 | Hs.2679 | -1 | 0.8617 | 0.02 | 0.00038 | 75.75 |
| 66 | 7460 | Hs.158309 | 1 | 0.8617 | 0.02 | 0.00038 | 76.42 |
| 67 | 4860 | Hs.113082 | 1 | 0.8614 | 0.02 | 0.00037 | 75.84 |
| 68 | 12042 | Hs.142653 | -1 | 0.8612 | 0.02 | 0.00037 | 75.69 |
| 69 | 12046 | Hs.166982 | 1 | 0.8609 | 0.02 | 0.00036 | 80.61 |
| 70 | 10874 | Hs.24587 | 1 | 0.8604 | 0.02 | 0.00036 | 80.34 |
| 71 | 1500 | Hs.74566 | 1 | 0.8598 | 0.02 | 0.00035 | 79.91 |
| 72 | 7822 | Hs.288771 | 1 | 0.8598 | 0.02 | 0.00035 | 81.65 |
| 73 | 8824 | Hs.29759 | 1 | 0.8598 | 0.02 | 0.00034 | 78.78 |
| 74 | 5022 | Hs.15154 | 1 | 0.8593 | 0.02 | 0.00034 | 81.05 |
| 75 | 19501 | Hs.272813 | 1 | 0.8593 | 0.02 | 0.00033 | 82.64 |
| 76 | 1959 | Hs.75319 | -1 | 0.8585 | 0.02 | 0.00033 | 86.9 |
| 77 | 2573 | Hs.82237 | 1 | 0.8577 | 0.02 | 0.00032 | 85.87 |
| 78 | 5150 | Hs.174151 | 1 | 0.8571 | 0.02 | 0.00032 | 89.59 |
| 79 | 5894 | Hs.80247 | 1 | 0.8566 | 0.02 | 0.00032 | 90.53 |
| 80 | 6665 | Hs.90911 | 1 | 0.8563 | 0.02 | 0.00031 | 93.17 |
| 81 | 12572 | Hs.9651 | 1 | 0.8561 | 0.02 | 0.00031 | 93.92 |
| 82 | 6924 | Hs.820 | -1 | 0.8555 | 0.02 | 0.0003 | 94.63 |
| 83 | 1919 | Hs.82422 | 1 | 0.8555 | 0.02 | 0.0003 | 95.13 |
| 84 | 3705 | Hs.278581 | 1 | 0.8555 | 0.02 | 0.0003 | 94.75 |
| 85 | 6131 | Hs.10755 | 1 | 0.8555 | 0.02 | 0.00029 | 93.85 |
| 86 | 11248 | Hs.17481 | 1 | 0.855 | 0.02 | 0.00029 | 97.22 |
| 87 | 17884 | Hs.284243 | -1 | 0.8545 | 0.02 | 0.00029 | 96.85 |
| 88 | 9813 | Hs.18858 | -1 | 0.8542 | 0.02 | 0.00028 | 99.37 |
| 89 | 9336 | Hs.3128 | -1 | 0.8539 | 0.02 | 0.00028 | 99.26 |
| 90 | 19488 | Hs.17752 | -1 | 0.8539 | 0.02 | 0.00028 | 103.94 |
| 91 | 21484 | Hs.28777 | -1 | 0.8539 | 0.02 | 0.00027 | 101.18 |
| 92 | 2624 | Hs.211582 | 1 | 0.8534 | 0.02 | 0.00027 | 100.15 |
| 93 | 5038 | Hs.2621 | 1 | 0.8534 | 0.02 | 0.00027 | 102.73 |
| 94 | 12168 | Hs.75318 | 1 | 0.8528 | 0.02 | 0.00027 | 103.59 |
| 95 | 3425 | Hs.77256 | -1 | 0.8518 | 0.02 | 0.00026 | 107.11 |
| 96 | 5712 | Hs.80667 | -1 | 0.8518 | 0.02 | 0.00026 | 107.92 |
| 97 | 9889 | Hs.137569 | 1 | 0.8518 | 0.02 | 0.00026 | 108.05 |
| 98 | 9851 | Hs.75939 | -1 | 0.8515 | 0.02 | 0.00026 | 110.7 |
| 99 | 1646 | Hs.118638 | -1 | 0.8512 | 0.02 | 0.00025 | 108.38 |

FIG. 4b

| Rank | Gene ID | Unigene ID | Under Expr. In tumor | AUC | Pval | FDR | Ave. rank |
|---|---|---|---|---|---|---|---|
| 100 | 18630 | Hs.104859 | -1 | 0.8507 | 0.02 | 0.00025 | 111.66 |
| 101 | 19422 | Hs.296178 | -1 | 0.8507 | 0.02 | 0.00025 | 112.71 |
| 102 | 979 | Hs.1708 | -1 | 0.8502 | 0.02 | 0.00025 | 111.48 |
| 103 | 2300 | Hs.69469 | -1 | 0.8502 | 0.02 | 0.00024 | 113.24 |
| 104 | 13066 | Hs.12520 | -1 | 0.8502 | 0.02 | 0.00024 | 114.1 |
| 105 | 19840 | Hs.58561 | 1 | 0.8496 | 0.02 | 0.00024 | 116.23 |
| 106 | 13510 | Hs.90911 | 1 | 0.8488 | 0.02 | 0.00024 | 118.16 |
| 107 | 1127 | Hs.9615 | 1 | 0.8485 | 0.02 | 0.00023 | 117.57 |
| 108 | 14690 | Hs.110826 | -1 | 0.848 | 0.02 | 0.00023 | 121.93 |
| 109 | 9499 | Hs.44 | 1 | 0.8475 | 0.02 | 0.00023 | 124.73 |
| 110 | 11793 | Hs.234680 | 1 | 0.8464 | 0.02 | 0.00023 | 127.61 |
| 111 | 12113 | Hs.8272 | 1 | 0.8464 | 0.02 | 0.00023 | 127.01 |
| 112 | 17891 | Hs.8858 | -1 | 0.8464 | 0.02 | 0.00022 | 128 |
| 113 | 22021 | Hs.240845 | -1 | 0.8464 | 0.02 | 0.00022 | 129.22 |
| 114 | 17944 | Hs.279905 | -1 | 0.8459 | 0.02 | 0.00022 | 129.62 |
| 115 | 3310 | Hs.154103 | -1 | 0.8456 | 0.02 | 0.00022 | 129.99 |
| 116 | 12809 | Hs.169401 | -1 | 0.8456 | 0.02 | 0.00022 | 133.01 |
| 117 | 9304 | Hs.75517 | 1 | 0.8453 | 0.02 | 0.00021 | 130.63 |
| 118 | 2123 | Hs.159608 | 1 | 0.8448 | 0.02 | 0.00021 | 136.05 |
| 119 | 21442 | Hs.71819 | -1 | 0.8448 | 0.02 | 0.00021 | 138.01 |
| 120 | 4523 | Hs.65029 | 1 | 0.8445 | 0.02 | 0.00021 | 135.36 |
| 121 | 1690 | Hs.76307 | 1 | 0.8443 | 0.02 | 0.00021 | 135.4 |
| 122 | 3652 | Hs.16622 | 1 | 0.8443 | 0.02 | 0.0002 | 133.49 |
| 123 | 4801 | Hs.80342 | 1 | 0.8443 | 0.02 | 0.0002 | 135.8 |
| 124 | 11607 | Hs.0 | 1 | 0.8437 | 0.02 | 0.0002 | 137.48 |
| 125 | 5149 | Hs.174151 | 1 | 0.8432 | 0.02 | 0.0002 | 140.08 |
| 126 | 966 | Hs.194431 | 1 | 0.8426 | 0.02 | 0.0002 | 140.95 |
| 127 | 9180 | Hs.239926 | 1 | 0.8426 | 0.02 | 0.0002 | 142.19 |
| 128 | 9317 | Hs.1940 | 1 | 0.8426 | 0.02 | 0.0002 | 141.86 |
| 129 | 12605 | Hs.100623 | -1 | 0.8426 | 0.02 | 0.00019 | 144.57 |
| 130 | 21482 | Hs.301732 | -1 | 0.8426 | 0.02 | 0.00019 | 143.39 |
| 131 | 724 | Hs.177656 | 1 | 0.8421 | 0.02 | 0.00019 | 144.91 |
| 132 | 4018 | Hs.21223 | 1 | 0.8421 | 0.02 | 0.00019 | 144.14 |
| 133 | 3390 | Hs.139851 | 1 | 0.8416 | 0.02 | 0.00019 | 148.37 |
| 134 | 7327 | Hs.2388 | -1 | 0.8416 | 0.02 | 0.00019 | 148.06 |
| 135 | 13911 | Hs.408 | 1 | 0.8413 | 0.02 | 0.00019 | 146.81 |
| 136 | 4351 | Hs.303090 | 1 | 0.841 | 0.02 | 0.00018 | 149.01 |
| 137 | 11912 | Hs.279009 | 1 | 0.841 | 0.02 | 0.00018 | 149.29 |
| 138 | 18968 | Hs.207443 | 1 | 0.841 | 0.02 | 0.00018 | 150.77 |
| 139 | 1082 | Hs.117950 | -1 | 0.8405 | 0.02 | 0.00018 | 148.4 |
| 140 | 1961 | Hs.75432 | -1 | 0.8405 | 0.02 | 0.00018 | 153.15 |
| 141 | 2217 | Hs.79217 | -1 | 0.8405 | 0.02 | 0.00018 | 151.68 |
| 142 | 1935 | Hs.75772 | 1 | 0.8402 | 0.02 | 0.00018 | 154.34 |
| 143 | 1912 | Hs.76224 | 1 | 0.84 | 0.02 | 0.00017 | 153.7 |
| 144 | 2343 | Hs.78045 | 1 | 0.84 | 0.02 | 0.00017 | 152.02 |
| 145 | 4754 | Hs.105460 | 1 | 0.84 | 0.02 | 0.00017 | 152.61 |
| 146 | 5832 | Hs.104117 | 1 | 0.84 | 0.02 | 0.00017 | 154.17 |
| 147 | 9325 | Hs.34853 | 1 | 0.84 | 0.02 | 0.00017 | 153.72 |
| 148 | 13843 | Hs.154145 | 1 | 0.84 | 0.02 | 0.00017 | 154.54 |
| 149 | 4386 | Hs.82280 | -1 | 0.8394 | 0.02 | 0.00017 | 155.7 |
| 150 | 10974 | Hs.77899 | 1 | 0.8394 | 0.02 | 0.00017 | 153.76 |

FIG. 4c

| Rank | Gene ID | Unigene ID | Under Expr. In tumor | AUC | Pval | FDR | Ave. rank |
|---|---|---|---|---|---|---|---|
| 151 | 11688 | Hs.0 | 1 | 0.8394 | 0.02 | 0.00017 | 156.4 |
| 152 | 1036 | Hs.699 | -1 | 0.8389 | 0.02 | 0.00016 | 158.14 |
| 153 | 2291 | Hs.279604 | 1 | 0.8389 | 0.02 | 0.00016 | 155.21 |
| 154 | 15260 | Hs.25648 | 1 | 0.8386 | 0.02 | 0.00016 | 157.48 |
| 155 | 1405 | Hs.66708 | 1 | 0.8373 | 0.02 | 0.00016 | 165.04 |
| 156 | 3978 | Hs.75151 | -1 | 0.8373 | 0.02 | 0.00016 | 167.79 |
| 157 | 8821 | Hs.121849 | 1 | 0.8362 | 0.02 | 0.00016 | 169.79 |
| 158 | 8999 | Hs.132898 | 1 | 0.8362 | 0.02 | 0.00016 | 167.99 |
| 159 | 18579 | Hs.283404 | 1 | 0.8359 | 0.02 | 0.00016 | 169.99 |
| 160 | 21798 | Hs.135150 | 1 | 0.8354 | 0.02 | 0.00016 | 176.72 |
| 161 | 4802 | Hs.89901 | 1 | 0.8351 | 0.02 | 0.00016 | 172.85 |
| 162 | 7542 | Hs.283312 | 1 | 0.8351 | 0.02 | 0.00015 | 178.51 |
| 163 | 11677 | Hs.0 | 1 | 0.8351 | 0.02 | 0.00015 | 174.71 |
| 164 | 22117 | Hs.109274 | 1 | 0.8351 | 0.02 | 0.00015 | 176.32 |
| 165 | 308 | Hs.76307 | 1 | 0.8346 | 0.02 | 0.00015 | 175.35 |
| 166 | 1410 | Hs.104925 | -1 | 0.8346 | 0.02 | 0.00015 | 177.73 |
| 167 | 6568 | Hs.89584 | -1 | 0.8346 | 0.02 | 0.00015 | 176.11 |
| 168 | 3363 | Hs.34114 | 1 | 0.834 | 0.02 | 0.00015 | 178.85 |
| 169 | 14542 | Hs.159309 | 1 | 0.8335 | 0.02 | 0.00015 | 183.16 |
| 170 | 9791 | Hs.82223 | 1 | 0.833 | 0.02 | 0.00015 | 182.87 |
| 171 | 18786 | Hs.33085 | -1 | 0.833 | 0.02 | 0.00015 | 184.64 |
| 172 | 6722 | Hs.284203 | -1 | 0.8327 | 0.02 | 0.00015 | 184.85 |
| 173 | 3638 | Hs.74120 | 1 | 0.8324 | 0.02 | 0.00014 | 186.98 |
| 174 | 4109 | Hs.82318 | -1 | 0.8324 | 0.02 | 0.00014 | 188.63 |
| 175 | 14497 | Hs.13804 | 1 | 0.8324 | 0.02 | 0.00014 | 186.08 |
| 176 | 9860 | Hs.158304 | 1 | 0.8319 | 0.02 | 0.00014 | 190.19 |
| 177 | 12838 | Hs.152151 | 1 | 0.8319 | 0.02 | 0.00014 | 189.73 |
| 178 | 4268 | Hs.211595 | -1 | 0.8316 | 0.02 | 0.00014 | 192.31 |
| 179 | 5572 | Hs.159642 | -1 | 0.8314 | 0.02 | 0.00014 | 194.58 |
| 180 | 9467 | Hs.311 | -1 | 0.8311 | 0.02 | 0.00014 | 194.53 |
| 181 | 4779 | Hs.284122 | 1 | 0.8303 | 0.02 | 0.00014 | 197.06 |
| 182 | 374 | Hs.234642 | 1 | 0.8298 | 0.02 | 0.00014 | 198.85 |
| 183 | 3134 | Hs.323469 | 1 | 0.8298 | 0.02 | 0.00014 | 200.94 |
| 184 | 3391 | Hs.139851 | 1 | 0.8292 | 0.02 | 0.00014 | 202.25 |
| 185 | 3822 | Hs.36708 | -1 | 0.8292 | 0.02 | 0.00014 | 200.4 |
| 186 | 3999 | Hs.1162 | -1 | 0.8292 | 0.02 | 0.00013 | 201.46 |
| 187 | 5924 | Hs.1813 | 1 | 0.8292 | 0.02 | 0.00013 | 201.77 |
| 188 | 19025 | Hs.24743 | -1 | 0.8292 | 0.02 | 0.00013 | 203.7 |
| 189 | 12811 | Hs.209100 | 1 | 0.8289 | 0.02 | 0.00013 | 203.54 |
| 190 | 9326 | Hs.34853 | 1 | 0.8287 | 0.02 | 0.00013 | 207.16 |
| 191 | 14516 | Hs.162209 | -1 | 0.8284 | 0.02 | 0.00013 | 206.26 |
| 192 | 167 | Hs.7101 | -1 | 0.8276 | 0.02 | 0.00013 | 209.05 |
| 193 | 231 | Hs.184510 | 1 | 0.8276 | 0.02 | 0.00013 | 209 |
| 194 | 9903 | Hs.63236 | 1 | 0.8273 | 0.02 | 0.00013 | 216.07 |
| 195 | 18867 | Hs.9029 | 1 | 0.8268 | 0.02 | 0.00013 | 216.86 |
| 196 | 9401 | Hs.113 | 1 | 0.8265 | 0.02 | 0.00013 | 216.66 |
| 197 | 14166 | Hs.278503 | 1 | 0.8265 | 0.02 | 0.00013 | 220.19 |
| 198 | 1830 | Hs.154672 | -1 | 0.826 | 0.02 | 0.00013 | 216.11 |
| 199 | 2623 | Hs.2006 | 1 | 0.826 | 0.02 | 0.00013 | 220.9 |
| 200 | 5676 | Hs.2463 | 1 | 0.8255 | 0.02 | 0.00012 | 225.42 |

FIG. 4d

G4 Tumor vs. Others Table Legend:
Rkn=rank in study n; OE=+1 if overexpressed in tumor, -1 otherwise; Score n=AUC score in study n; Pvaln=Bonferroni corrected value in study n; FRDn=False discovery rate in study n.

2001 Study

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 1 | Hs.171731 | -1 | 0.9495 | 0.025 | 0.025 | 3 | 0.8754 | 0.025 | 0.0083 | Human RACH1 (RACH1) mRNA |
| 2 | Hs.3128 | -1 | 0.9081 | 0.025 | 0.012 | 15 | 0.841 | 0.025 | 0.0017 | Human RNA polymerase II subunit (hsRPB8) mRNA |
| 3 | Hs.2025 | -1 | 0.9027 | 0.025 | 0.0083 | 73 | 0.7744 | 0.025 | 0.00034 | Human transforming growth factor-beta 3 (TGF-beta3) mRNA |
| 4 | Hs.174151 | -1 | 0.8892 | 0.025 | 0.0062 | 10 | 0.8448 | 0.025 | 0.0025 | Human aldehyde oxidase (hAOX) mRNA |
| 5 | Hs.34853 | -1 | 0.8892 | 0.025 | 0.005 | 20 | 0.8314 | 0.025 | 0.0012 | Human Id-related helix-loop-helix protein 1d4 mRNA |
| 6 | Hs.155585 | -1 | 0.8838 | 0.025 | 0.0042 | 94 | 0.7626 | 0.025 | 0.00027 | Human transmembrane receptor (ror2) mRNA |
| 7 | Hs.195850 | -1 | 0.8811 | 0.025 | 0.0036 | 2 | 0.8813 | 0.025 | 0.012 | Human keratin type 11(58 kD)mRNA |
| 8 | Hs.65029 | -1 | 0.8802 | 0.025 | 0.0031 | 5 | 0.8647 | 0.025 | 0.005 | Human gas1 gene |
| 9 | Hs.172323 | -1 | 0.8766 | 0.025 | 0.0028 | 2260 | 0.5048 | 1 | 0.97 | Human fetal liver cytochrome P-450 (P450 HFLa) |
| 10 | Hs.85302 | -1 | 0.873 | 0.025 | 0.0025 | 268 | 0.689 | 1 | 0.022 | Human dsRNA adenosine deaminase DRADA2b (DRADA2b) mRNA |
| 11 | Hs.27311 | 1 | 0.8694 | 0.025 | 0.0023 | 42 | 0.8056 | 0.025 | 0.0006 | Human transcription factor SIM2 long form mRNA |
| 12 | Hs.44 | -1 | 0.8685 | 0.025 | 0.0021 | 14 | 0.841 | 0.025 | 0.0018 | Human nerve growth factor (HBNF-1)mRNA |
| 13 | Hs.113 | -1 | 0.8658 | 0.025 | 0.0019 | 24 | 0.8217 | 0.025 | 0.001 | Human cytosolic epoxide hydrolase mRNA |
| 14 | Hs.77546 | -1 | 0.8649 | 0.025 | 0.0018 | 46 | 0.8008 | 0.025 | 0.00054 | Human mRNA for KIAA0172 gene |
| 15 | Hs.771 | -1 | 0.8532 | 0.025 | 0.0017 | 1 | 0.8953 | 0.025 | 0.025 | Human liver glycogen phosphorylase mRNA |
| 16 | Hs.79217 | 1 | 0.8532 | 0.025 | 0.0016 | 7 | 0.855 | 0.025 | 0.0036 | Human pyrroline 5-carboxylate reductase mRNA |
| 17 | Hs.10526 | -1 | 0.8532 | 0.025 | 0.0015 | 105 | 0.7556 | 0.075 | 0.00071 | Human smooth muscl LIM protein (h-SmLIM)mRNA |
| 18 | Hs.620 | -1 | 0.8523 | 0.025 | 0.0014 | 115 | 0.7497 | 0.075 | 0.00065 | Human bullous pemphigoid antigen (BPAG1) mRNA |
| 19 | Hs.198760 | -1 | 0.8495 | 0.025 | 0.0013 | 4 | 0.869 | 0.025 | 0.0062 | H.sapiens NF-H gene |
| 20 | Hs.85146 | -1 | 0.8459 | 0.025 | 0.0012 | 103 | 0.7552 | 0.075 | 0.00073 | Human erythroblastosis virus oncogene homolog 2 (ets-2) mRNA |
| 21 | Hs.75111 | -1 | 0.8432 | 0.025 | 0.0012 | 85 | 0.7669 | 0.025 | 0.00028 | Human cancellous bone osteoblast mRNA for serin protease with IG |
| 22 | Hs.33084 | -1 | 0.8432 | 0.025 | 0.0011 | 151 | 0.7304 | 0.38 | 0.0025 | Human glucose transport-likes (GLUT5) mRNA |
| 23 | Hs.78909 | -1 | 0.8423 | 0.025 | 0.0011 | 234 | 0.7009 | 1 | 0.011 | Human Tis11d gene |

FIG. 5a

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 24 | Hs.2785 | -1 | 0.8414 | 0.025 | 0.001 | 51 | 0.7911 | 0.025 | 0.00049 | H.sapiens gene for cytokeratin 17 |
| 25 | Hs.77840 | -1 | 0.8378 | 0.025 | 0.001 | 446 | 0.6498 | 1 | 0.086 | Human annexin IV (ANX4) mRNA |
| 26 | Hs.74566 | -1 | 0.8369 | 0.025 | 0.00096 | 125 | 0.7433 | 0.1 | 0.0008 | Human mRNA for dihydropyrimidinase related protein-3 |
| 27 | Hs.1869 | -1 | 0.836 | 0.025 | 0.00093 | 284 | 0.6821 | 1 | 0.028 | Human phosphogluconutase 1 (PGM1) mRNA |
| 28 | Hs.76224 | -1 | 0.836 | 0.025 | 0.00089 | 39 | 0.8083 | 0.025 | 0.00064 | Human extracellular protein (S1-5) mRNA |
| 29 | Hs.76688 | -1 | 0.8342 | 0.025 | 0.00086 | 325 | 0.6735 | 1 | 0.038 | Human carboxylesterase mRNA |
| 30 | Hs.78089 | -1 | 0.8315 | 0.05 | 0.0017 | 564 | 0.6327 | 1 | 0.14 | Human fetus brain mRNA for vacuolar ATPase |
| 31 | Hs.1813 | -1 | 0.827 | 0.05 | 0.0016 | 25 | 0.8201 | 0.025 | 0.001 | Homo sapiens synaptic vesicle amine transporter (SVAT1) mRNA |
| 32 | Hs.76194 | 1 | 0.8216 | 0.05 | 0.0016 | 391 | 0.6606 | 1 | 0.6 | Human ribosomal protein S5 mRNA |
| 33 | Hs.0 | -1 | 0.8171 | 0.075 | 0.0023 | 148 | 0.7315 | 0.38 | 0.0025 | Human CX3C chemokine precursor |
| 34 | Hs.155418 | -1 | 0.8153 | 0.075 | 0.0022 | 329 | 0.6729 | 1 | 0.039 | Human cancellous bone osteoblast mRNA for GS3955 |
| 35 | Hs.153322 | -1 | 0.8126 | 0.075 | 0.0021 | 98 | 0.7589 | 0.025 | 0.00026 | Human mRNA for phospholipase C |
| 36 | Hs.1440 | 1 | 0.8108 | 0.075 | 0.0021 | 92 | 0.7632 | 0.025 | 0.00027 | Human gamma amino butyric acid (GABAA) receptor beta-3 subunit |
| 37 | Hs.75137 | -1 | 0.8108 | 0.075 | 0.002 | 86 | 0.7664 | 0.025 | 0.00029 | Human mRNA for KIAA0193 gene |
| 38 | Hs.1298 | -1 | 0.8108 | 0.075 | 0.002 | 126 | 0.7433 | 0.1 | 0.00079 | Human common acute lymphoblastic leukemia antigen (CALLA) mRNA |
| 39 | Hs.164568 | -1 | 0.8108 | 0.075 | 0.0019 | 456 | 0.6493 | 1 | 0.087 | Human keratinocyte growth factor mRNA |
| 40 | Hs.2006 | -1 | 0.8099 | 0.075 | 0.0019 | 23 | 0.8255 | 0.025 | 0.0011 | Human glutathione transferase M3 (GSTM3)mRNA |
| 41 | Hs.250692 | -1 | 0.8099 | 0.075 | 0.0018 | 133 | 0.738 | 0.23 | 0.0017 | Human hepatic leukemia factor (HLF) mRNA |
| 42 | Hs.89591 | -1 | 0.809 | 0.075 | 0.0018 | 219 | 0.7052 | 1 | 0.0096 | Homo sapiens Kallmann syndrome (KAL) mRNA |
| 43 | Hs.81874 | 1 | 0.8072 | 0.075 | 0.0017 | 646 | 0.6219 | 1 | 0.18 | Human microsomal glutathione S-transferase (GST-II)mRNA |
| 44 | Hs.79059 | -1 | 0.8063 | 0.075 | 0.0017 | 87 | 0.7653 | 0.025 | 0.00029 | Human transforming growth factor-beta type III receptor (TGF-beta) |
| 45 | Hs.30054 | 1 | 0.8054 | 0.1 | 0.0022 | 74 | 0.7734 | 0.025 | 0.00034 | Human coagulation factor V mRNA |
| 46 | Hs.180015 | 1 | 0.8054 | 0.1 | 0.0022 | 470 | 0.6466 | 1 | 0.095 | Human D-dopachrome tautomerase mRNA |
| 47 | Hs.111334 | 1 | 0.8009 | 0.1 | 0.0021 | 1887 | 0.5269 | 1 | 0.83 | Human fentin L chain mRNA |
| 48 | Hs.172851 | -1 | 0.8 | 0.1 | 0.0021 | 101 | 0.7567 | 0.075 | 0.00074 | Human arginase type II mRNA |
| 49 | Hs.76244 | 1 | 0.8 | 0.1 | 0.002 | 236 | 0.7009 | 1 | 0.012 | Human spermidine synthase mRNA |
| 50 | Hs.23838 | 1 | 0.7982 | 0.1 | 0.002 | 22 | 0.8287 | 0.025 | 0.0011 | Human neuronal DHP-sensitive |
| 51 | Hs.1342 | 1 | 0.7973 | 0.1 | 0.002 | 948 | 0.5908 | 1 | 0.37 | Human cytochrome c oxidase subunit Vb (coxVb) mRNA |
| 52 | Hs.155591 | -1 | 0.7973 | 0.1 | 0.0019 | 76 | 0.7723 | 0.025 | 0.00033 | Human forkhead protein FREAC-1 mRNA |

FIG. 5b

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 53 | Hs.10755 | -1 | 0.7955 | 0.1 | 0.0019 | 17 | 0.8373 | 0.025 | 0.0015 | Human mRNA for dihydropyrimidinase |
| 54 | Hs.83383 | 1 | 0.7955 | 0.1 | 0.0019 | 235 | 0.7009 | 1 | 0.012 | Human antioxidant enzyme AOE37-2 mRNA |
| 55 | Hs.56145 | 1 | 0.7946 | 0.1 | 0.0018 | 114 | 0.7508 | 0.075 | 0.00066 | Human mRNA for NB thymosin beta |
| 56 | Hs.245188 | -1 | 0.7937 | 0.1 | 0.0018 | 113 | 0.7519 | 0.075 | 0.00066 | Human tissue inhibitor of metalloproteinases-3 mRNA |
| 57 | Hs.79345 | -1 | 0.7928 | 0.13 | 0.0022 | 724 | 0.6117 | 1 | 0.24 | Human coagulation factor VIII:C mRNA |
| 58 | Hs.79876 | -1 | 0.7928 | 0.13 | 0.0022 | 597 | 0.6284 | 1 | 0.16 | Human steroid sulfatase (STS) mRNA |
| 59 | Hs.0 | 1 | 0.7892 | 0.15 | 0.0025 | 195 | 0.7143 | 1 | 0.0073 | M17390 Human erg protein (ets-related gene) mRNA |
| 60 | Hs.66052 | -1 | 0.7883 | 0.15 | 0.0025 | 93 | 0.7626 | 0.025 | 0.00027 | 1299-1305 |
| 61 | Hs.81412 | -1 | 0.7865 | 0.15 | 0.0028 | 106 | 0.7551 | 0.075 | 0.00071 | Human mRNA for KIAA0188 gene |
| 62 | Hs.87539 | 1 | 0.7838 | 0.18 | 0.0028 | 465 | 0.6472 | 1 | 0.093 | Human aldehyde dehydrogenase (ALDH8) mRNA |
| 63 | Hs.180911 | 1 | 0.7829 | 0.18 | 0.0028 | 579 | 0.6305 | 1 | 0.15 | Human ribosomal protein (RPS4Y) isoform mRNA |
| 64 | Hs.171900 | 1 | 0.7829 | 0.18 | 0.0027 | 1910 | 0.5258 | 1 | 0.84 | Human armadillo repeat protein mRNA |
| 65 | Hs.0 | -1 | 0.7811 | 0.18 | 0.0027 | 659 | 0.6208 | 1 | 0.19 | Homo sapiens growth-arrest-specific protein (gas) mRNA |
| 66 | Hs.4437 | 1 | 0.7811 | 0.18 | 0.0027 | 188 | 0.7159 | 1 | 0.0068 | Human ribosomal protein L28 mRNA |
| 67 | Hs.32500 | -1 | 0.7793 | 0.18 | 0.0026 | 1729 | 0.5354 | 1 | 0.78 | Human mRNA for mitochondrial 3-oxoacyl-CoA thiolase |
| 68 | Hs.118065 | 1 | 0.7793 | 0.18 | 0.0026 | 467 | 0.6466 | 1 | 0.096 | Human mRNA for proteasome subunitz |
| 69 | Hs.56937 | 1 | 0.7793 | 0.18 | 0.0025 | 2391 | 0.6987 | 1 | 0.013 | Human SNC19 mRNA sequence |
| 70 | Hs.211933 | -1 | 0.7784 | 0.18 | 0.0025 | 80 | 0.7707 | 0.025 | 0.00031 | Human (clones HT-1)25 |
| 71 | Hs.738 | 1 | 0.7766 | 0.23 | 0.0032 | 1145 | 0.5752 | 1 | 0.47 | Human mRNA for ribosomal protein L14 |
| 72 | Hs.69360 | 1 | 0.7766 | 0.23 | 0.0031 | 159 | 0.7277 | 0.55 | 0.0035 | Human mitotic centromere-associated kinesin mRNA |
| 73 | Hs.80986 | 1 | 0.7757 | 0.25 | 0.0031 | 343 | 0.6702 | 1 | 0.043 | |
| 74 | Hs.75260 | -1 | 0.7757 | 0.25 | 0.0034 | 139 | 0.7358 | 0.27 | 0.002 | H.sapiens mitogen inducible gene mig-2 |
| 75 | Hs.86978 | 1 | 0.7748 | 0.25 | 0.0033 | 70 | 0.7777 | 0.025 | 0.00036 | H.sapiens mRNA for prolyl oligopeptidase |
| 76 | Hs.78894 | 1 | 0.773 | 0.27 | 0.0036 | 199 | 0.7127 | 1 | 0.0074 | Human mRNA for KIAA0161 gene |
| 77 | Hs.1050 | -1 | 0.773 | 0.27 | 0.0036 | 676 | 0.6187 | 1 | 0.2 | Human homologue of yeast sec7 mRNA |
| 78 | Hs.75746 | 1 | 0.7721 | 0.27 | 0.0035 | 81 | 0.7691 | 0.025 | 0.00031 | Human aldehyde dehydrogenase 6 mRNA |
| 79 | Hs.211578 | -1 | 0.7721 | 0.27 | 0.0035 | 1053 | 0.5822 | 1 | 0.42 | Human mad protein homolog (hMAD-3) mRNA |
| 80 | Hs.78864 | 1 | 0.7721 | 0.27 | 0.0034 | 351 | 0.6692 | 1 | 0.045 | Human IgG low affinity Fc fragment receptor (FcRIIa) mRNA |
| 81 | Hs.237356 | -1 | 0.7712 | 0.3 | 0.0037 | 61 | 0.7846 | 0.025 | 0.00041 | Human intercrine-alpha (hIRH) mRNA |
| 82 | Hs.286 | 1 | 0.7694 | 0.33 | 0.004 | 134 | 0.7374 | 0.27 | 0.0021 | Human mRNA for ribosomal protein |
| 83 | Hs.155560 | 1 | 0.7676 | 0.35 | 0.0042 | 238 | 0.6987 | 1 | 0.013 | Homo sapiens integral membrane protein |
| 84 | Hs.81875 | -1 | 0.7676 | 0.38 | 0.0045 | 341 | 0.6713 | 1 | 0.042 | Human mRNA for KIA0207 gene |

FIG. 5c

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 85 | Hs.155597 | -1 | 0.7676 | 0.38 | 0.0044 | 78 | 0.7712 | 0.025 | 0.00032 | Human adipsin/complement factor D mRNA |
| 86 | Hs.76307 | -1 | 0.7658 | 0.38 | 0.0044 | 12 | 0.841 | 0.025 | 0.0021 | Human mRNA for unknown product |
| 87 | Hs.77448 | -1 | 0.7658 | 0.38 | 0.0043 | 99 | 0.7583 | 0.025 | 0.00025 | Human pyrroline-5-carboxylate dehydrogenase (P5CDh) mRNA |
| 88 | Hs.188 | -1 | 0.764 | 0.38 | 0.0043 | 295 | 0.6794 | 1 | 0.031 | Human phosphodiesterase mRNA |
| 89 | Hs.75244 | -1 | 0.7586 | 0.45 | 0.0051 | 209 | 0.71 | 1 | 0.0077 | Human mRNA for KIAA0271 gene |
| 90 | Hs.89529 | 1 | 0.7577 | 0.47 | 0.0053 | 762 | 0.6069 | 1 | 0.27 | Human aldehyde reductase mRNA |
| 91 | Hs.170328 | -1 | 0.7577 | 0.47 | 0.0052 | 227 | 0.703 | 1 | 0.011 | Human moesin mRNA |
| 92 | Hs.51299 | 1 | 0.7568 | 0.47 | 0.0052 | 161 | 0.7272 | 0.6 | 0.0037 | Human nuclear-encoded mitochondrial NADH-ubiquinone reductase |
| 93 | Hs.50130 | -1 | 0.7568 | 0.47 | 0.0051 | 155 | 0.7293 | 0.42 | 0.0027 | Human NECDIN related protein mRNA |
| 94 | Hs.190787 | -1 | 0.7568 | 0.47 | 0.0051 | 69 | 0.7782 | 0.025 | 0.00036 | Human tissue inhibitor of metalloproteinase4 mRNA |
| 95 | Hs.171862 | -1 | 0.755 | 0.5 | 0.0053 | 280 | 0.6831 | 1 | 0.027 | Human guanylate binding protein isoform II (GBP-2)mRNA |
| 96 | Hs.180107 | 1 | 0.7541 | 0.57 | 0.006 | 44 | 0.8024 | 0.025 | 0.00057 | Human mRNA for DNA polymerase beta |
| 97 | Hs.2090 | -1 | 0.7532 | 0.63 | 0.0064 | 745 | 0.609 | 1 | 0.26 | Human prostaglandin E2 receptor mRNA |
| 98 | Hs.29117 | -1 | 0.7514 | 0.75 | 0.0077 | 848 | 0.5999 | 1 | 0.31 | H.sapiens Pur (pur-alpha) mRNA |
| 99 | Hs.26776 | -1 | 0.7514 | 0.75 | 0.0076 | 2264 | 0.5043 | 1 | 0.98 | trkC [human |
| 100 | Hs.750 | -1 | 0.7495 | 0.88 | 0.0087 | 855 | 0.5988 | 1 | 0.32 | Homo sapiens fibrillin mRNA |
| 101 | Hs.83450 | -1 | 0.7495 | 0.88 | 0.0087 | 67 | 0.7803 | 0.025 | 0.00037 | Homo sapiens laminin-related protein (LamA3) mRNA |
| 102 | Hs.687 | -1 | 0.7495 | 0.88 | 0.0086 | 26 | 0.8195 | 0.025 | 0.00096 | Human lung cytochrome P450 (IV subfamily) B1 protein |
| 103 | Hs.179774 | 1 | 0.7486 | 0.88 | 0.0085 | 739 | 0.6101 | 1 | 0.25 | Human mRNA for proteasome activator hPA28 subunit beta |
| 104 | Hs.75151 | 1 | 0.7486 | 0.88 | 0.0084 | 8 | 0.8545 | 0.025 | 0.0031 | Human GTPase activating protein (rap1GAP) mRNA |
| 105 | Hs.62661 | -1 | 0.7477 | 0.98 | 0.0093 | 319 | 0.6751 | 1 | 0.036 | Human guanylate binding protein isoform I (GBP-2) mRNA |
| 106 | Hs.283749 | -1 | 0.7468 | 1 | 0.01 | 110 | 0.7524 | 0.025 | 0.00068 | Human mRNA for RNase 4 |
| 107 | Hs.77311 | -1 | 0.7468 | 1 | 0.01 | 384 | 0.6622 | 1 | 0.057 | Human mRNA for tob family |
| 108 | Hs.71622 | -1 | 0.7468 | 1 | 0.01 | 149 | 0.7309 | 0.38 | 0.0025 | Human SWI/SNF complex 60 KDa subunit (BAF60c) mRNA |
| 109 | Hs.83656 | 1 | 0.7459 | 1 | 0.01 | 176 | 0.7191 | 1 | 0.0057 | Human GDP-dissociation inhibitor protein (Ly-GDI) mRNA |
| 110 | Hs.169718 | -1 | 0.7459 | 1 | 0.01 | 890 | 0.5956 | 1 | 0.34 | Human adult heart mRNA for neutral calponin |
| 111 | Hs.76780 | -1 | 0.7459 | 1 | 0.01 | 146 | 0.732 | 0.38 | 0.0026 | Human protein phosphatase-1 inhibitor mRNA |

FIG. 5d

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 112 | Hs.155606 | -1 | 0.745 | 1 | 0.01 | 132 | 0.7406 | 0.15 | 0.0011 | Human homeobox protein (PHOX1)mRNA |
| 113 | Hs.102497 | 1 | 0.7432 | 1 | 0.011 | 577 | 0.631 | 1 | 0.14 | Human paxillin mRNA |
| 114 | Hs.249495 | 1 | 0.7432 | 1 | 0.011 | 358 | 0.6681 | 1 | 0.046 | H.sapiens mRNA for hnRNPcore protein A1. |
| 115 | Hs.79172 | 1 | 0.7432 | 1 | 0.011 | 581 | 0.6305 | 1 | 0.15 | Human ADP/ATP carrier protein mRNA |
| 116 | Hs.250655 | 1 | 0.7432 | 1 | 0.011 | 708 | 0.6139 | 1 | 0.23 | Human prothymosin alpha mRNA(ProT-alpha) |
| 117 | Hs.323032 | 1 | 0.7423 | 1 | 0.012 | 32 | 0.8163 | 0.025 | 0.00078 | Human SIL mRNA |
| 118 | Hs.112396 | 1 | 0.7414 | 1 | 0.012 | 632 | 0.623 | 1 | 0.18 | Human mRNA for KIAA0077 gene |
| 119 | Hs.737 | 1 | 0.7414 | 1 | 0.012 | 551 | 0.6348 | 1 | 0.13 | Human transcription factor ETR101 mRNA |
| 120 | Hs.211569 | -1 | 0.7405 | 1 | 0.012 | 1184 | 0.5725 | 1 | 0.49 | Human G protein-coupled receptor kinase (GRK5) mRNA |
| 121 | Hs.177543 | -1 | 0.7396 | 1 | 0.013 | 999 | 0.5865 | 1 | 0.4 | Human MIC2 mRNA |
| 122 | Hs.47860 | 1 | 0.7396 | 1 | 0.013 | 1443 | 0.5526 | 1 | 0.65 | Human tyrosine kinase receptor p145TRK-B (TRK-B) mRNA |
| 123 | Hs.81892 | 1 | 0.7387 | 1 | 0.013 | 27 | 0.819 | 0.025 | 0.00093 | Human mRNA for KIAA0101 gene |
| 124 | Hs.262476 | 1 | 0.7387 | 1 | 0.013 | 1079 | 0.58 | 1 | .0.44 | Human S-adenosylmethionine decarboxylase mRNA |
| 125 | Hs.154210 | -1 | 0.7387 | 1 | 0.013 | 852 | 0.5994 | 1 | 0.31 | Human endothelial differentiation protein (edg-1)gene |
| 126 | Hs.182825 | 1 | 0.7387 | 1 | 0.013 | 379 | 0.6638 | 1 | 0.053 | Human ribosomal protein L35 mRNA |
| 127 | Hs.149923 | 1 | 0.736 | 1 | 0.015 | 294 | 0.6794 | 1 | 0.03 | Human X box binding protein-1 (XBP-1) mRNA |
| 128 | Hs.211600 | -1 | 0.7351 | 1 | 0.015 | 1708 | 0.5365 | 1 | 0.77 | Human tumor necrosis factor alpha inducible protein A20 mRNA |
| 129 | Hs.78913 | -1 | 0.7351 | 1 | 0.015 | 252 | 0.6933 | 1 | 0.018 | Human G protein-coupled receptor V28 mRNA |
| 130 | Hs.301613 | 1 | 0.7351 | 1 | 0.015 | 104 | 0.7562 | 0.075 | 0.00072 | Human JTV-1 (JTV-1)mRNA |
| 131 | Hs.82109 | 1 | 0.7351 | 1 | 0.015 | 186 | 0.7164 | 1 | 0.0067 | H.sapiens syndecan-1 gene (exons 2-5) |
| 132 | Hs.254105 | 1 | 0.7351 | 1 | 0.015 | 224 | 0.7035 | 1 | 0.011 | Human alpha enolase mRNA |
| 133 | Hs.172471 | -1 | 0.7342 | 1 | 0.016 | 55 | 0.7889 | 0.025 | 0.0004 | Homo sapiens (clone hKvBeta3) K+ channel beta subunit mRNA |
| 134 | Hs.211579 | -1 | 0.7342 | 1 | 0.016 | 129 | 0.7427 | 0.1 | 0.00078 | Human MUC18 glycoprotein mRNA |
| 135 | Hs.1239 | -1 | 0.7333 | 1 | 0.017 | 181 | 0.7175 | 1 | 0.0064 | Human aminopeptidase N/CD13 mRNA encoding aminopeptidase N |
| 136 | Hs.75741 | 1 | 0.7333 | 1 | 0.017 | 50 | 0.7932 | 0.025 | 00005 | Human clone HP-DAO1 diamine oxidase |
| 137 | Hs.82793 | 1 | 07333 | 1 | 0.017 | 861 | 0.5977 | 1 | 0.32 | Human mRNA for proteasomal subunit HsC10-11 |
| 138 | Hs.75458 | 1 | 0.7333 | 1 | 0.017 | 1094 | 0.5789 | 1 | 0.45 | Homo sapiens ribosomal protein L18 (RPL18) mRNA |
| 139 | Hs.505 | -1 | 0.7324 | 1 | 0.017 | 144 | 0.7336 | 0.33 | 0.0023 | Human ISL-1 (Islet-1)mRNA |
| 140 | Hs.75400 | 1 | 0.7315 | 1 | 0.018 | 1895 | 0.5263 | 1 | 0.84 | Human mRNA for KIA0280 gene |

FIG. 5e

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 141 | Hs.1989 | -1 | 0.7315 | 1 | 0.018 | 107 | 0.7551 | 0.075 | 0.0007 | Human steroid 5-alpha-reductase 2 (SRD5A2) mRNA |
| 142 | Hs.180920 | 1 | 0.7315 | 1 | 0.018 | 686 | 0.6176 | 1 | 0.2 | Human ribosomal protein S9 mRNA |
| 143 | Hs.180034 | 1 | 0.7315 | 1 | 0.018 | 772 | 0.6063 | 1 | 0.27 | Human cleavage stimulation factor 77kDa subunit mRNA |
| 144 | Hs.82124 | -1 | 0.7306 | 1 | 0.018 | 1089 | 0.5795 | 1 | 0.44 | Human laminin B1 chain mRNA |
| 145 | Hs.90408 | -1 | 0.7306 | 1 | 0.018 | 2150 | 0.5118 | 1 | 0.93 | Human neogenin mRNA |
| 146 | Hs.1602 | -1 | 0.7306 | 1 | 0.018 | 522 | 0.638 | 1 | 0.12 | Human lymphocyte dihydropyrimidine dehydrogenase mRNA |
| 147 | Hs.75139 | 1 | 0.7297 | 1 | 0.018 | 1062 | 0.5811 | 1 | 0.43 | Human arfaptin 2 |
| 148 | Hs.119 | -1 | 0.7288 | 1 | 0.018 | 661 | 0.6203 | 1 | 0.19 | Human mRNA for KIAA0105 gene |
| 149 | Hs.278027 | -1 | 0.7288 | 1 | 0.018 | 657 | 0.6208 | 1 | 0.19 | Human mRNA for LIMK-2 |
| 150 | Hs.85050 | -1 | 0.7279 | 1 | 0.019 | 296 | 0.6794 | 1 | 0.03 | Human phospholamban mRNA |
| 151 | Hs.159525 | 1 | 0.7279 | 1 | 0.019 | 54 | 0.7895 | 0.025 | 0.00046 | Human cell growth regulator CGR11 mRNA |
| 152 | Hs.94581 | -1 | 0.7279 | 1 | 0.019 | 138 | 0.7363 | 027 | 0.002 | Homo sapiens hydroxysteroid sulfotransferase SULT2B1a (HSST2) |
| 153 | Hs.75618 | 1 | 0.727 | 1 | 0.019 | 237 | 0.6998 | 1 | 0.013 | Homo sapiens rab11a GTPase mRNA |
| 154 | Hs.298262 | 1 | 0.727 | 1 | 0.019 | 729 | 0.6112 | 1 | 0.24 | H.sapiens S19 ribosomal protein mRNA |
| 155 | Hs.27747 | 1 | 0.727 | 1 | 0.019 | 797 | 0.6037 | 1 | 0.29 | Human putative endothelin receptor type B-like protein mRNA |
| 156 | Hs.56045 | -1 | 0.7261 | 1 | 0.02 | 36 | 0.8099 | 0.025 | 0.00069 | Human mRNA for stac |
| 157 | Hs.75655 | -1 | 0.7243 | 1 | 0.021 | 225 | 0.703 | 1 | 0.011 | Human thyroid hormone binding protein (p55) mRNA |
| 158 | Hs.80712 | -1 | 0.7243 | 1 | 0.022 | 260 | 0.6896 | 1 | 0.021 | Human mRNA for KIAA0202 gene |
| 159 | Hs.23111 | 1 | 0.7234 | 1 | 0.022 | 293 | 0.6799 | 1 | 0.03 | Human putative tRNA synthetase-like protein mRNA |
| 160 | Hs.2388 | 1 | 0.7225 | 1 | 0.023 | 19 | 0.8362 | 0.025 | 0.0013 | Human apolipoprotein F (APOF) mRNA |
| 161 | Hs.307164 | -1 | 0.7226 | 1 | 0.023 | 428 | 0.6547 | 1 | 0.072 | Human 3' |
| 162 | Hs.3852 | -1 | 0.7207 | 1 | 0.026 | 776 | 0.6053 | 1 | 0.28 | Human mRNA for KIAA0368 gene |
| 163 | Hs.153179 | 1 | 0.7207 | 1 | 0.026 | 1080 | 0.58 | 1 | 0.44 | Human fatty acid binding protein homologue(PA-FABP)mRNA |
| 164 | Hs.26403 | 1 | 0.7207 | 1 | 0.026 | 2113 | 0.514 | 1 | 0.91 | Human glutathione transferase Zeta 1 (GSTZ1)mRNA |
| 165 | Hs.50964 | -1 | 0.7198 | 1 | 0.027 | 421 | 0.6563 | 1 | 0.068 | Human mRNA for transmembrane carcinoembryonic antigen BGPa (f |
| 166 | Hs.92002 | -1 | 0.7198 | 1 | 0.027 | 45 | 0.8018 | 0.025 | 0.00056 | Human transducin alpha-subunit (GNAZ) mRNA |
| 167 | Hs.322903 | -1 | 0.7189 | 1 | 0.028 | 1144 | 0.5752 | 1 | 0.47 | Human mRNA for KIAA0184 gene |
| 168 | Hs.106880 | 1 | 0.7189 | 1 | 0.028 | 321 | 0.6745 | 1 | 0.036 | Homo sapiens bystin mRNA |
| 169 | Hs.244621 | 1 | 0.7189 | 1 | 0.028 | 2231 | 0.5064 | 1 | 0.96 | 5551-5557 |

FIG. 5f

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 170 | Hs.19368 | -1 | 0.7189 | 1 | 0.027 | 363 | 0.6676 | 1 | 0.046 | Human matrilin-2 precursor mRNA |
| 171 | Hs.77293 | -1 | 0.718 | 1 | 0.028 | 590 | 0.6289 | 1 | 0.15 | Human mRNA for KIAA0127 gene |
| 172 | Hs.170198 | 1 | 0.7171 | 1 | 0.03 | 131 | 0.7406 | 0.15 | 0.0011 | Human mRNA for KIAA0009 gene |
| 173 | Hs.79226 | -1 | 0.7171 | 1 | 0.029 | 41 | 0.8056 | 0.025 | 0.00061 | Human FEZ1 mRNA |
| 174 | Hs.82163 | -1 | 0.7162 | 1 | 0.031 | 153 | 0.7293 | 0.42 | 0.0028 | Human monoamine oxidase B (MAOB) mRNA |
| 175 | Hs.288215 | -1 | 0.7153 | 1 | 0.032 | 241 | 0.6976 | 1 | 0.014 | Human sialyltransferase SThM (sthm) mRNA |
| 176 | Hs.75692 | 1 | 0.7153 | 1 | 0.032 | 118 | 0.7476 | 0.075 | 0.00064 | Human asparagine synthetase mRNA |
| 177 | Hs.76901 | 1 | 0.7126 | 1 | 0.035 | 662 | 0.6203 | 1 | 0.19 | Human mRNA for protein disulfide isomerase-related protein (PDIR) |
| 178 | Hs.76064 | 1 | 0.7117 | 1 | 0.037 | 849 | 0.5999 | 1 | 0.31 | Human ribosomal protein L27a mRNA |
| 179 | Hs.80409 | -1 | 0.7108 | 1 | 0.038 | 902 | 0.5951 | 1 | 0.34 | Human growth arrest and DNA-damage-inducible protein (gadd4s) |
| 180 | Hs.155530 | -1 | 0.7108 | 1 | 0.038 | 812 | 0.6026 | 1 | 0.29 | Human interferon-gamma induced protein (IFI 16) gene |
| 181 | Hs.9614 | 1 | 0.7108 | 1 | 0.039 | 157 | 0.7288 | 0.45 | 0.0029 | Human nucleophosmin mRNA |
| 182 | Hs.76927 | 1 | 0.7108 | 1 | 0.038 | 389 | 0.6611 | 1 | 0.059 | Human putative outer mitochondrial membrane 34 kDa translocase hT |
| 183 | Hs.82961 | 1 | 0.7108 | 1 | 0.038 | 871 | 0.5977 | 1 | 0.32 | Human intestinal trefoil factor mRNA |
| 184 | Hs.75232 | -1 | 0.7099 | 1 | 0.039 | 1154 | 0.5747 | 1 | 0.48 | Human SEC14L mRNA |
| 185 | Hs.1524 | 1 | 0.709 | 1 | 0.041 | 2050 | 0.5172 | 1 | 0.9 | Human receptor 4-1BB ligand mRNA |
| 186 | Hs.106070 | -1 | 0.709 | 1 | 0.04 | 1255 | 0.5666 | 1 | 0.54 | Human Cdk-inhibitor ps57KIP2 (KIP2) mRNA |
| 187 | Hs.3260 | 1 | 0.709 | 1 | 0.04 | 1686 | 0.5376 | 1 | 0.76 | Human presenilin 1-374 (AD3-212) mRNA |
| 188 | Hs.334 | -1 | 0.7081 | 1 | 0.041 | 298 | 0.6788 | 1 | 0.031 | Human guanine nucleotide regulatory protein (tim1) mRNA |
| 189 | Hs.108885 | -1 | 0.7081 | 1 | 0.041 | 1823 | 0.5301 | 1 | 0.81 | Human mRNA for collagen VI alpha-1 C-terminal globular domain |
| 190 | Hs.22785 | -1 | 0.7072 | 1 | 0.042 | 357 | 0.6681 | 1 | 0.046 | Human GABA-A receptor epsilon subunit mRNA. |
| 191 | Hs.173912 | -1 | 0.7063 | 1 | 0.043 | 761 | 0.6069 | 1 | 0.27 | Human mRNA for eukaryotic initiation factor 4AII |
| 192 | Hs.29279 | 1 | 0.7063 | 1 | 0.043 | 1476 | 0.5505 | 1 | 0.67 | Human eyes absent homolog (Eab1) mRNA |
| 193 | Hs.151531 | -1 | 0.7054 | 1 | 0.044 | 210 | 0.71 | 1 | 0.0076 | Human calcineurin A2 mRNA |
| 194 | Hs.102267 | 1 | 0.7045 | 1 | 0.046 | 91 | 0.7637 | 0.025 | 0.00027 | Human lysyl oxidase (LOX) gene |
| 195 | Hs.74615 | -1 | 0.7045 | 1 | 0.046 | 592 | 0.6289 | 1 | 0.15 | Human platelet-derived growth factor receptor alpha (PDGFRA) mRNA |
| 196 | Hs.278503 | -1 | 0.7045 | 1 | 0.046 | 1643 | 0.5403 | 1 | 0.74 | Human RIG mRNA |
| 197 | Hs.1602 | -1 | 0.7045 | 1 | 0.046 | 524 | 0.638 | 1 | 0.12 | Human dihydropyrimidine dehydrogenase mRNA |

FIG. 5g

| Rk 0 | Unigene ID | OE | Score 0 | Pval 0 | FDR 0 | Rk 1 | Score 1 | Pval 1 | FDR 1 | Description |
|---|---|---|---|---|---|---|---|---|---|---|
| 198 | Hs.181028 | 1 | 0.7036 | 1 | 0.047 | 168 | 0.7229 | 0.85 | 0.0051 | Homo sapiens nuclear-encoded mitochondrial cytochrome c oxidase |
| 199 | Hs.89457 | 1 | 0.7036 | 1 | 0.047 | 1471 | 0.551 | 1 | 0.66 | Human mRNA for a1(XIX) collagen chain |
| 200 | Hs.62192 | 1 | 0.7036 | 1 | 0.047 | 870 | 0.5977 | 1 | 0.32 | Human tissue factor gene |

2003 Study

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 1 | Hs.771 | -1 | 0.8953 | 0.025 | 0.025 | 15 | 0.8532 | 0.025 | 0.0017 | Human liver glycogen phosphorylase mRNA |
| 2 | Hs.195850 | -1 | 0.8813 | 0.025 | 0.012 | 7 | 0.8811 | 0.025 | 0.0036 | Human keratin type II (58 kD) mRNA |
| 3 | Hs.171731 | -1 | 0.8754 | 0.025 | 0.0083 | 1 | 0.9495 | 0.025 | 0.025 | Human RACH1 (RACH1) mRNA |
| 4 | Hs.198760 | -1 | 0.869 | 0.025 | 0.0062 | 19 | 0.8495 | 0.025 | 0.0013 | H.sapiens NF-H gene |
| 5 | Hs.65029 | -1 | 0.8647 | 0.025 | 0.005 | 8 | 0.8802 | 0.025 | 0.0031 | Human gas1 gene |
| 6 | Hs.1227 | -1 | 0.8555 | 0.025 | 0.0042 | 2132 | 0.5117 | 1 | 0.95 | Human delta-aminolevulinate dehydratase mRNA |
| 7 | Hs.79217 | 1 | 0.855 | 0.025 | 0.0036 | 16 | 0.8532 | 0.025 | 0.0016 | Human pyrroline 5-carboxylate reductase mRNA |
| 8 | Hs.75151 | -1 | 0.8545 | 0.025 | 0.0031 | 104 | 0.7486 | 0.88 | 0.0084 | Human GTPase activating protein (rap1GAP) mRNA |
| 9 | Hs.9615 | -1 | 0.8459 | 0.025 | 0.0028 | 224 | 0.6919 | 1 | 0.072 | Human 20-kDa myosin light chain (MLC-2) mRNA |
| 10 | Hs.174151 | -1 | 0.8448 | 0.025 | 0.0025 | 4 | 0.8892 | 0.025 | 0.0062 | Human aldehyde oxidase (hAOX) mRNA |
| 11 | Hs.82422 | -1 | 0.8426 | 0.025 | 0.0023 | 465 | 0.6387 | 1 | 0.25 | Homo sapiens macrophage capping protein mRNA |
| 12 | Hs.76307 | -1 | 0.841 | 0.025 | 0.0021 | 86 | 0.7658 | 0.38 | 0.0044 | Human mRNA for unknown product |
| 13 | Hs.74120 | -1 | 0.841 | 0.025 | 0.0019 | 424 | 0.6468 | 1 | 0.21 | Human apM2 mRNA for GS2374 (unknown product specific to adipose tissue) |
| 14 | Hs.44 | -1 | 0.841 | 0.025 | 0.0018 | 12 | 0.8685 | 0.025 | 0.0021 | Human nerve growth factor (HBNF-1) mRNA |
| 15 | Hs.3128 | 1 | 0.841 | 0.025 | 0.0017 | 2 | 0.9081 | 0.025 | 0.012 | Human RNA polymerase II subunit (hsRPB8) mRNA |
| 16 | Hs.21223 | -1 | 0.8378 | 0.025 | 0.0016 | 243 | 0.6847 | 1 | 0.088 | Human mRNA for calponin |
| 17 | Hs.10755 | -1 | 0.8373 | 0.025 | 0.0015 | 53 | 0.7955 | 0.1 | 0.0019 | Human mRNA for dihydropyrimidinase |
| 18 | Hs.239926 | -1 | 0.8373 | 0.025 | 0.0014 | 297 | 0.6712 | 1 | 0.13 | Human methyl sterol oxidase (ERG25) mRNA |
| 19 | Hs.2388 | 1 | 0.8362 | 0.025 | 0.0013 | 160 | 0.7225 | 1 | 0.023 | Human apolipoprotein F (APOF) mRNA |
| 20 | Hs.34853 | -1 | 0.8314 | 0.025 | 0.0012 | 5 | 0.8892 | 0.025 | 0.005 | Human Id-related helix-loop-helix protein Id4 mRNA |
| 21 | Hs.77256 | 1 | 0.8298 | 0.025 | 0.0012 | 407 | 0.6505 | 1 | 0.2 | Human enhancer of zeste homolog 2 (EZH2) mRNA |
| 22 | Hs.23838 | 1 | 0.8287 | 0.025 | 0.0011 | 50 | 0.7982 | 0.1 | 0.002 | Human neuronal DHP-sensitive |

FIG. 5h

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 23 | Hs.2006 | -1 | 0.8255 | 0.025 | 0.0011 | 40 | 0.8099 | 0.075 | 0.0019 | Human glutathione transferase M3 (GSTM3) mRNA |
| 24 | Hs.113 | -1 | 0.8217 | 0.025 | 0.001 | 13 | 0.8658 | 0.025 | 0.0019 | Human cytosolic epoxide hydrolase mRNA |
| 25 | Hs.1813 | -1 | 0.8201 | 0.025 | 0.001 | 31 | 0.827 | 0.05 | 0.0016 | Homo sapiens synaptic vesicle amine transporter (SVAT) mRNA |
| 26 | Hs.687 | -1 | 0.8195 | 0.025 | 0.00096 | 102 | 0.7495 | 0.88 | 0.0086 | Human lung cytochrome P450 (IV subfamily) BI protein |
| 27 | Hs.81892 | 1 | 0.819 | 0.025 | 0.00093 | 123 | 0.7387 | 1 | 0.013 | Human mRNA for KIAA0101 gene |
| 28 | Hs.169401 | 1 | 0.819 | 0.025 | 0.00089 | 595 | 0.6198 | 1 | 0.36 | Human apolipoprotein E mRNA |
| 29 | Hs.1861 | -1 | 0.819 | 0.025 | 0.00086 | 748 | 0.6009 | 1 | 0.49 | Human palmitoylated erythrocyte membrane protein (MPP1) mRNA |
| 30 | Hs.173063 | -1 | 0.819 | 0.025 | 0.00083 | 367 | 0.6577 | 1 | 0.17 | Human transducin-like enhancer protein (TLE2) mRNA |
| 31 | Hs.89497 | 1 | 0.8174 | 0.025 | 0.00081 | 703 | 0.6063 | 1 | 0.45 | Human lamin B mRNA |
| 32 | Hs.323032 | 1 | 0.8163 | 0.025 | 0.00078 | 117 | 0.7423 | 1 | 0.012 | Human SIL mRNA |
| 33 | Hs.300772 | -1 | 0.8163 | 0.025 | 0.00076 | 414 | 0.6495 | 1 | 0.2 | Human fibroblast muscle-type tropomyosin mRNA |
| 34 | Hs.77899 | -1 | 0.8147 | 0.025 | 0.00074 | 402 | 0.6514 | 1 | 0.19 | Human tropomyosin mRNA |
| 35 | Hs.63510 | 1 | 0.8104 | 0.025 | 0.00071 | 1646 | 0.5387 | 1 | 0.84 | Human mRNA for KIAA0141 gene |
| 36 | Hs.56045 | -1 | 0.8099 | 0.025 | 0.00069 | 156 | 0.7261 | 1 | 0.02 | Human mRNA for stac |
| 37 | Hs.184339 | 1 | 0.8093 | 0.025 | 0.00068 | 250 | 0.682 | 1 | 0.097 | Human mRNA for KIAA0175 gene |
| 38 | Hs.84113 | 1 | 0.8083 | 0.025 | 0.00066 | 288 | 0.6721 | 1 | 0.13 | Homo sapiens protein tyrosine phosphatase (CIP2)mRNA |
| 39 | Hs.76224 | -1 | 0.8083 | 0.025 | 0.00064 | 28 | 0.836 | 0.025 | 0.00089 | Human extracellular protein (S1-5) mRNA |
| 40 | Hs.75335 | -1 | 0.8061 | 0.025 | 0.00062 | 798 | 0.5973 | 1 | 0.51 | H.sapiens mRNA for L-arginine:glycine amidinotransferase |
| 41 | Hs.79226 | -1 | 0.8056 | 0.025 | 0.00061 | 173 | 0.7171 | 1 | 0.029 | Human FEZ1 mRNA |
| 42 | Hs.273311 | 1 | 0.8056 | 0.025 | 0.0006 | 11 | 0.8694 | 0.025 | 0.0023 | Human transcription factor SIM2 long form mRNA |
| 43 | Hs.119301 | -1 | 0.8029 | 0.025 | 0.00058 | 246 | 0.6838 | 1 | 0.09 | Homo sapiens cellular ligand of annexin II (p11) mRNA |
| 44 | Hs.180107 | 1 | 0.8024 | 0.025 | 0.00057 | 96 | 0.7541 | 0.57 | 0.006 | Human mRNA for DNA polymerase beta |
| 45 | Hs.92002 | -1 | 0.8018 | 0.025 | 0.00056 | 166 | 0.7198 | 1 | 0.027 | Human transducin alpha-subunit (GNAZ) mRNA |
| 46 | Hs.77546 | -1 | 0.8008 | 0.025 | 0.00054 | 14 | 0.8649 | 0.025 | 0.0018 | Human mRNA for KIAA0172 gene |
| 47 | Hs.311 | 1 | 0.7965 | 0.025 | 0.00053 | 249 | 0.6829 | 1 | 0.094 | Homo sapiens glutamine PRPP amidotransferase (GPAT) mRNA complete 48 Hs.326 1 0.7943 |
| 49 | Hs.6540 | 1 | 0.7938 | 0.025 | 0.00051 | 1198 | 0.5676 | 1 | 0.67 | Human fibroblast growth factor homologous factor 2 (FHF-2) mRNA |
| 50 | Hs.75741 | -1 | 0.7932 | 0.025 | 0.0005 | 136 | 0.7333 | 1 | 0.017 | Human clone HP-DAO1 diamine oxidase |

FIG. 5i

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 51 | Hs.2785 | -1 | 0.7911 | 0.025 | 0.00049 | 24 | 0.8414 | 0.025 | 0.001 | H.sapiens gene for cytokeratin 17 |
| 52 | Hs.57783 | 1 | 0.79 | 0.025 | 0.00048 | 232 | 0.6901 | 1 | 0.075 | Human eukaryotic translation initiation factor (eIF3) mRNA |
| 53 | Hs.156346 | 1 | 0.7895 | 0.025 | 0.00047 | 322 | 0.6667 | 1 | 0.14 | Human DNA topoisomerase II (top2) mRNA |
| 54 | Hs.159525 | 1 | 0.7895 | 0.025 | 0.00046 | 151 | 0.7279 | 1 | 0.019 | Human cell growth regulator CGR11 mRNA |
| 55 | Hs.172471 | -1 | 0.7889 | 0.025 | 0.00045 | 133 | 0.7342 | 1 | 0.016 | Homo sapiens (clone hKvBeta3) K+ channel beta subunit mRNA |
| 56 | Hs.82916 | 1 | 0.7884 | 0.025 | 0.00045 | 413 | 0.6495 | 1 | 0.2 | Human chaperonin protein (Tcp20) gene complete cds |
| 57 | Hs.181046 | -1 | 0.7879 | 0.025 | 0.00044 | 1881 | 0.5252 | 1 | 0.9 | Human dual specificity phosphatase tyrosine/serine mRNA |
| 58 | Hs.21639 | -1 | 0.7873 | 0.025 | 0.00043 | 1566 | 0.5441 | 1 | 0.81 | Human APEG-1 mRNA |
| 59 | Hs.14968 | -1 | 0.7868 | 0.025 | 0.00042 | 990 | 0.582 | 1 | 0.59 | Human zinc finger protein PLAG1 mRNA |
| 60 | Hs.296259 | -1 | 0.7857 | 0.025 | 0.00042 | 1632 | 0.5396 | 1 | 0.83 | Homo sapiens paraoxonase 3 (PON3) mRNA |
| 61 | Hs.237356 | -1 | 0.7846 | 0.025 | 0.00041 | 81 | 0.7712 | 0.3 | 0.0037 | Human intercrine-alpha (hIRH) mRNA |
| 62 | Hs.153954 | 1 | 0.7841 | 0.025 | 0.0004 | 2017 | 0.5171 | 1 | 0.94 | Human mRNA for KIAA0057 gene |
| 63 | Hs.170414 | 1 | 0.7836 | 0.025 | 0.0004 | 458 | 0.6396 | 1 | 0.25 | Human subtilisin-like protein (PACE4) mRNA |
| 64 | Hs.1584 | 1 | 0.783 | 0.025 | 0.00039 | 616 | 0.6162 | 1 | 0.39 | Human germline oligomeric matrix protein (COMP) mRNA |
| 65 | Hs.234642 | -1 | 0.7814 | 0.025 | 0.00038 | 2239 | 0.5054 | 1 | 0.98 | Human AQP3 gene for aquaporine 3 (water channel) |
| 66 | Hs.93841 | 1 | 0.7814 | 0.025 | 0.00038 | 231 | 0.6901 | 1 | 0.074 | Human MaxiK potassium channel beta subunit mRNA |
| 67 | Hs.83450 | -1 | 0.7803 | 0.025 | 0.00037 | 101 | 0.7495 | 0.88 | 0.0087 | Homo sapiens laminin-related protein (LamA3) mRNA |
| 68 | Hs.172153 | -1 | 0.7798 | 0.025 | 0.00037 | 274 | 0.6748 | 1 | 0.12 | Human plasma (extracellular) mRNA for glutathione peroxidase |
| 69 | Hs.190787 | -1 | 0.7782 | 0.025 | 0.00036 | 94 | 0.7568 | 0.47 | 0.0051 | Human tissue inhibitor of metalloproteinase 4 mRNA |
| 70 | Hs.86978 | 1 | 0.7777 | 0.025 | 0.00036 | 75 | 0.7748 | 0.25 | 0.0033 | H.sapiens mRNA for prolyl oligopeptidase |
| 71 | Hs.831 | -1 | 0.7755 | 0.025 | 0.00035 | 656 | 0.6099 | 1 | 0.44 | Human hydroxymethylglutaryl-CoA lyase mRNA |
| 72 | Hs.265829 | -1 | 0.7755 | 0.025 | 0.00035 | 724 | 0.6036 | 1 | 0.47 | Human integrin alpha-3 chain mRNA |
| 73 | Hs.2025 | -1 | 0.7744 | 0.025 | 0.00034 | 3 | 0.9027 | 0.025 | 0.0083 | Human transforming growth factor-beta 3 (TGF-beta3) mRNA |
| 74 | Hs.30054 | 1 | 0.7734 | 0.025 | 0.00034 | 45 | 0.8054 | 0.1 | 0.0022 | Human coagulation factor V mRNA |
| 75 | Hs.90744 | -1 | 0.7723 | 0.025 | 0.00033 | 1616 | 0.5405 | 1 | 0.83 | Human mRNA for proteasome subunit p44.5 |
| 76 | Hs.155591 | -1 | 0.7723 | 0.025 | 0.00033 | 52 | 0.7973 | 0.1 | 0.0019 | Human forkhead protein FREAC-1 mRNA |

FIG. 5j

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 77 | Hs.77899 | -1 | 0.7723 | 0.025 | 0.00032 | 1741 | 0.5342 | 1 | 0.85 | H.sapiens tropomyosin isoform mRNA |
| 78 | Hs.155597 | -1 | 0.7712 | 0.025 | 0.00032 | 85 | 0.7676 | 0.38 | 0.0044 | Human adipsin/complement factor D mRNA |
| 79 | Hs.418 | 1 | 0.7712 | 0.025 | 0.00032 | 376 | 0.6559 | 1 | 0.18 | Human fibroblast activation protein mRNA |
| 80 | Hs.211933 | -1 | 0.7707 | 0.025 | 0.00031 | 70 | 0.7784 | 0.18 | 0.0025 | Human (clones HT-[125 |
| 81 | Hs.75746 | 1 | 0.7691 | 0.025 | 0.00031 | 78 | 0.7721 | 0.27 | 0.0035 | Human aldehyde dehydrogenase 6 mRNA |
| 82 | Hs.23311 | -1 | 0.7685 | 0.025 | 0.0003 | 304 | 0.6694 | 1 | 0.13 | Human mRNA for KIAA0367 gene |
| 83 | Hs.80296 | -1 | 0.768 | 0.025 | 0.0003 | 671 | 0.609 | 1 | 0.44 | Human PEP19 (PCP4) mRNA |
| 84 | Hs.81343 | 1 | 0.768 | 0.025 | 0.0003 | 302 | 0.6703 | 1 | 0.13 | Human mRNA for pro-alpha 1 (II) collagen 3' end C-term. triple helical |
| 86 | Hs.75137 | -1 | 0.7664 | 0.025 | 0.00029 | 37 | 0.8108 | 0.075 | 0.002 | Human mRNA for KIAA0193 gene |
| 87 | Hs.79059 | -1 | 0.7653 | 0.025 | 0.00029 | 44 | 0.8063 | 0.075 | 0.0017 | Human transforming growth factor-beta type III receptor (TGF-beta) mRNA |
| 88 | Hs.198241 | -1 | 0.7653 | 0.025 | 0.00028 | 247 | 0.6838 | 1 | 0.09 | Human placenta copper monamine oxidase mRNA |
| 89 | Hs.57698 | -1 | 0.7653 | 0.025 | 0.00028 | 824 | 0.5946 | 1 | 0.53 | Human H105e3 mRNA |
| 90 | Hs.114346 | -1 | 0.7648 | 0.025 | 0.00028 | 313 | 0.6676 | 1 | 0.14 | Human cytochrome c oxidase subunit VIIa (COX7A) muscle isoform mRNA |
| 91 | Hs.102267 | 1 | 0.7637 | 0.025 | 0.00027 | 194 | 0.7045 | 1 | 0.046 | Human lysyl oxidase (LOX) gene |
| 92 | Hs.1440 | 1 | 0.7632 | 0.025 | 0.00027 | 36 | 0.8108 | 0.075 | 0.0021 | Human gamma amino butyric acid (GABAA) receptor beta-3 subunit mRNA |
| 93 | Hs.66052 | -1 | 0.7626 | 0.025 | 0.00027 | 60 | 0.7883 | 0.15 | 0.0025 | 1299-1305 |
| 94 | Hs.155585 | -1 | 0.7626 | 0.025 | 0.00027 | 6 | 0.8838 | 0.025 | 0.0042 | Human transmembrane receptor (ror2) mRNA |
| 95 | Hs.100293 | 1 | 0.761 | 0.025 | 0.00026 | 229 | 0.691 | 1 | 0.072 | Human O-linked GlcNAc transferase mRNA |
| 96 | Hs.34789 | 1 | 0.7599 | 0.025 | 0.00026 | 338 | 0.6631 | 1 | 0.15 | Human mRNA for KIAA0115 gene |
| 97 | Hs.226213 | -1 | 0.7599 | 0.025 | 0.00026 | 202 | 0.7036 | 1 | 0.047 | Human lanosterol 14-demethylase cytochrome P450 (CYP51) mRNA |
| 98 | Hs.153322 | -1 | 0.7589 | 0.025 | 0.00026 | 35 | 0.8126 | 0.075 | 0.0021 | Human mRNA for phospholipase C |
| 99 | Hs.77448 | -1 | 0.7583 | 0.025 | 0.00025 | 87 | 0.7658 | 0.38 | 0.0043 | Human pyrroline-5-carboxylate dehydrogenase (P5CDh) mRNA |
| 100 | Hs.76289 | -1 | 0.7567 | 0.075 | 0.00075 | 998 | 0.5811 | 1 | 0.6 | Human mRNA for NADPH-flavin reductase |
| 101 | Hs.172851 | -1 | 0.7567 | 0.075 | 0.00074 | 48 | 0.8 | 0.1 | 0.0021 | Human arginase type II mRNA |
| 102 | Hs.170177 | -1 | 0.7567 | 0.075 | 0.00074 | 447 | 0.6414 | 1 | 0.24 | Human leukemogenic homolog protein (MEIS1) mRNA |

FIG. 5k

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 103 | Hs.85146 | -1 | 0.7562 | 0.075 | 0.00073 | 20 | 0.8459 | 0.025 | 0.0012 | Human erythroblastosis virus oncogene homolog 2 (ets-2) mRNA |
| 104 | Hs.301613 | 1 | 0.7562 | 0.075 | 0.00072 | 130 | 0.7351 | 1 | 0.015 | Human JTV-1 (JTV-1) mRNA |
| 105 | Hs.10526 | -1 | 0.7556 | 0.075 | 0.00071 | 17 | 0.8532 | 0.025 | 0.0015 | Human smooth muscle LIM protein (h-SmLIM) mRNA |
| 106 | Hs.81412 | -1 | 0.7551 | 0.075 | 0.00071 | 61 | 0.7865 | 0.18 | 0.0029 | Human mRNA for KIAA0188 gene |
| 107 | Hs.1989 | -1 | 0.7551 | 0.075 | 0.0007 | 141 | 0.7315 | 1 | 0.018 | Human steroid 5-alpha-reductase 2 (SRD5A2) mRNA |
| 108 | Hs.173724 | -1 | 0.7546 | 0.075 | 0.00069 | 315 | 0.6676 | 1 | 0.14 | Human creatine kinase-B mRNA |
| 109 | Hs.75893 | 1 | 0.7535 | 0.075 | 0.00069 | 210 | 0.6991 | 1 | 0.053 | Human ankyrin G (ANK-3) mRNA |
| 110 | Hs.283749 | -1 | 0.7524 | 0.075 | 0.00068 | 106 | 0.7468 | 1 | 0.01 | Human mRNA for RNase 4 |
| 111 | Hs.78748 | -1 | 0.7524 | 0.075 | 0.00068 | 1378 | 0.555 | 1 | 0.75 | Human mRNA for KIAA0237 gene |
| 112 | Hs.111903 | -1 | 0.7524 | 0.075 | 0.00067 | 1174 | 0.5694 | 1 | 0.66 | Human IgG Fc receptor hFcRn mRNA |
| 113 | Hs.245188 | -1 | 0.7519 | 0.075 | 0.00066 | 56 | 0.7937 | 0.1 | 0.0018 | Human tissue inhibitor of metalloproteinases-3 mRNA |
| 114 | Hs.56145 | 1 | 0.7508 | 0.075 | 0.00066 | 55 | 0.7946 | 0.1 | 0.0018 | Human mRNA for NB thymosin beta |
| 115 | Hs.620 | -1 | 0.7497 | 0.075 | 0.00065 | 18 | 0.8523 | 0.025 | 0.0014 | Human bullous pemphigoid antigen (BPAG1) mRNA |
| 116 | Hs.75652 | -1 | 0.7476 | 0.075 | 0.00065 | 705 | 0.6054 | 1 | 0.46 | Human glutathione S-transferase (GSTM5) mRNA |
| 117 | Hs.194765 | 1 | 0.7476 | 0.075 | 0.00064 | 253 | 0.682 | 1 | 0.096 | H. sapiens GFNX-5624 mRNA |
| 118 | Hs.75692 | 1 | 0.7476 | 0.075 | 0.00064 | 176 | 0.7153 | 1 | 0.032 | Human asparagine synthetase mRNA |
| 119 | Hs.118825 | 1 | 0.747 | 0.075 | 0.00063 | 1384 | 0.555 | 1 | 0.75 | Human MAP kinase kinase 6 (MKK6) mRNA |
| 120 | Hs.287921 | -1 | 0.746 | 0.1 | 0.00083 | 2075 | 0.5144 | 1 | 0.95 | Homo sapiens Luman mRNA |
| 121 | Hs.181013 | -1 | 0.746 | 0.1 | 0.00083 | 732 | 0.6027 | 1 | 0.48 | Homo sapiens phosphoglycerate mutase (PGAM-B) mRNA |
| 122 | Hs.79265 | -1 | 0.7454 | 0.1 | 0.00082 | 394 | 0.6523 | 1 | 0.19 | Human p126 (ST5) mRNA |
| 123 | Hs.77854 | -1 | 0.7444 | 0.1 | 0.00081 | 473 | 0.6378 | 1 | 0.26 | Human mRNA for SMP-30 (senescence marker protein-30) |
| 124 | Hs.2471 | 1 | 0.7438 | 0.1 | 0.00081 | 263 | 0.6793 | 1 | 0.1 | Human mRNA for KIAA0020 gene |
| 125 | Hs.74566 | -1 | 0.7433 | 0.1 | 0.0008 | 26 | 0.8369 | 0.025 | 0.00096 | Human mRNA for dihydropyrimidinase related protein-3 |
| 126 | Hs.1298 | -1 | 0.7433 | 0.1 | 0.00079 | 38 | 0.8108 | 0.075 | 0.002 | Human common acute lymphoblastic leukemia antigen (CALLA) mRNA |
| 127 | Hs.48450 | -1 | 0.7427 | 0.1 | 0.00079 | 412 | 0.6495 | 1 | 0.2 | Human mRNA for KIAA0222 gene |
| 128 | Hs.80620 | 1 | 0.7427 | 0.1 | 0.00078 | 1125 | 0.5721 | 1 | 0.65 | Human mRNA for KIAA0277 gene |
| 129 | Hs.211579 | -1 | 0.7427 | 0.1 | 0.00078 | 134 | 0.7342 | 1 | 0.016 | Human MUC18 glycoprotein mRNA |
| 130 | Hs.37682 | -1 | 0.7411 | 0.15 | 0.0012 | 388 | 0.6541 | 1 | 0.18 | Human tazarotene-induced gene 2 (TIG2) mRNA |

FIG. 5I

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 131 | Hs.170198 | 1 | 0.7406 | 0.15 | 0.0011 | 172 | 0.7171 | 1 | 0.03 | Human mRNA for KIAA0009 gene |
| 132 | Hs.155606 | -1 | 0.7406 | 0.15 | 0.0011 | 112 | 0.745 | 1 | 0.01 | Human homeobox protein (PHOX1) mRNA |
| 133 | Hs.250692 | -1 | 0.739 | 0.23 | 0.0017 | 41 | 0.8099 | 0.075 | 0.0018 | Human hepatic leukemia factor (HLF) mRNA |
| 134 | Hs.286 | 1 | 0.7374 | 0.27 | 0.0021 | 82 | 0.7694 | 0.33 | 0.004 | Human mRNA for ribosomal protein |
| 135 | Hs.0 | 1 | 0.7368 | 0.27 | 0.002 | 323 | 0.6667 | 1 | 0.14 | Human estrogen receptor-related protein (hERRa1) mRNA |
| 136 | Hs.227751 | -1 | 0.7363 | 0.27 | 0.002 | 593 | 0.6198 | 1 | 0.36 | Human 14 kd lectin mRNA |
| 137 | Hs.80552 | -1 | 0.7363 | 0.27 | 0.002 | 541 | 0.627 | 1 | 0.32 | |
| 138 | Hs.94581 | -1 | 0.7363 | 0.27 | 0.002 | 152 | 0.7279 | 1 | 0.019 | Homo sapiens hydroxysteroid sulfotransferase SULT2B1a (HSST2) mRNA |
| 139 | Hs.75260 | -1 | 0.7358 | 0.27 | 0.002 | 74 | 0.7757 | 0.25 | 0.0034 | H.sapiens mitogen inducible gene mig-2 |
| 140 | Hs.8136 | -1 | 0.7352 | 0.33 | 0.0023 | 1729 | 0.5351 | 1 | 0.85 | Human endothelial PAS domain protein 1 (EPAS1) mRNA |
| 141 | Hs.923 | 1 | 0.7347 | 0.33 | 0.0023 | 219 | 0.6937 | 1 | 0.067 | Human mitochondrial specific single stranded DNA binding protein mRNA |
| 142 | Hs.1594 | 1 | 0.7347 | 0.33 | 0.0023 | 239 | 0.6856 | 1 | 0.086 | Human centromere protein-A (CENP-A) mRNA |
| 143 | Hs.84728 | -1 | 0.7347 | 0.33 | 0.0023 | 379 | 0.655 | 1 | 0.18 | Human mRNA for GC-Box binding protein B1EB2 |
| 144 | Hs.505 | -1 | 0.7336 | 0.33 | 0.0023 | 139 | 0.7324 | 1 | 0.017 | Human ISL-1 (Islet-1) mRNA |
| 145 | Hs.93199 | -1 | 0.7325 | 0.33 | 0.0022 | 2271 | 0.5036 | 1 | 0.99 | Human 2 |
| 146 | Hs.76780 | 1 | 0.732 | 0.38 | 0.0026 | 111 | 0.7459 | 1 | 0.01 | Human protein phosphatase-1 inhibitor mRNA |
| 147 | Hs.77695 | 1 | 0.7315 | 0.38 | 0.0026 | 509 | 0.6306 | 1 | 0.3 | Human mRNA for KIAA0008 gene |
| 148 | Hs.0 | -1 | 0.7315 | 0.38 | 0.0025 | 33 | 0.8171 | 0.075 | 0.0023 | Human CX3C chemokine precursor |
| 149 | Hs.71622 | -1 | 0.7309 | 0.38 | 0.0025 | 108 | 0.7468 | 1 | 0.01 | Human SWI/SNF complex 60 KDa subunit (BAF60c) mRNA |
| 150 | Hs.93002 | 1 | 0.7309 | 0.38 | 0.0025 | 361 | 0.6595 | 1 | 0.16 | Human cyclin-selective ubiquitin carrier protein mRNA |
| 151 | Hs.33084 | -1 | 0.7304 | 0.38 | 0.0025 | 22 | 0.8432 | 0.025 | 0.0011 | Human glucose transport-like 5 (GLUT5) mRNA |
| 152 | Hs.288642 | -1 | 0.7299 | 0.4 | 0.0026 | 919 | 0.5874 | 1 | 0.56 | Human GTP-binding protein superfamily |
| 153 | Hs.82163 | -1 | 0.7293 | 0.42 | 0.0028 | 174 | 0.7162 | 1 | 0.031 | Human monoamine oxidase B (MAOB) mRNA |
| 154 | Hs.2133 | -1 | 0.7293 | 0.42 | 0.0028 | 1371 | 0.5559 | 1 | 0.75 | Human retinal pigment epithelium-specific 61 kDa protein (RPE65) mRNA |
| 155 | Hs.50130 | -1 | 0.7293 | 0.42 | 0.0027 | 93 | 0.7568 | 0.47 | 0.0051 | Human NFCDIN related protein mRNA |
| 156 | Hs.159608 | -1 | 0.7293 | 0.42 | 0.0027 | 266 | 0.6784 | 1 | 0.11 | Human microsomal aldehyde dehydrogenase (ALD10) mRNA |

FIG. 5m

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 157 | Hs.9614 | 1 | 0.7288 | 0.45 | 0.0029 | 181 | 0.7108 | 1 | 0.039 | Human nucleophosmin mRNA |
| 158 | Hs.1827 | -1 | 0.7277 | 0.55 | 0.0035 | 293 | 0.6712 | 1 | 0.13 | Human nerve growth factor receptor mRNA |
| 159 | Hs.69360 | 1 | 0.7277 | 0.55 | 0.0035 | 72 | 0.7766 | 0.23 | 0.0031 | Human mitotic centromere-associated kinesin mRNA |
| 160 | Hs.145279 | 1 | 0.7277 | 0.55 | 0.0034 | 666 | 0.6099 | 1 | 0.43 | Human set gene |
| 161 | Hs.51299 | 1 | 0.7272 | 0.6 | 0.0037 | 92 | 0.7568 | 0.47 | 0.0052 | Human nuclear-encoded mitochondrial NADH-ubiquinone reductase 24Kd 162 Hs.78888 -1 0.7261 0.67 0.0042 |
| 163 | Hs.62041 | -1 | 0.7261 | 0.67 | 0.0041 | 445 | 0.6414 | 1 | 0.24 | Human nidogen mRNA |
| 164 | Hs.89463 | -1 | 0.7261 | 0.67 | 0.0041 | 729 | 0.6036 | 1 | 0.47 | Human calcium activated potassium channel (hslo) mRNA |
| 165 | Hs.89463 | -1 | 0.7261 | 0.67 | 0.0041 | 2231 | 0.5063 | 1 | 0.97 | Human large-conductance calcium-activated potassium channel (hSl |
| 166 | Hs.1560 | 1 | 0.724 | 0.83 | 0.005 | 974 | 0.5829 | 1 | 0.59 | Human mRNA for KIAA0086 gene |
| 167 | Hs.108332 | 1 | 0.7234 | 0.85 | 0.0051 | 1725 | 0.5351 | 1 | 0.85 | Human E2 ubiquitin conjugating enzyme UbcH5B (UBCH5B) mRNA |
| 168 | Hs.181028 | 1 | 0.7229 | 0.85 | 0.0051 | 198 | 0.7036 | 1 | 0.047 | Homo sapiens nuclear-encoded mitochondrial cytochrome c oxidase Va subunit 169 Hs.290 -1 |
| 170 | Hs.283952 | 1 | 0.7223 | 0.85 | 0.005 | 1654 | 0.5387 | 1 | 0.84 | Homo sapiens Xq28 genomic DNA in the region of the ALD locus |
| 173 | Hs.75981 | -1 | 0.7213 | 0.9 | 0.0052 | 1252 | 0.5631 | 1 | 0.71 | Human tRNA-guanine transglycosylase mRNA |
| 174 | Hs.75794 | -1 | 0.7197 | 0.95 | 0.0055 | 528 | 0.6288 | 1 | 0.31 | Human lysophosphatidic acid receptor homolog mRNA |
| 175 | Hs.220689 | 1 | 0.7191 | 1 | 0.0057 | 1333 | 0.5586 | 1 | 0.73 | Human GAP SH3 binding protein mRNA |
| 176 | Hs.83656 | 1 | 0.7191 | 1 | 0.0057 | 109 | 0.7459 | 1 | 0.01 | Human GDP-dissociation inhibitor protein (Ly-GDI) mRNA |
| 177 | Hs.3235 | -1 | 0.7186 | 1 | 0.0058 | 2128 | 0.5117 | 1 | 0.95 | Human mRNA for cytokeratin 4 C-terminal region |
| 178 | Hs.183109 | 1 | 0.718 | 1 | 0.006 | 212 | 0.6982 | 1 | 0.055 | Human monoamine oxidase A (MAOA) mRNA |
| 179 | Hs.118625 | -1 | 0.718 | 1 | 0.006 | 290 | 0.6721 | 1 | 0.13 | Human hexokinase 1 (HK1) mRNA |
| 180 | Hs.2022 | 1 | 0.7175 | 1 | 0.0064 | 1222 | 0.5649 | 1 | 0.7 | Homo sapiens transglutaminase E3 (TGASE3) mRNA |
| 181 | Hs.1239 | -1 | 0.7175 | 1 | 0.0064 | 135 | 0.7333 | 1 | 0.017 | Human aminopeptidase N/CD13 mRNA encoding aminopeptidase N |
| 182 | Hs.3446 | 1 | 0.7175 | 1 | 0.0063 | 2103 | 0.5135 | 1 | 0.94 | Homo sapiens MAP kinase kinase mRNA |
| 183 | Hs.259802 | -1 | 0.717 | 1 | 0.0067 | 215 | 0.6973 | 1 | 0.057 | Human trophinin mRNA |
| 184 | Hs.41691 | -1 | 0.717 | 1 | 0.0067 | 1947 | 0.5216 | 1 | 0.92 | Human bZip protein B-ATF mRNA |

FIG. 5n

| Rk 1 | Unigene ID | OE | Score 0 | Pval 1 | FDR 1 | Rk 0 | Score 0 | Pval 0 | FDR 0 | Description |
|---|---|---|---|---|---|---|---|---|---|---|
| 185 | Hs.97496 | 1 | 0.7164 | 1 | 0.0068 | 2245 | 0.5054 | 1 | 0.98 | Homo sapiens GLI-Krupple related protein (YY1) mRNA |
| 186 | Hs.82109 | -1 | 0.7164 | 1 | 0.0067 | 131 | 0.7351 | 1 | 0.015 | H.sapiens syndecan-1 gene (exons 2-5) |
| 187 | Hs.110903 | -1 | 0.7159 | 1 | 0.0068 | 946 | 0.5847 | 1 | 0.58 | Homo sapiens transmembrane protein mRNA |
| 188 | Hs.4437 | 1 | 0.7159 | 1 | 0.0068 | 66 | 0.7811 | 0.18 | 0.0027 | Human ribosomal protein L28 mRNA |
| 189 | Hs.86724 | 1 | 0.7159 | 1 | 0.0067 | 399 | 0.6514 | 1 | 0.19 | Human GTP cyclohydrolase I mRNA |
| 190 | Hs.277704 | 1 | 0.7159 | 1 | 0.0067 | 233 | 0.6892 | 1 | 0.076 | Human 150 kDa oxygen-regulated protein ORP150 mRNA |
| 191 | Hs.79295 | 1 | 0.7154 | 1 | 0.0071 | 1185 | 0.5685 | 1 | 0.67 | Human G-rich sequence factor-1 (GRSF-1) mRNA |
| 192 | Hs.283006 | 1 | 0.7148 | 1 | 0.0074 | 222 | 0.6928 | 1 | 0.068 | Homo sapiens phospholipase C beta 4 (PLCB4) mRNA |
| 193 | Hs.8265 | 1 | 0.7148 | 1 | 0.0074 | 1432 | 0.5514 | 1 | 0.78 | Human transglutaminase (TGase) mRNA |
| 194 | Hs.36508 | -1 | 0.7148 | 1 | 0.0073 | 351 | 0.6613 | 1 | 0.16 | Human beige protein homolog (chs) mRNA |
| 195 | Hs.0 | 1 | 0.7143 | 1 | 0.0073 | 59 | 0.7892 | 0.15 | 0.0025 | M17390 Human erg protein (ets-related gene) mRNA |
| 196 | Hs.211579 | -1 | 0.7137 | 1 | 0.0074 | 1966 | 0.5207 | 1 | 0.92 | Human isolate JuSo MUC18 glycoprotein mRNA (3' variant) |
| 197 | Hs.211579 | -1 | 0.7137 | 1 | 0.0074 | 419 | 0.6486 | 1 | 0.2 | Human isolate JuSo MUC18 glycoprotein mRNA (3' variant) |
| 198 | Hs.158282 | -1 | 0.7132 | 1 | 0.0074 | 435 | 0.6432 | 1 | 0.23 | Human mRNA for KIAA0040 gene |
| 199 | Hs.78894 | 1 | 0.7127 | 1 | 0.0074 | 76 | 0.773 | 0.27 | 0.0036 | Human mRNA for KIAA0161 gene |
| 200 | Hs.80617 | 1 | 0.7127 | 1 | 0.0074 | 347 | 0.6622 | 1 | 0.15 | Human ribosomal protein S16 mRNA |

FIG. 5o

| Rk | Unigene ID | Over Expr | Scor | Rk0 | Score0 | Rk1 | Score1 | Description |
|---|---|---|---|---|---|---|---|---|
| 1 | Hs.195850 | -1 | 0.8811 | 7 | 0.8811 | 2 | 0.8813 | Human keratin type II (58 kD) mRNA |
| 2 | Hs.171731 | -1 | 0.8754 | 1 | 0.9495 | 3 | 0.8754 | Human RACH1 (RACH1) mRNA |
| 3 | Hs.65029 | -1 | 0.8647 | 8 | 0.8802 | 5 | 0.8647 | Human gas1 gene |
| 4 | Hs.771 | -1 | 0.8532 | 15 | 0.8532 | 1 | 0.8953 | Human liver glycogen phosphorylase mRNA |
| 5 | Hs.79217 | 1 | 0.8532 | 16 | 0.8532 | 7 | 0.855 | Human pyrroline 5-carboxylate reductase mRNA |
| 6 | Hs.198760 | -1 | 0.8495 | 19 | 0.8495 | 4 | 0.869 | H.sapiens NF-H gene |
| 7 | Hs.174151 | -1 | 0.8448 | 4 | 0.8892 | 10 | 0.8448 | Human aldehyde oxidase (hAOX) mRNA |
| 8 | Hs.44 | -1 | 0.841 | 12 | 0.8685 | 14 | 0.841 | Human nerve growth factor (HBNF-1) mRNA |
| 9 | Hs.3128 | 1 | 0.841 | 2 | 0.9081 | 15 | 0.841 | Human RNA polymerase II subunit (hsRPB8) mRNA |
| 10 | Hs.34853 | -1 | 0.8314 | 5 | 0.8892 | 20 | 0.8314 | Human Id-related helix-loop-helix protein Id4 mRNA |
| 11 | Hs.113 | -1 | 0.8217 | 13 | 0.8658 | 24 | 0.8217 | Human cytosolic epoxide hydrolase mRNA |
| 12 | Hs.1813 | -1 | 0.8201 | 31 | 0.827 | 25 | 0.8201 | Homo sapiens synaptic vesicle amine transporter (SVAT) mRNA |
| 13 | Hs.2006 | -1 | 0.8099 | 40 | 0.8099 | 23 | 0.8255 | Human glutathione transferase M3 (GSTM3) mRNA |
| 14 | Hs.76224 | -1 | 0.8083 | 28 | 0.836 | 39 | 0.8083 | Human extracellular protein (S1-5) mRNA |
| 15 | Hs.27311 | 1 | 0.8056 | 11 | 0.8694 | 42 | 0.8056 | Human transcription factor SIM2 long form mRNA |
| 16 | Hs.77546 | -1 | 0.8008 | 14 | 0.8649 | 46 | 0.8008 | Human mRNA for KIAA0172 gene |
| 17 | Hs.23838 | 1 | 0.7982 | 50 | 0.7982 | 22 | 0.8287 | Human neuronal DHP-sensitive |
| 18 | Hs.10755 | -1 | 0.7955 | 53 | 0.7955 | 17 | 0.8373 | Human mRNA for dihydropyrimidinase |
| 19 | Hs.2785 | -1 | 0.7911 | 24 | 0.8414 | 51 | 0.7911 | H.sapiens gene for cytokeratin 17 |
| 20 | Hs.86978 | 1 | 0.7748 | 75 | 0.7748 | 70 | 0.7777 | H.sapiens mRNA for prolyl oligopeptidase |
| 21 | Hs.2025 | -1 | 0.7744 | 3 | 0.9027 | 73 | 0.7744 | Human transforming growth factor-beta 3 (TGF-beta3) mRNA |
| 22 | Hs.30054 | 1 | 0.7734 | 45 | 0.8054 | 74 | 0.7734 | Human coagulation factor V mRNA |
| 23 | Hs.155591 | -1 | 0.7723 | 52 | 0.7973 | 76 | 0.7723 | Human forkhead protein FREAC-1 mRNA |
| 24 | Hs.237356 | -1 | 0.7712 | 81 | 0.7712 | 61 | 0.7846 | Human intercrine-alpha (hIRH) mRNA |
| 25 | Hs.211933 | -1 | 0.7707 | 70 | 0.7784 | 80 | 0.7707 | Human (clones HT-[125 |
| 26 | Hs.75746 | 1 | 0.7691 | 78 | 0.7721 | 81 | 0.7691 | Human aldehyde dehydrogenase 6 mRNA |
| 27 | Hs.155597 | -1 | 0.7676 | 85 | 0.7676 | 78 | 0.7712 | Human adipsin/complement factor D mRNA |
| 28 | Hs.75111 | -1 | 0.7669 | 21 | 0.8432 | 85 | 0.7669 | Human cancellous bone osteoblast mRNA for serin protease with IGF-binding motif |

FIG. 6a

| Rk | Unigene ID | Over Expr | Scor | Rk0 | Score0 | Rk1 | Score1 | Description |
|---|---|---|---|---|---|---|---|---|
| 29 | Hs.75137 | -1 | 0.7664 | 37 | 0.8108 | 86 | 0.7664 | Human mRNA for KIAA0193 gene |
| 30 | Hs.76307 | -1 | 0.7658 | 86 | 0.7658 | 12 | 0.841 | Human mRNA for unknown product |
| 31 | Hs.79059 | -1 | 0.7653 | 44 | 0.8063 | 87 | 0.7653 | Human transforming growth factor-beta type III receptor (TGF-beta) mRNA |
| 32 | Hs.1440 | 1 | 0.7632 | 36 | 0.8108 | 92 | 0.7632 | Human gamma amino butyric acid (GABAA) receptor beta-3 subunit mRNA |
| 33 | Hs.66052 | -1 | 0.7626 | 60 | 0.7883 | 93 | 0.7626 | 1299-1305 |
| 34 | Hs.155585 | -1 | 0.7626 | 6 | 0.8838 | 94 | 0.7626 | Human transmembrane receptor (ror2) mRNA |
| 35 | Hs.153322 | -1 | 0.7589 | 35 | 0.8126 | 98 | 0.7589 | Human mRNA for phospholipase C |
| 36 | Hs.77448 | -1 | 0.7583 | 87 | 0.7658 | 99 | 0.7583 | Human pyrroline-5-carboxylate dehydrogenase (P5CDh) mRNA |
| 37 | Hs.190787 | -1 | 0.7568 | 94 | 0.7568 | 69 | 0.7782 | Human tissue inhibitor of metalloproteinase 4 mRNA |
| 38 | Hs.172851 | -1 | 0.7567 | 48 | 0.8 | 101 | 0.7567 | Human arginase type II mRNA |
| 39 | Hs.85146 | -1 | 0.7562 | 20 | 0.8459 | 103 | 0.7562 | Human erythroblastosis virus oncogene homolog 2 (ets-2) mRNA |
| 40 | Hs.10526 | -1 | 0.7556 | 17 | 0.8532 | 105 | 0.7556 | Human smooth muscle LIM protein (h-SmLIM) mRNA |
| 41 | Hs.81412 | -1 | 0.7551 | 61 | 0.7865 | 106 | 0.7551 | Human mRNA for KIAA0188 gene |
| 42 | Hs.180107 | 1 | 0.7541 | 96 | 0.7541 | 44 | 0.8024 | Human mRNA for DNA polymerase beta |
| 43 | Hs.245188 | -1 | 0.7519 | 56 | 0.7937 | 113 | 0.7519 | Human tissue inhibitor of metalloproteinases-3 mRNA |
| 44 | Hs.56145 | 1 | 0.7508 | 55 | 0.7946 | 114 | 0.7508 | Human mRNA for NB thymosin beta |
| 45 | Hs.620 | -1 | 0.7497 | 18 | 0.8523 | 115 | 0.7497 | Human bullous pemphigoid antigen (BPAG1) mRNA |
| 46 | Hs.83450 | -1 | 0.7495 | 101 | 0.7495 | 67 | 0.7803 | Homo sapiens laminin-related protein (LamA3) mRNA |
| 47 | Hs.687 | -1 | 0.7495 | 102 | 0.7495 | 26 | 0.8195 | Human lung cytochrome P450 (IV subfamily) BI protein |
| 48 | Hs.75151 | 1 | 0.7486 | 104 | 0.7486 | 8 | 0.8545 | Human GTPase activating protein (rap1GAP) mRNA |
| 49 | Hs.283749 | -1 | 0.7468 | 106 | 0.7468 | 110 | 0.7524 | Human mRNA for RNase 4 |
| 50 | Hs.74566 | -1 | 0.7433 | 26 | 0.8369 | 125 | 0.7433 | Human mRNA for dihydropyrimidinase related protein-3 |
| 51 | Hs.1298 | -1 | 0.7433 | 38 | 0.8108 | 126 | 0.7433 | Human common acute lymphoblastic leukemia antigen (CALLA) mRNA |
| 52 | Hs.323032 | 1 | 0.7423 | 117 | 0.7423 | 32 | 0.8163 | Human SIL mRNA |
| 53 | Hs.155606 | -1 | 0.7406 | 112 | 0.745 | 132 | 0.7406 | Human homeobox protein (PHOX1) mRNA |
| 54 | Hs.250692 | -1 | 0.739 | 41 | 0.8099 | 133 | 0.739 | Human hepatic leukemia factor (HLF) mRNA |
| 55 | Hs.81892 | 1 | 0.7387 | 123 | 0.7387 | 27 | 0.819 | Human mRNA for KIAA0101 gene |
| 56 | Hs.286 | 1 | 0.7374 | 82 | 0.7694 | 134 | 0.7374 | Human mRNA for ribosomal protein |

FIG. 6b

| Rk | Unigene ID | Over Expr | Scor | Rk0 | Score0 | Rk1 | Score1 | Description |
|---|---|---|---|---|---|---|---|---|
| 57 | Hs.75260 | -1 | 0.7358 | 74 | 0.7757 | 139 | 0.7358 | H.sapiens mitogen inducible gene mig-2 |
| 58 | Hs.301613 | 1 | 0.7351 | 130 | 0.7351 | 104 | 0.7562 | Human JTV-1 (JTV-1) mRNA |
| 59 | Hs.172471 | -1 | 0.7342 | 133 | 0.7342 | 55 | 0.7889 | Homo sapiens (clone hKvBeta3) K+ channel beta subunit mRNA |
| 60 | Hs.211579 | -1 | 0.7342 | 134 | 0.7342 | 129 | 0.7427 | Human MUC18 glycoprotein mRNA |
| 61 | Hs.75741 | -1 | 0.7333 | 136 | 0.7333 | 50 | 0.7932 | Human clone HP-DAO1 diamine oxidase |
| 62 | Hs.505 | -1 | 0.7324 | 139 | 0.7324 | 144 | 0.7336 | Human ISL-1 (Islet-1) mRNA |
| 63 | Hs.76780 | -1 | 0.732 | 111 | 0.7459 | 146 | 0.732 | Human protein phosphatase-1 inhibitor mRNA |
| 64 | Hs.1989 | -1 | 0.7315 | 141 | 0.7315 | 107 | 0.7551 | Human steroid 5-alpha-reductase 2 (SRD5A2) mRNA |
| 65 | Hs.0 | -1 | 0.7315 | 33 | 0.8171 | 148 | 0.7315 | Human CX3C chemokine precursor |
| 66 | Hs.71622 | -1 | 0.7309 | 108 | 0.7468 | 149 | 0.7309 | Human SWI/SNF complex 60 KDa subunit (BAF60c) mRNA |
| 67 | Hs.33084 | -1 | 0.7304 | 22 | 0.8432 | 151 | 0.7304 | Human glucose transport-like 5 (GLUT5) mRNA |
| 68 | Hs.50130 | -1 | 0.7293 | 93 | 0.7568 | 155 | 0.7293 | Human NECDIN related protein mRNA |
| 69 | Hs.159525 | 1 | 0.7279 | 151 | 0.7279 | 54 | 0.7895 | Human cell growth regulator CGR11 mRNA |
| 70 | Hs.94581 | -1 | 0.7279 | 152 | 0.7279 | 138 | 0.7363 | Homo sapiens hydroxysteroid sulfotransferase SULT2B1a (HSST2) mRNA |
| 71 | Hs.69360 | 1 | 0.7277 | 72 | 0.7766 | 159 | 0.7277 | Human mitotic centromere-associated kinesin mRNA |
| 72 | Hs.51299 | 1 | 0.7272 | 92 | 0.7568 | 161 | 0.7272 | Human nuclear-encoded mitochondrial NADH-ubiquinone reductase 24Kd subunit mRNA |
| 73 | Hs.56045 | -1 | 0.7261 | 156 | 0.7261 | 36 | 0.8099 | Human mRNA for stac |
| 74 | Hs.2388 | 1 | 0.7225 | 160 | 0.7225 | 19 | 0.8362 | Human apolipoprotein F (APOF) mRNA |
| 75 | Hs.92002 | -1 | 0.7198 | 166 | 0.7198 | 45 | 0.8018 | Human transducin alpha-subunit (GNAZ) mRNA |
| 76 | Hs.83656 | 1 | 0.7191 | 109 | 0.7459 | 176 | 0.7191 | Human GDP-dissociation inhibitor protein (Ly-GDI) mRNA |
| 77 | Hs.1239 | -1 | 0.7175 | 135 | 0.7333 | 181 | 0.7175 | Human aminopeptidase N/CD13 mRNA encoding aminopeptidase N |
| 78 | Hs.170198 | 1 | 0.7171 | 172 | 0.7171 | 131 | 0.7406 | Human mRNA for KIAA0009 gene |
| 79 | Hs.79226 | -1 | 0.7171 | 173 | 0.7171 | 41 | 0.8056 | Human FEZ1 mRNA |
| 80 | Hs.82109 | -1 | 0.7164 | 131 | 0.7351 | 186 | 0.7164 | H.sapiens syndecan-1 gene (exons 2-5) |
| 81 | Hs.82163 | -1 | 0.7162 | 174 | 0.7162 | 153 | 0.7293 | Human monoamine oxidase B (MAOB) mRNA |
| 82 | Hs.4437 | 1 | 0.7159 | 66 | 0.7811 | 188 | 0.7159 | Human ribosomal protein L28 mRNA |
| 83 | Hs.75692 | 1 | 0.7153 | 176 | 0.7153 | 118 | 0.7476 | Human asparagine synthetase mRNA |
| 84 | Hs.0 | 1 | 0.7143 | 59 | 0.7892 | 195 | 0.7143 | M17390 Human erg protein (ets-related gene) mRNA |
| 85 | Hs.78894 | 1 | 0.7127 | 76 | 0.773 | 199 | 0.7127 | Human mRNA for KIAA0161 gene |
| 86 | Hs.9614 | 1 | 0.7108 | 181 | 0.7108 | 157 | 0.7288 | Human nucleophosmin mRNA |

FIG. 6c

| Rk | Unigene ID | Over Expr | Scor | Rk0 | Score0 | Rk1 | Score1 | Description |
|---|---|---|---|---|---|---|---|---|
| 87 | Hs.75244 | -1 | 0.71 | 89 | 0.7586 | 209 | 0.71 | Human mRNA for KIAA0271 gene |
| 88 | Hs.151531 | -1 | 0.7054 | 193 | 0.7054 | 210 | 0.71 | Human calcineurin A2 mRNA |
| 89 | Hs.89591 | -1 | 0.7052 | 42 | 0.809 | 219 | 0.7052 | Homo sapiens Kallmann syndrome (KAL) mRNA |
| 90 | Hs.102267 | 1 | 0.7045 | 194 | 0.7045 | 91 | 0.7637 | Human lysyl oxidase (LOX) gene |
| 91 | Hs.181028 | 1 | 0.7036 | 198 | 0.7036 | 168 | 0.7229 | Homo sapiens nuclear-encoded mitochondrial cytochrome c oxidase Va subunit mRNA |
| 92 | Hs.226213 | -1 | 0.7036 | 202 | 0.7036 | 97 | 0.7599 | Human lanosterol 14-demethylase cytochrome P450 (CYP51) mRNA |
| 93 | Hs.254105 | 1 | 0.7035 | 132 | 0.7351 | 224 | 0.7035 | Human alpha enolase mRNA |
| 94 | Hs.75655 | 1 | 0.703 | 157 | 0.7243 | 225 | 0.703 | Human thyroid hormone binding protein (p55) mRNA |
| 95 | Hs.170328 | -1 | 0.703 | 91 | 0.7577 | 227 | 0.703 | Human moesin mRNA |
| 96 | Hs.78909 | -1 | 0.7009 | 23 | 0.8423 | 234 | 0.7009 | Human Tis11d gene |
| 97 | Hs.83383 | 1 | 0.7009 | 54 | 0.7955 | 235 | 0.7009 | Human antioxidant enzyme AOE37-2 mRNA |
| 98 | Hs.76244 | 1 | 0.7009 | 49 | 0.8 | 236 | 0.7009 | Human spermidine synthase mRNA |
| 99 | Hs.75618 | 1 | 0.6998 | 153 | 0.727 | 237 | 0.6998 | Homo sapiens rab11a GTPase mRNA |
| 100 | Hs.75893 | 1 | 0.6991 | 210 | 0.6991 | 109 | 0.7535 | Human ankyrin G (ANK-3) mRNA |
| 101 | Hs.155560 | 1 | 0.6987 | 83 | 0.7676 | 238 | 0.6987 | Homo sapiens integral membrane protein |
| 102 | Hs.56937 | 1 | 0.6987 | 69 | 0.7793 | 239 | 0.6987 | Human SNC19 mRNA sequence |
| 103 | Hs.183109 | 1 | 0.6982 | 212 | 0.6982 | 178 | 0.718 | Human monoamine oxidase A (MAOA) mRNA |
| 104 | Hs.288215 | -1 | 0.6976 | 175 | 0.7153 | 241 | 0.6976 | Human sialyltransferase SThM (sthm) mRNA |
| 105 | Hs.259802 | -1 | 0.6973 | 215 | 0.6973 | 183 | 0.717 | Human trophinin mRNA |
| 106 | Hs.923 | 1 | 0.6937 | 219 | 0.6937 | 141 | 0.7347 | Human mitochondrial specific single stranded DNA binding protein mRNA |
| 107 | Hs.78913 | -1 | 0.6933 | 129 | 0.7351 | 252 | 0.6933 | Human G protein-coupled receptor V28 mRNA |
| 108 | Hs.283006 | 1 | 0.6928 | 222 | 0.6928 | 192 | 0.7148 | Homo sapiens phospholipase C beta 4 (PLCB4) mRNA |
| 109 | Hs.9615 | -1 | 0.6919 | 224 | 0.6919 | 9 | 0.8459 | Human 20-kDa myosin light chain (MLC-2) mRNA |
| 110 | Hs.100293 | 1 | 0.691 | 229 | 0.691 | 95 | 0.761 | Human O-linked GlcNAc transferase mRNA |
| 111 | Hs.93841 | -1 | 0.6901 | 231 | 0.6901 | 66 | 0.7814 | Human MaxiK potassium channel beta subunit mRNA |
| 112 | Hs.57783 | 1 | 0.6901 | 232 | 0.6901 | 52 | 0.79 | Human eukaryotic translation initiation factor (eIF3) mRNA |
| 113 | Hs.80712 | -1 | 0.6896 | 158 | 0.7243 | 260 | 0.6896 | Human mRNA for KIAA0202 gene |
| 114 | Hs.277704 | 1 | 0.6892 | 233 | 0.6892 | 190 | 0.7159 | Human 150 kDa oxygen-regulated protein ORP150 mRNA |
| 115 | Hs.85302 | -1 | 0.689 | 10 | 0.873 | 268 | 0.689 | Human dsRNA adenosine deaminase DRADA2b (DRADA2b) mRNA |

FIG. 6d

| 116 | Hs.1594 | 1 | 0.6856 | 239 | 0.6856 | 142 | 0.7347 | Human centromere protein-A (CENP-A) mRNA |
|---|---|---|---|---|---|---|---|---|
| 117 | Hs.6196 | -1 | 0.6847 | 241 | 0.6847 | 242 | 0.6976 | Human integrin-linked kinase (ILK) mRNA |
| 118 | Hs.21223 | -1 | 0.6847 | 243 | 0.6847 | 16 | 0.8378 | Human mRNA for calponin |
| 119 | Hs.119301 | -1 | 0.6838 | 246 | 0.6838 | 43 | 0.8029 | Homo sapiens cellular ligand of annexin II (p11) mRNA |
| 120 | Hs.198241 | -1 | 0.6838 | 247 | 0.6838 | 88 | 0.7653 | Human placenta copper monamine oxidase mRNA |
| 121 | Hs.171862 | -1 | 0.6831 | 95 | 0.755 | 280 | 0.6831 | Human guanylate binding protein isoform II (GBP-2) mRNA |
| 122 | Hs.311 | 1 | 0.6829 | 249 | 0.6829 | 47 | 0.7965 | Homo sapiens glutamine PRPP amidotransferase (GPAT) mRNA complete cds |
| 123 | Hs.1869 | -1 | 0.6821 | 27 | 0.836 | 284 | 0.6821 | Human phosphoglucomutase 1 (PGM1) mRNA |
| 124 | Hs.184339 | 1 | 0.682 | 250 | 0.682 | 37 | 0.8093 | Human mRNA for KIAA0175 gene |
| 125 | Hs.194765 | 1 | 0.682 | 253 | 0.682 | 117 | 0.7476 | H.sapiens GENX-5624 mRNA |
| 126 | Hs.79404 | -1 | 0.682 | 256 | 0.682 | 212 | 0.7089 | Homo sapiens neuron-specific protein gene |
| 127 | Hs.23111 | 1 | 0.6799 | 159 | 0.7234 | 293 | 0.6799 | Human putative tRNA synthetase-like protein mRNA |
| 128 | Hs.149923 | 1 | 0.6794 | 127 | 0.736 | 294 | 0.6794 | Human X box binding protein-1 (XBP-1) mRNA |
| 129 | Hs.188 | -1 | 0.6794 | 88 | 0.764 | 295 | 0.6794 | Human phosphodiesterase mRNA |
| 130 | Hs.85050 | -1 | 0.6794 | 150 | 0.7279 | 296 | 0.6794 | Human phospholamban mRNA |
| 131 | Hs.2471 | 1 | 0.6793 | 263 | 0.6793 | 124 | 0.7438 | Human mRNA for KIAA0020 gene |
| 132 | Hs.334 | -1 | 0.6788 | 188 | 0.7081 | 298 | 0.6788 | Human guanine nucleotide regulatory protein (tim1) mRNA |
| 133 | Hs.159608 | -1 | 0.6784 | 266 | 0.6784 | 156 | 0.7293 | Human microsomal aldehyde dehydrogenase (ALD10) mRNA |
| 134 | Hs.183752 | -1 | 0.6767 | 270 | 0.6775 | 310 | 0.6767 | Human prostatic secretory protein 57 mRNA |
| 135 | Hs.62661 | -1 | 0.6751 | 105 | 0.7477 | 319 | 0.6751 | Human guanylate binding protein isoform I (GBP-2) mRNA |
| 136 | Hs.172153 | -1 | 0.6748 | 274 | 0.6748 | 68 | 0.7798 | Human plasma (extracellular) mRNA for glutathione peroxidase |
| 137 | Hs.184298 | 1 | 0.6748 | 277 | 0.6748 | 248 | 0.6939 | |
| 138 | Hs.106880 | 1 | 0.6745 | 168 | 0.7189 | 321 | 0.6745 | Homo sapiens bystin mRNA |
| 139 | Hs.76688 | -1 | 0.6735 | 29 | 0.8342 | 325 | 0.6735 | Human carboxylesterase mRNA |
| 140 | Hs.155545 | -1 | 0.6735 | 225 | 0.6919 | 326 | 0.6735 | Human p37NB mRNA |
| 141 | Hs.155418 | -1 | 0.6729 | 34 | 0.8153 | 329 | 0.6729 | Human cancellous bone osteoblast mRNA for GS3955 |
| 142 | Hs.0 | -1 | 0.6724 | 271 | 0.6766 | 333 | 0.6724 | Homo sapiens ubiquitin-activating enzyme E1 related protein mRNA |
| 143 | Hs.84113 | 1 | 0.6721 | 288 | 0.6721 | 38 | 0.8083 | Homo sapiens protein tyrosine phosphatase (CIP2)mRNA |
| 144 | Hs.118625 | -1 | 0.6721 | 290 | 0.6721 | 179 | 0.718 | Human hexokinase 1 (HK1) mRNA |

FIG. 6e

| 145 | Hs.81875 | -1 | 0.6713 | 84 | 0.7676 | 341 | 0.6713 | Human mRNA for KIAA0207 gene |
| --- | --- | --- | --- | --- | --- | --- | --- | --- |
| 146 | Hs.1827 | -1 | 0.6712 | 293 | 0.6712 | 158 | 0.7277 | Human nerve growth factor receptor mRNA |
| 147 | Hs.239926 | -1 | 0.6712 | 297 | 0.6712 | 18 | 0.8373 | Human methyl sterol oxidase (ERG25) mRNA |
| 148 | Hs.366 | 1 | 0.6703 | 298 | 0.6703 | 256 | 0.6917 | Human mRNA for 6-pyruvoyl-tetrahydropterin synthase |
| 149 | Hs.81343 | 1 | 0.6703 | 302 | 0.6703 | 84 | 0.768 | Human mRNA for pro-alpha 1 (II) collagen 3' end C-term. triple helical |
| 150 | Hs.80986 | 1 | 0.6702 | 73 | 0.7757 | 343 | 0.6702 | |
| 151 | Hs.23311 | -1 | 0.6694 | 304 | 0.6694 | 82 | 0.7685 | Human mRNA for KIAA0367 gene |
| 152 | Hs.78864 | 1 | 0.6692 | 80 | 0.7721 | 351 | 0.6692 | Human IgG low affinity Fc fragment receptor (FcRIIa) mRNA |
| 153 | Hs.22785 | -1 | 0.6681 | 190 | 0.7072 | 357 | 0.6681 | Human GABA-A receptor epsilon subunit mRNA |
| 154 | Hs.249495 | 1 | 0.6681 | 114 | 0.7432 | 358 | 0.6681 | H.sapiens mRNA for hnRNPcore protein A1. |
| 155 | Hs.114346 | -1 | 0.6676 | 313 | 0.6676 | 90 | 0.7648 | Human cytochrome c oxidase subunit VIIa (COX7A) muscle isoform mRNA |
| 156 | Hs.78991 | -1 | 0.6676 | 314 | 0.6676 | 205 | 0.7105 | Human GS1 (protein of unknown function) mRNA |
| 157 | Hs.173724 | -1 | 0.6676 | 315 | 0.6676 | 108 | 0.7546 | Human creatine kinase-B mRNA |
| 158 | Hs.19368 | -1 | 0.6676 | 170 | 0.7189 | 363 | 0.6676 | Human matrilin-2 precursor mRNA |
| 159 | Hs.156346 | 1 | 0.6667 | 322 | 0.6667 | 53 | 0.7895 | Human DNA topoisomerase II (top2) mRNA |
| 160 | Hs.0 | 1 | 0.6667 | 323 | 0.6667 | 135 | 0.7368 | Human estrogen receptor-related protein (hERRa1) mRNA |
| 161 | Hs.89643 | 1 | 0.6667 | 325 | 0.6667 | 337 | 0.6724 | Homo sapiens transketolase (tk) mRNA |
| 162 | Hs.183487 | 1 | 0.6649 | 331 | 0.6649 | 269 | 0.689 | Human HEM45 mRNA |
| 163 | Hs.182825 | 1 | 0.6638 | 126 | 0.7387 | 379 | 0.6638 | Human ribosomal protein L35 mRNA |
| 164 | Hs.34789 | 1 | 0.6631 | 338 | 0.6631 | 96 | 0.7599 | Human mRNA for KIAA0115 gene |
| 165 | Hs.79276 | -1 | 0.6631 | 339 | 0.6631 | 359 | 0.6676 | Human mRNA for KIAA0232 gene |
| 166 | Hs.171921 | -1 | 0.6627 | 337 | 0.6631 | 380 | 0.6627 | Human mRNA for semaphorin E |
| 167 | Hs.77311 | -1 | 0.6622 | 107 | 0.7468 | 384 | 0.6622 | Human mRNA for tob family |
| 168 | Hs.80617 | 1 | 0.6622 | 347 | 0.6622 | 200 | 0.7127 | Human ribosomal protein S16 mRNA |
| 169 | Hs.101850 | -1 | 0.6617 | 307 | 0.6694 | 386 | 0.6617 | Human cellular retinol-binding protein mRNA |
| 170 | Hs.153863 | -1 | 0.6617 | 242 | 0.6847 | 387 | 0.6617 | Human chromosome 15 Mad homolog Smad6 mRNA |
| 171 | Hs.74598 | 1 | 0.6613 | 349 | 0.6613 | 291 | 0.6805 | Human DNA polymerase delta small subunit mRNA |
| 172 | Hs.184270 | 1 | 0.6613 | 350 | 0.6613 | 338 | 0.6719 | Human capping protein alpha subunit isoform 1 mRNA |
| 173 | Hs.36508 | -1 | 0.6613 | 351 | 0.6613 | 194 | 0.7148 | Human beige protein homolog (chs) mRNA |
| 174 | Hs.76927 | 1 | 0.6611 | 182 | 0.7108 | 389 | 0.6611 | Human putative outer mitochondrial membrane 34 kDa translocase hTOM34 mRNA |

FIG. 6f

| 175 | Hs.76194 | 1 | 0.6606 | 32 | 0.8216 | 391 | 0.6606 | Human ribosomal protein S5 mRNA |
|---|---|---|---|---|---|---|---|---|
| 176 | Hs.142827 | -1 | 0.6604 | 355 | 0.6604 | 316 | 0.6756 | Human P311 HUM -3.1 mRNA |
| 177 | Hs.88778 | -1 | 0.6595 | 245 | 0.6838 | 396 | 0.6595 | Human carbonyl reductase mRNA |
| 178 | Hs.182979 | 1 | 0.6595 | 276 | 0.6748 | 397 | 0.6595 | Human ribosomal protein L12 mRNA |
| 179 | Hs.93002 | 1 | 0.6595 | 361 | 0.6595 | 150 | 0.7309 | Human cyclin-selective ubiquitin carrier protein mRNA |
| 180 | Hs.182018 | 1 | 0.659 | 252 | 0.682 | 402 | 0.659 | Homo sapiens interleukin-1 receptor-associated kinase (IRAK) mRNA |
| 181 | Hs.83734 | -1 | 0.6586 | 364 | 0.6586 | 315 | 0.6756 | Human syntaxin mRNA |
| 182 | Hs.1119 | 1 | 0.6579 | 275 | 0.6748 | 408 | 0.6579 | Human mRNA for TR3beta |
| 183 | Hs.724 | -1 | 0.6579 | 346 | 0.6622 | 410 | 0.6579 | Human triiodothyronine (ear7) mRNA |
| 184 | Hs.173063 | -1 | 0.6577 | 367 | 0.6577 | 30 | 0.819 | Human transducin-like enhancer protein (TLE2) mRNA |
| 185 | Hs.127376 | -1 | 0.6574 | 318 | 0.6667 | 412 | 0.6574 | Human mRNA for KIAA0266 gene |
| 186 | Hs.274313 | -1 | 0.6574 | 208 | 0.6991 | 415 | 0.6574 | Human insulin-like growth factor binding protein 6 (IGFBP6) mRNA |
| 187 | Hs.50964 | -1 | 0.6563 | 165 | 0.7198 | 421 | 0.6563 | Human mRNA for transmembrane carcinoembryonic antigen BGPa (formerly TM1-CEA) |
| 188 | Hs.418 | 1 | 0.6559 | 376 | 0.6559 | 79 | 0.7712 | Human fibroblast activation protein mRNA |
| 189 | Hs.84728 | -1 | 0.655 | 379 | 0.655 | 143 | 0.7347 | Human mRNA for GC-Box binding protein BTEB2 |
| 190 | Hs.21365 | -1 | 0.6547 | 344 | 0.6622 | 425 | 0.6547 | Human mRNA for nucleosome assembly protein |
| 191 | Hs.307164 | -1 | 0.6547 | 161 | 0.7225 | 428 | 0.6547 | Human 3' |
| 192 | Hs.37682 | -1 | 0.6541 | 388 | 0.6541 | 130 | 0.7411 | Human tazarotene-induced gene 2 (TIG2) mRNA |
| 193 | Hs.290 | -1 | 0.6523 | 393 | 0.6523 | 169 | 0.7223 | Human Ca2+-dependent phospholipase A2 mRNA |
| 194 | Hs.79265 | -1 | 0.6523 | 394 | 0.6523 | 122 | 0.7454 | Human p126 (ST5) mRNA |
| 195 | Hs.278338 | -1 | 0.6515 | 387 | 0.6541 | 441 | 0.6515 | Human LGN protein mRNA |
| 196 | Hs.86724 | 1 | 0.6514 | 399 | 0.6514 | 189 | 0.7159 | Human GTP cyclohydrolase I mRNA |
| 197 | Hs.77899 | -1 | 0.6514 | 402 | 0.6514 | 34 | 0.8147 | Human tropomyosin mRNA |
| 198 | Hs.95140 | -1 | 0.6505 | 404 | 0.6505 | 286 | 0.6815 | Human mRNA for KIAA0189 gene |
| 199 | Hs.171501 | -1 | 0.6505 | 406 | 0.6505 | 373 | 0.6649 | Human putative ubiquitin C-terminal hydrolase (UHX1) mRNA |
| 200 | Hs.77256 | 1 | 0.6505 | 407 | 0.6505 | 21 | 0.8298 | Human enhancer of zeste homolog 2 (EZH2) mRNA |

FIG. 6g

BIOMARKERS DOWNREGULATED IN PROSTATE CANCER

RELATED APPLICATIONS

The present application claims priority to U.S. provisional Application No. 60/976,791, filed Oct. 1, 2007 and is a continuation-in-part of U.S application Ser. No. 12/025,724, filed Feb. 4, 2008, which claims priority to 60/888,070, filed Feb. 2, 2007, and is a continuation-in-part of U.S. application Ser. No. 11/274,931, filed Nov. 14, 2005, now abandoned, which claims priority to each of U.S. Provisional Applications No. 60/627,626, filed Nov. 12, 2004, and No. 60/651,340, filed Feb. 9, 2005.

This application is related to, but does not claim the priority of U.S. patent application Ser. No. 10/057,849, now issued as U.S. Pat. No. 7,117,188, which claims priority to each of U.S. Provisional Applications No. 60/263,696, filed Jan. 24, 2001, No. 60/298,757, filed Jun. 15, 2001, and No. 60/275,760, filed Mar. 14, 2001, applications Ser. Nos. 09/633,410, filed Aug. 7, 2000, now issued as U.S. Pat. No. 6,882,990, which claims priority to each of U.S. Provisional Applications No. 60/161,806, filed Oct. 27, 1999, No. 60/168,703, filed Dec. 2, 1999, No. 60/184,596, filed Feb. 24, 2000, No. 60/191,219, filed Mar. 22, 2000, and No. 60/207,026, filed May 25, 2000. Each of the above cited applications and patents is incorporated herein by reference.

FIELD OF THE INVENTION

The present invention relates to the use of learning machines to identify relevant patterns in datasets containing large quantities of gene expression data, and more particularly to biomarkers so identified for use in screening, predicting, and monitoring prostate cancer.

BACKGROUND OF THE INVENTION

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. In particular, methods are needed for identifying patterns in biological systems as reflected in gene expression data.

A significant percentage of men (20%) in the U.S. are diagnosed with prostate cancer during their lifetime, with nearly 300,000 men diagnosed annually, a rate second only to skin cancer. However, only 3% of those die of the disease. About 70% of all diagnosed prostate cancers occur in men aged 65 years and older. Many prostate cancer patients have undergone aggressive treatments that can have life-altering side effects such as incontinence and sexual dysfunction. It is believed that a substantial portion of the cancers are overtreated. Currently, most early prostate cancer identification is done using prostate-specific antigen (PSA) screening, but few indicators currently distinguish between progressive prostate tumors that may metastasize and escape local treatment and indolent cancers of benign prostate hyperplasia (BPH). Further, some studies have shown that PSA is a poor predictor of cancer, instead tending to predict BPH, which requires no or little treatment.

There is an urgent need for new biomarkers for distinguishing between normal, benign and malignant prostate tissue and for predicting the size and malignancy of prostate cancer. Blood serum biomarkers, or biomarkers found in semen, would be particularly desirable for screening prior to biopsy, however, evaluation of gene expression microarrays from biopsied prostate tissue is also useful.

SUMMARY OF THE INVENTION

Gene expression data are analyzed using learning machines such as support vector machines (SVM) and ridge regression classifiers to rank genes according to their ability to separate prostate cancer from other prostate conditions including BPH and normal. Genes are identified that individually provide sensitivities and selectivities of better than 80% and, when combined in small groups, 90%, for separating prostate cancer from other prostate conditions.

An exemplary embodiment comprises methods and systems for detecting genes involved with prostate cancer and determination of methods and compositions for treatment of prostate cancer. In one embodiment, to improve the statistical significance of the results, supervised learning techniques can analyze data obtained from a number of different sources using different microarrays, such as the Affymetrix U95 and U133A GeneChip® chip sets.

BRIEF DESCRIPTION OF THE DRAWINGS

FIGS. 4a-4d combined are a table showing the ranking of the top 200 genes for separating prostate tumor from other tissues.

FIGS. 5a-5o combined are two tables showing the top 200 genes for separating prostate cancer from all other tissues that were identified in each of the 2001 study and the 2003 study.

FIG. 6a-6g combined are a table showing the top 200 genes for separating G3 and G4 tumor versus others using feature ranking by consensus between the 2001 study and the 2003 study.

DETAILED DESCRIPTION OF THE PREFERRED EMBODIMENT

Figure 1:
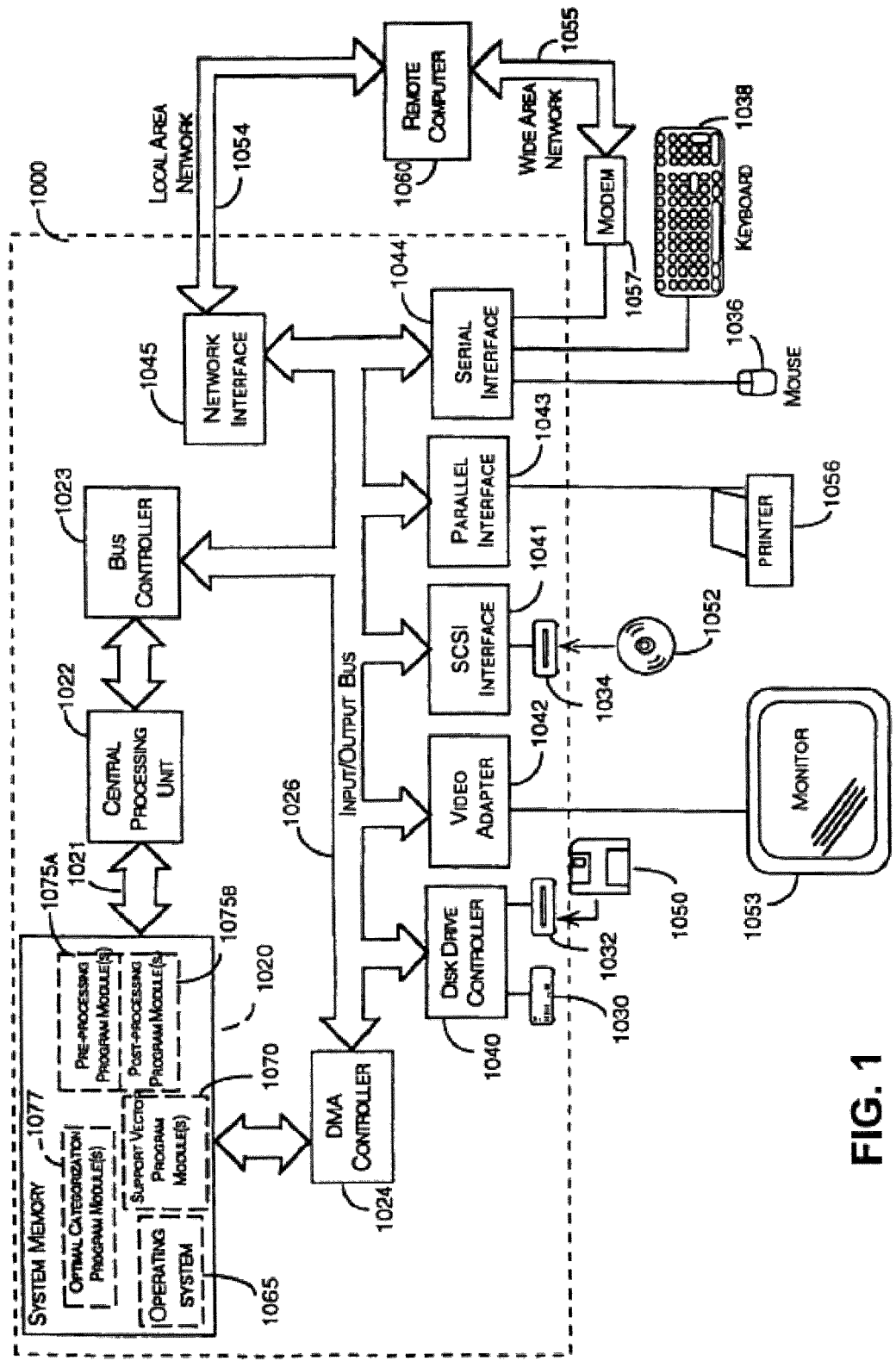
FIG. 1 is a functional block diagram illustrating an exemplary operating environment for an embodiment of the present invention.

The present invention utilizes learning machine techniques, including support vector machines and ridge regression, to discover knowledge from gene expression data obtained by measuring hybridization intensity of gene and gene fragment probes on microarrays. The knowledge so discovered can be used for diagnosing and prognosing changes in biological systems, such as diseases. Preferred embodiments comprise identification of genes that will distinguish between different types of prostate disorders, such as benign prostate hyperplasy and cancer, and normal, and use of such information for decisions on treatment of patients with prostate disorders.

For purposes of the present invention, "gene" refers to the gene expression products, including proteins, corresponding to genes, gene fragments, ESTs and olionucleotides that are included on the Affymetrix microarrays used in the tests described in the examples. Identification of a gene by a GeneBank accession number (GAN), Unigene No. and/or gene name constitutes an express incorporation by reference of the record corresponding to that identifier in the National Center for Biotechnology Information (NCBI) databases, which is publicly accessible and well known to those of skill in the art.

The problem of selection of a small amount of data from a large data source, such as a gene subset from a microarray, is particularly solved using the methods described herein. Preferred methods described herein use support vector machine (SVM) methods based and recursive feature elimination (RFE), which is described in detail in U.S. Pat. No. 7,117,188, which is incorporated by reference. (It should be noted that "RFE-SVM" and "SVM-RFE" may be used interchangeably throughout the detailed description, however, both refer to the same technique.) In examining gene expression data to find determinative genes, these methods eliminate gene redundancy automatically and yield better and more compact gene subsets.

The data is input into computer system programmed for executing an algorithm using a learning machine for performing a feature selection and/or ranking, preferably a SVM-RFE. The SVM-RFE is run one or more times to generate the best feature selections, which can be displayed in an observation graph or listed in a table or other display format. (Examples of listings of selected features (in this case, genes) are included in many of the tables below.) The SVM may use any algorithm and the data may be preprocessed and postprocessed if needed. Preferably, a server contains a first observation graph that organizes the results of the SVM activity and selection of features.

The information generated by the SVM may be examined by outside experts, computer databases, or other complementary information sources. For example, if the resulting feature selection information is about selected genes, biologists or experts or computer databases may provide complementary information about the selected genes, for example, from medical and scientific literature. Using all the data available, the genes are given objective or subjective grades. Gene interactions may also be recorded.

FIG. 1 and the following discussion are intended to provide a brief and general description of a suitable computing environment for implementing biological data analysis according to the present invention. Although the system shown in FIG. 1 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm. Furthermore, optimal categorization program modules 1077 may comprise computer-executable instructions for optimally categorizing a data set.

The computer 1000 may operate in a networked environment using logical connections to one or more remote computers, such as remote computer 1060. The remote computer 1060 may be a server, a router, a peer to peer device or other common network node, and typically includes many or all of the elements described in connection with the computer 1000. In a networked environment, program modules and data may be stored on the remote computer 1060. Appropriate logical connections include a local area network ("LAN") and a wide area network ("WAN"). In a LAN environment, a network interface, such as an Ethernet adapter card, can be used to connect the computer to the remote computer. In a WAN environment, the computer may use a telecommunications device, such as a modem, to establish a connection. It will be appreciated that the network connections shown are illustrative and other devices of establishing a communications link between the computers may be used.

A preferred selection browser is preferably a graphical user interface that would assist final users in using the generated information. For example, in the examples herein, the selection browser is a gene selection browser that assists the final user in selection of potential drug targets from the genes identified by the SVM RFE. The inputs are the observation graph, which is an output of a statistical analysis package and any complementary knowledge base information, preferably in a graph or ranked form. For example, such complementary information for gene selection may include knowledge about the genes, functions, derived proteins, measurement assays, isolation techniques, etc. The user interface preferably allows for visual exploration of the graphs and the product of the two graphs to identify promising targets. The browser does not generally require intensive computations and if needed, can be run on other computer means. The graph generated by the server can be precomputed, prior to access by the browser, or is generated in situ and functions by expanding the graph at points of interest.

In a preferred embodiment, the server is a statistical analysis package, and in the gene feature selection, a gene selection server. For example, inputs are patterns of gene expression, from sources such as DNA microarrays or other data sources. Outputs are an observation graph that organizes the results of one or more runs of SVM RFE. It is optimum to have the selection server run the computationally expensive operations.

A preferred method of the server is to expand the information acquired by the SVM. The server can use any SVM results, and is not limited to SVM RFE selection methods. As an example, the method is directed to gene selection, though any data can be treated by the server. Using SVM RFE for gene selection, gene redundancy is eliminated, but it is informative to know about discriminant genes that are correlated with the genes selected. For a given number N of genes, only one combination is retained by SVM-RFE. In actuality, there are many combinations of N different genes that provide similar results.

A combinatorial search is a method allowing selection of many alternative combinations of N genes, but this method is prone to overfitting the data. SVM-RFE does not overfit the data. SVM-RFE is combined with supervised clustering to provide lists of alternative genes that are correlated with the optimum selected genes. Mere substitution of one gene by another correlated gene yields substantial classification performance degradation.

The examples included herein show preferred methods for determining the genes that are most correlated to the presence of cancer or can be used to predict cancer occurance in an individual. There is no limitation to the source of the data and the data can be combinations of measurable criteria, such as genes, proteins or clinical tests, that are capable of being used to differentiate between normal conditions and changes in conditions in biological systems.

In the following examples, preferred numbers of genes were determined that result from separation of the data that discriminate. These numbers are not limiting to the methods of the present invention. Preferably, the preferred optimum number of genes is a range of approximately from 1 to 500, more preferably, the range is from 10 to 250, from 1 to 50, even more preferably the range is from 1 to 32, still more preferably the range is from 1 to 21 and most preferably, from 1 to 10. The preferred optimum number of genes can be affected by the quality and quantity of the original data and thus can be determined for each application by those skilled in the art.

Once the determinative genes are found by the learning machines of the present invention, methods and compositions for treatments of the biological changes in the organisms can be employed. For example, for the treatment of cancer, therapeutic agents can be administered to antagonize or agonize, enhance or inhibit activities, presence, or synthesis of the gene products. Therapeutic agents and methods include, but are not limited to, gene therapies such as sense or antisense polynucleotides, DNA or RNA analogs, pharmaceutical agents, plasmaphoresis, antiangiogenics, and derivatives, analogs and metabolic products of such agents.

Such agents may be administered via parenteral or noninvasive routes. Many active agents are administered through parenteral routes of administration, intravenous, intramuscular, subcutaneous, intraperitoneal, intraspinal, intrathecal, intracerebroventricular, intraarterial and other routes of injection. Noninvasive routes for drug delivery include oral, nasal, pulmonary, rectal, buccal, vaginal, transdermal and occular routes.

The following examples illustrate the results of using SVMs and other learning machines to identify genes associated with disorders of the prostate. Such genes may be used for diagnosis, treatment, in terms of identifying appropriate therapeutic agents, and for monitoring the progress of treatment.

The analyses described in the following examples were conducted using different datasets provided by Dr. Thomas A. Stamey at Stanford University, the first in 2001 using Affymetrix HuGeneFL probe arrays ("Stamey01"), the second in 2003 using the Affymetrix U133A GENECHIP® microarray ("Stamey03"). The basic details for these datasets are summarized below:

| DATASET | AFFYMETRIX CHIP | # OF PROBES | # OF SAMPLES |
|---|---|---|---|
| STAMEY01 | HuGeneFL | 7129 | 67 |
| STAMEY03 | U133A | 22,283 | 87 |

The tissue compositions used to generate the two datasets are provided in Tables 38 and 12 for Stamey03 and Stamey01, respectively.

EXAMPLE 1

Isolation of Genes Involved with Prostate Cancer

Using the methods disclosed herein, genes associated with prostate cancer were isolated. Various methods of treating and analyzing the cells, including SVM, were utilized to determine the most reliable method for analysis.

Tissues were obtained from patients that had cancer and had undergone prostatectomy. The tissues were processed according to a standard protocol of Affymetrix and gene expression values from 7129 probes on the Affymetrix HuGenFL GeneChip® were recorded for 67 tissues from 26 patients (the Stamey01 dataset).

Specialists of prostate histology recognize at least three different zones in the prostate: the peripheral zone (PZ), the central zone (CZ), and the transition zone (TZ). In this study, tissues from all three zones are analyzed because previous findings have demonstrated that the zonal origin of the tissue is an important factor influencing the genetic profiling. Most prostate cancers originate in the PZ. Cancers originating in the PZ have worse prognosis than those originating in the TZ. Contemporary biopsy strategies concentrate on the PZ and largely ignore cancer in the TZ. Benign prostate hyperplasia (BPH) is found only in the TZ. BPH is a suitable control that may be used to compare cancer tissues in genetic profiling experiments. BPH is also convenient to use as control because it is abundant and easily dissected. However, controls coming from normal tissues microdissected with lasers in the CZ and PZ can also provide important complementary controls. The gene expression profile differences have been found to be larger between PZ-G4-G5 cancer and CZ-normal used as control, compared to PZ-normal used as control. A possible explanation comes from the fact that is presence of cancer, even normal adjacent tissues have undergone DNA changes (Malins et al, 2003-2004). Table 1 gives zone properties.

TABLE 1

| Zone | Properties |
|------|------------|
| PZ | From apex posterior to base, surrounds transition and central zones. Largest zone (70% in young men). Largest number cancers (60-80%). Dysplasia and atrophy common in older men. |
| CZ | Surrounds transition zone to angle of urethra to bladder base. Second largest zone (25% in young men to 30% at 40 year old). 50% of PSA secreting epithelium. 5-20% of cancers. |
| TZ | Two pear shaped lobes surrounding the proximal urethra. Smallest zone in young men (less than 5%). Gives rise to BPH in older men. May expand to the bulk of the gland. 10-18% of cancers. Better cancer prognosis than PZ cancer. |

Classification of cancer determines appropriate treatment and helps determine a prognosis. Cancer develops progressively from an alteration in a cell's genetic structure due to mutations, to cells with uncontrolled growth patterns. Classification is made according to the site of origin, histology (or cell analysis; called grading), and the extent of the disease (called staging).

Prostate cancer specialists classify cancer tissues according to grades, called Gleason grades, which are correlated with the malignancy of the diseases. The larger the grade, the worse the prognosis (chance of survival). In this study, tissues of grade 3 and above are used. Grades 1 and 2 are more difficult to characterize with biopsies and not very malignant. Grades 4 and 5 are not very differentiated and correspond to the most malignant cancers: for every 10% increase in the percent of grade 4/5 tissue found, there is a concomitant increase in post radical prostatectomy failure rate. Each grade is defined in Table 2.

TABLE 2

| Grade | Description |
|-------|-------------|
| 1 | Single, separate, uniform, round glands closely packed with a definite rounded edge limiting the area of the tumor. Separation of glands at the periphery from the main collection by more than one gland diameter indicates a component of at least grade 2. Uncommon pattern except in the TZ. Almost never seen in needle biopsies. |
| 2 | Like grade 1 but more variability in gland shape and more stroma separating glands. Occasional glands show angulated or distorted contours. More common in TZ than PZ. Pathologists don't diagnose Gleason grades 1 or 2 on prostate needle biopsies since they are uncommon in the PZ, there is inter-pathologist variability and poor correlation with radical prostatectomy. |
| 3 | G3 is the most commonly seen pattern. Variation in size, shape (may be angulated or compressed), and spacing of glands (may be separated by >1 gland diameter). Many small glands have occluded or abortive lumens (hollow areas). There is no evidence of glandular fusion. The malignant glands infiltrate between benign glands. |
| 4 | The glands are fused and there is no intervening stroma. |
| 5 | Tumor cells are arranged in solid sheets with no attempts at gland formation. The presence of Gleason grade 5 and high percent carcinoma at prostatectomy predicts early death. |

Staging is the classification of the extent of the disease. There are several types of staging methods. The tumor, node, metastases (TNM) system classifies cancer by tumor size (T), the degree of regional spread or lymph node involvement (N), and distant metastasis (M). The stage is determined by the size and location of the cancer, whether it has invaded the prostatic capsule or seminal vesicle, and whether it has metastasized. For staging, MRI is preferred to CT because it permits more accurate T staging. Both techniques can be used in N staging, and they have equivalent accuracy. Bone scintigraphy is used in M staging.

The grade and the stage correlate well with each other and with the prognosis. Adenocarcinomas of the prostate are given two grade based on the most common and second most common architectural patterns. These two grades are added to get a final score of 2 to 10. Cancers with a Gleason score of <6 are generally low grade and not aggressive.

The samples collected included tissues from the Peripheral Zone (PZ); Central Zone (CZ) and Transition Zone (TZ). Each sample potentially consisted of four different cell types: Stomal cells (from the supporting tissue of the prostate, not participating in its function); Normal organ cells; Benign prostatic hyperplasia cells (BPH); Dysplasia cells (cancer precursor stage) and Cancer cells (of various grades indicating the stage of the cancer). The distribution of the samples in Table 3 reflects the difficulty of obtaining certain types of tissues:

TABLE 3

|    | Stroma | Normal | BPH | Dysplasia | Cancer G3 | Cancer G4 | G3 + G4 |
|----|--------|--------|-----|-----------|-----------|-----------|---------|
| PZ | 1      | 5      |     | 3         | 10        | 24        | 3       |
| CZ |        | 3      |     |           |           |           |         |
| TZ |        |        | 18  |           |           |           |         |

Benign Prostate Hyperplasia (BPH), also called nodular prostatic hyperplasia, occurs frequently in aging men. By the eighth decade, over 90% of males will have prostatic hyperplasia. However, in only a minority of cases (about 10%) will this hyperplasia be symptomatic and severe enough to require surgical or medical therapy. BPH is not a precursor to carcinoma.

It has been argued in the medical literature that TZ BPH could serve as a good reference for PZ cancer. The highest grade cancer (G4) is the most malignant. Part of these experiments are therefore directed towards the separation of BPH vs. G4.

Some of the cells were prepared using laser confocal microscopy (LCM which was used to eliminate as much of the supporting stromal cells as possible and provides purer samples.

Gene expression was assessed from the presence of mRNA in the cells. The mRNA is converted into cDNA and amplified, to obtain a sufficient quantity. Depending on the amount of mRNA that can be extracted from the sample, one or two amplifications may be necessary. The amplification process may distort the gene expression pattern. In the data set under study, either 1 or 2 amplifications were used. LCM data always required 2 amplifications. The treatment of the samples is detailed in Table 4.

TABLE 4

|        | 1 amplification | 2 amplifications |
|--------|-----------------|------------------|
| No LCM | 33              | 14               |
| LCM    |                 | 20               |

The end result of data extraction is a vector of 7129 gene expression coefficients.

Gene expression measurements require calibration. A probe cell (a square on the array) contains many replicates of the same oligonucleotide (probe) that is a 25 bases long sequence of DNA. Each "perfect match" (PM) probe is designed to complement a reference sequence (piece of gene). It is associated with a "mismatch" (MM) probe that is identical except for a single base difference in the central position. The chip may contain replicates of the same PM probe at different positions and several MM probes for the same PM probe corresponding to the substitution of one of the four bases. This ensemble of probes is referred to as a probe set. The gene expression is calculated as:

$$\text{Average Difference} = 1/\text{pair num} \Sigma_{probe\ set}(PM-MM)$$

If the magnitude of the probe pair values is not sufficiently contrasted, the probe pair is considered dubious. Thresholds are set to accept or reject probe pairs. Affymetrix considers samples with 40% or over acceptable probe pairs of good quality. Lower quality samples can also be effectively used with the SVM techniques.

A simple "whitening" was performed as pre-processing, so that after pre-processing, the data matrix resembles "white noise". In the original data matrix, a line of the matrix represented the expression values of 7129 genes for a given sample (corresponding to a particular combination of patient/tissue/preparation method). A column of the matrix represented the expression values of a given gene across the 67 samples. Without normalization, neither the lines nor the columns can be compared. There are obvious offset and scaling problems. The samples were pre-processed to: normalize matrix columns; normalize matrix lines; and normalize columns again. Normalization consists of subtracting the mean and dividing by the standard deviation. A further normalization step was taken when the samples are split into a training set and a test set.

The mean and variance column-wise was computed for the training samples only. All samples (training and test samples) were then normalized by subtracting that mean and dividing by the standard deviation.

Samples were evaluated to determine whether LCM data preparation yields more informative data than unfiltered tissue samples and whether arrays of lower quality contain useful information when processed using the SVM technique.

Two data sets were prepared, one for a given data preparation method (subset 1) and one for a reference method (subset 2). For example, method 1=LCM and method 2=unfiltered samples. Golub's linear classifiers were then trained to distinguish between cancer and normal cases using subset 1 and another classifier using subset 2. The classifiers were then tested on the subset on which they had not been trained (classifier 1 with subset 2 and classifier 2 with subset 1).

If classifier 1 performs better on subset 2 than classifier 2 on subset 1, it means that subset 1 contains more information to do the separation cancer vs. normal than subset 2.

The input to the classifier is a vector of n "features" that are gene expression coefficients coming from one microarray experiment. The two classes are identified with the symbols (+) and (−) with "normal" or reference samples belong to class (+) and cancer tissues to class (−). A training set of a number of patterns $\{x_1, x_2, \ldots x_k, \ldots x_l\}$ with known class labels $\{y_1, y_2, \ldots y_k, \ldots y_l\}$, $y_k \in \{-1, +1\}$, is given. The training samples are used to build a decision function (or discriminant function) D(x), that is a scalar function of an input pattern x.

New samples are classified according to the sign of the decision function:

$D(x) > 0 \Rightarrow x \in \text{class}(+)$ $D(x) < 0 \Rightarrow x \in \text{class}(-)$ $D(x) = 0$, decision boundary.

Decision functions that are simple weighted sums of the training patterns plus a bias are called linear discriminant functions.

$D(x) = w \cdot x + b$, where w is the weight vector and b is a bias value.

In the case of Golub's classifier, each weight is computed as:

$W_i = (\mu_i(+) - \mu_i(-))/(\sigma_i(+) + \sigma_i(-))$, where ($\mu_i$ and $\sigma_i$ are the mean and standard deviation of the gene expression values of gene i for all the patients of class (+) or class (−), i=1, ... n. Large positive $w_i$ values indicate strong correlation with class (+) whereas large negative $w_i$ values indicate strong correlation with class (−). Thus the weights can also be used to rank the features (genes) according to relevance. The bias is computed as $b = -w \cdot \mu$, where $\mu = (\mu(+) + \mu(-))/2$.

Golub's classifier is a standard reference that is robust against outliers. Once a first classifier is trained, the magnitude of $w_i$ is used to rank the genes. The classifiers are then retrained with subsets of genes of different sizes, including the best ranking genes.

To assess the statistical significance of the results, ten random splits of the data including samples were prepared from either preparation method and submitted to the same method. This allowed the computation of an average and standard deviation for comparison purposes.

Tissue from the same patient was processed either directly (unfiltered) or after the LCM procedure, yielding a pair of microarray experiments. This yielded 13 pairs, including: four G4; one G3+4; two G3; four BPH; one CZ (normal) and one PZ (normal).

For each data preparation method (LCM or unfiltered tissues), the tissues were grouped into two subsets:

Cancer=G4+G3(7 cases)

Normal=BPH+CZ+PZ(6 cases).

Figure 2:
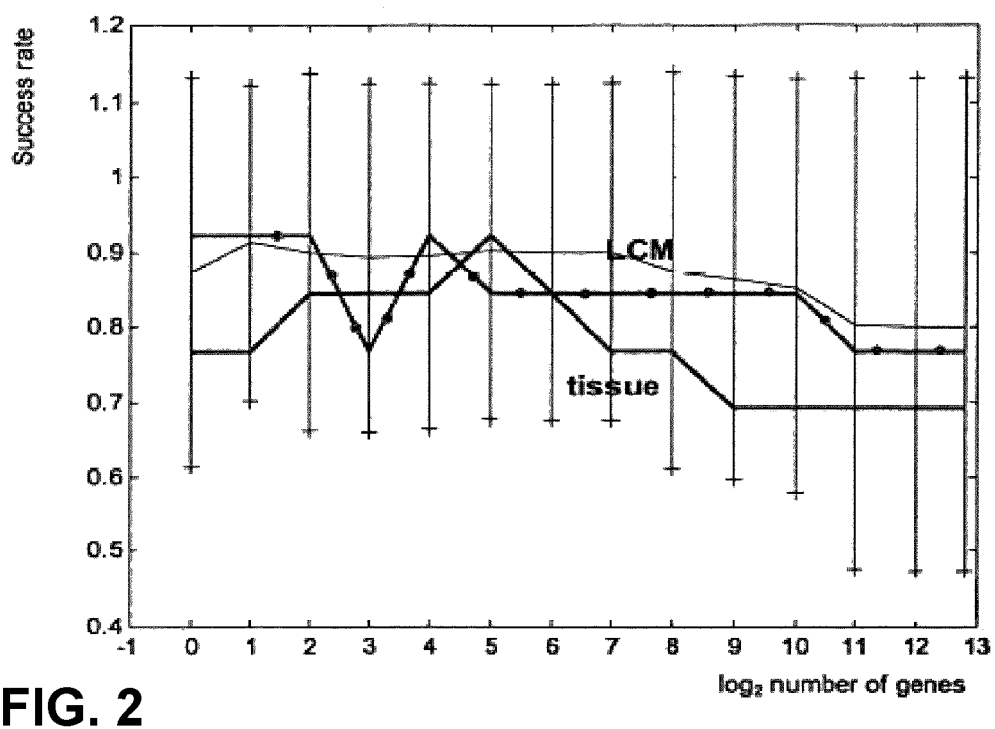
FIG. 2 is a plot showing the results based on LCM data preparation for prostate cancer analysis.

The results are shown in FIG. 2. The large error bars are due to the small size. However, there is an indication that LCM samples are better than unfiltered tissue samples. It is also interesting to note that the average curve corresponding to random splits of the data is above both curves. This is not surprising since the data in subset 1 and subset 2 are differently distributed. When making a random split rather than segregating samples, both LCM and unfiltered tissues are represented in the training and the test set and performance on the test set are better on average.

The same methods were applied to determine whether microarrays with gene expression data rejected by the Affymetrix quality criterion contained useful information by focusing on the problem of separating BPH tissue vs. G4 tissue with a total of 42 arrays (18 BPH and 24 G4).

The Affymetrix criterion identified 17 good quality arrays, 8 BPH and 9 G4. Two subsets were formed:

Subset1="good" samples, 8 BPH+9 G4

Subset2="mediocre" samples, 10 BPH+15 G4

For comparison, all of the samples were lumped together and 10 random subset 1 containing 8 BPH+9 G4 of any quality were selected. The remaining samples were used as subset 2 allowing an average curve to be obtained. Additionally the subsets were inverted with training on the "mediocre" examples and testing on the "good" examples.

When the mediocre samples are trained, perfect accuracy on the good samples is obtained, whereas training on the good examples and testing on the mediocre yield substantially worse results.

All the BPH and G4 samples were divided into LCM and unfiltered tissue subsets to repeat similar experiments as in the previous Section:

Subset1=LCM samples(5 BPH+6 LCM)

Subset2=unfiltered tissue samples(13 BPH+18 LCM)

There, in spite of the difference in sample size, training on LCM data yields better results. In spite of the large error bars, this is an indication that the LCM data preparation method might be of help in improving sample quality.

BPH vs. G4

The Affymetrix data quality criterion were irrelevant for the purpose of determining the predictive value of particular genes and while the LCM samples seemed marginally better than the unfiltered samples, it was not possible to determine a statistical significance. Therefore, all samples were grouped together and the separation BPH vs. G4 with all 42 samples (18 BPH and 24 G4) was preformed.

To evaluate performance and compare Golub's method with SVMs, the leave-one-out method was used. The fraction of successfully classified left-out examples gives an estimate of the success rate of the various classifiers.

Figure 3:
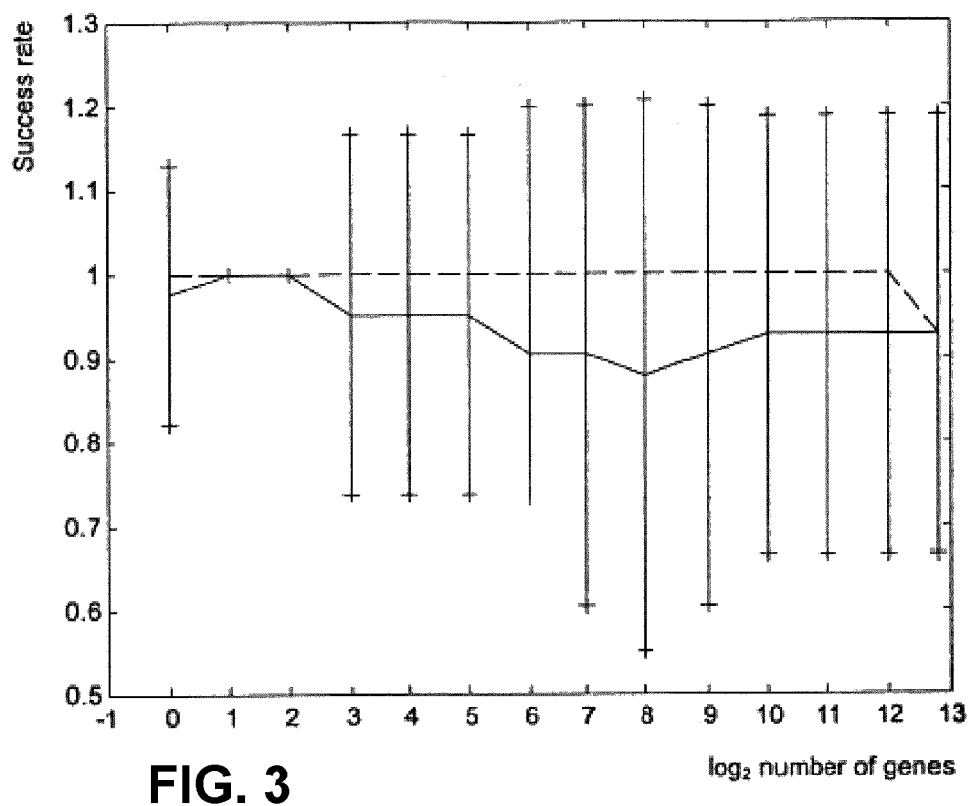
FIG. 3 is a plot graphically comparing SVM-RFE of the present invention with leave-one-out classifier for prostate cancer.

In this procedure, the gene selection process was run 41 times to obtain subsets of genes of various sizes for all 41 gene rankings. One classifier was then trained on the corresponding 40 genes for every subset of genes. This leave-one-out method differs from the "naive" leave-one-out that consists of running the gene selection only once on all 41 examples and then training 41 classifiers on every subset of genes. The naive method gives overly optimistic results because all the examples are used in the gene selection process, which is like "training on the test set". The increased accuracy of the first method is illustrated in FIG. 3. The method used in the figure is RFE-SVM and the classifier used is an SVM. All SVMs are linear with soft margin parameters C=100 and t=$10^{14}$. The dashed line represents the "naive" leave-one-out (LOO), which consists in running the gene selection once and performing loo for classifiers using subsets of genes thus derived, with different sizes. The solid line represents the more computationally expensive "true" LOO, which consists in running the gene selection 41 times, for every left out example. The left out example is classified with a classifier trained on the corresponding 40 examples for every selection of genes. If f is the success rate obtained (a point on the curve), the standard deviation is computed as sqrt(f(1−f)).

EXAMPLE 2

Analyzing Small Data Sets with Multiple Features

Small data sets with large numbers of features present several problems. In order to address ways of avoiding data overfitting and to assess the significance in performance of multivariate and univariate methods, the samples from Example 1 that were classified by Affymetrix as high quality samples were further analyzed. The samples included 8 BPH and 9 G4 tissues. Each microarray recorded 7129 gene expression values. About ⅔ of the samples in the BPH/G4 subset were considered of inadequate quality for use with standard non-SVM methods.

Simulations resulting from multiple splits of the data set of 17 examples (8 BPH and 9 G4) into a training set and a test set were run. The size of the training set is varied. For each training set drawn, the remaining data are used for testing.

For number of training examples greater than 4 and less than 16, 20 training sets were selected at random. For 16 training examples, the leave-one-out method was used, in that all the possible training sets obtained by removing 1 example at a time (17 possible choices) were created. The test set is then of size 1. Note that the test set is never used as part of the feature selection process, even in the case of the leave-one-out method.

For 4 examples, all possible training sets containing 2 examples of each class (2 BPH and 2 G4), were created and 20 of them were selected at random.

For SVM methods, the initial training set size is 2 examples, one of each class (1 BPH and 1 G4). The examples of each class are drawn at random. The performance of the LDA methods cannot be computed with only 2 examples, because at least 4 examples (2 of each class) are required to compute intraclass standard deviations. The number of training examples is incremented by steps of 2.

The top ranked genes are presented in Tables 5-8. Having determined that the SVM method provided the most compact set of features to achieve 0 leave-one-out error and that the SF-SVM method is the best and most robust method for small numbers of training examples, the top genes found by these methods were researched in the literature. Most of the genes have a connection to cancer or more specifically to prostate cancer.

Table 5 shows the top ranked genes for SF LDA using 17 best BPH/G4.

TABLE 5

| Rank | GAN | EXP | Description |
|---|---|---|---|
| 10 | X83416 | −1 | H. sapiens PrP gene |
| 9 | U50360 | −1 | Human calcium calmodulin-dependent protein kinase II gamma mRNA |
| 8 | U35735 | −1 | Human RACH1 (RACH1) mRNA |
| 7 | M57399 | −1 | Human nerve growth factor (HBNF-1) mRNA |
| 6 | M55531 | −1 | Human glucose transport-like 5 (GLUT5) mRNA |
| 5 | U48959 | −1 | Human myosin light chain kinase (MLCK) mRNA |
| 4 | Y00097 | −1 | Human mRNA for protein p68 |
| 3 | D10667 | −1 | Human mRNA for smooth muscle myosin heavy chain |
| 2 | L09604 | −1 | Homo sapiens differentiation-dependent A4 protein MRNA |
| 1 | HG1612-HT1612 | 1 | McMarcks | where GAN = Gene Acession Number;
EXP = Expression (−1 = underexpressed in cancer (G4) tissues; +1 = overexpressed in cancer tissues).

Table 6 lists the top ranked genes obtained for LDA using 17 best BPH/G4.

TABLE 6

| Rank | GAN | EXP | Description |
|---|---|---|---|
| 10 | J03592 | 1 | Human ADP/ATP translocase mRNA |
| 9 | U40380 | 1 | Human presenilin I-374 (AD3-212) mRNA |
| 8 | D31716 | −1 | Human mRNA for GC box bindig protein |
| 7 | L24203 | −1 | Homo sapiens ataxia-telangiectasia group D |
| 6 | J00124 | −1 | Homo sapiens 50 kDa type I epidermal keratin gene |
| 5 | D10667 | −1 | Human mRNA for smooth muscle myosin heavy chain |
| 4 | J03241 | −1 | Human transforming growth factor-beta 3 (TGF-beta3) MRNA |
| 3 | 017760 | −1 | Human laminin S B3 chain (LAMB3) gene |
| 2 | X76717 | −1 | H. sapiens MT-11 mRNA |
| 1 | X83416 | −1 1 | H. sapiens PrP gene |

Table 7 lists the top ranked genes obtained for SF SVM using 17 best BPH/G4.

TABLE 7

| Rank | GAN | EXP | Description |
|---|---|---|---|
| 10 | X07732 | 1 | Human hepatoma mRNA for serine protease hepsin |
| 9 | J03241 | −1 | Human transforming growth factor-beta 3 (TGF-beta3) MRNA |
| 8 | X83416 | −1 | H. sapiens PrP gene |
| 7 | X14885 | −1 | H. sapiens gene for transforming growth factor-beta 3 (TGF-beta 3) exon 1 (and joined CDS) |
| 6 | U32114 | −1 | Human caveolin-2 mRNA |
| 5 | M16938 | 1 | Human homeo-box c8 protein |
| 4 | L09604 | −1 | H. sapiens differentiation-dependent A4 protein MRNA |
| 3 | Y00097 | −1 | Human mRNA for protein p68 |
| 2 | D88422 | −1 | Human DNA for cystatin A |
| 1 | U35735 | −1 | Human RACH1 (RACH1) mRNA |

Table 8 provides the top ranked genes for SVM using 17 best BPH/G4.

TABLE 8

| Rank | GAN | EXP | Description |
|---|---|---|---|
| 10 | X76717 | −1 | H. sapiens MT-11 mRNA |
| 9 | U32114 | −1 | Human caveolin-2 mRNA |
| 8 | X85137 | 1 | H. sapiens mRNA for kinesin-related protein |
| 7 | D83018 | −1 | Human mRNA for nel-related protein 2 |
| 6 | D10667 | −1 | Human mRNA for smooth muscle myosin heavy chain |
| 5 | M16938 | 1 | Human homeo box c8 protein |
| 4 | L09604 | −1 | Homo sapiens differentiation-dependent A4 protein mRNA |
| 3 | HG1612 | 1 | McMarcks |
| 2 | M10943 | −1 | Human metallothionein-If gene (hMT-If) |
| 1 | X83416 | −1 | H. sapiens PrP gene |

Using the "true" leave-one-out method (including gene selection and classification), the experiments indicate that 2 genes should suffice to achieve 100% prediction accuracy. The two top genes were therefore more particularly researched in the literature. The results are summarized in Table 10. It is interesting to note that the two genes selected appear frequently in the top 10 lists of Tables 5-8 obtained by training only on the 17 best genes.

Table 9 is a listing of the ten top ranked genes for SVM using all 42 BPH/G4.

TABLE 9

| Rank | GAN | EXP | Description |
|---|---|---|---|
| 10 | X87613 | −1 | H. sapiens mRNA for skeletal muscle abundant |
| 9 | X58072 | −1 | Human hGATA3 mRNA for trans-acting T-cell specific |
| 8 | M33653 | −1 | Human alpha-2 type IV collagen (COL4A2) |
| 7 | S76473 | 1 | trkB [human brain mRNA] |
| 6 | X14885 | −1 | H. sapiens gene for transforming growth factor-beta 3 |
| 5 | S83366 | −1 | region centromeric to t(12; 17) brakepoint |
| 4 | X15306 | −1 | H. sapiens NF-H gene |
| 3 | M30894 | 1 | Human T-cell receptor Ti rearranged gamma-chain |

TABLE 9-continued

| Rank | GAN | EXP | Description |
|---|---|---|---|
| 2 | M16938 | 1 | Human homeo box c8 protein |
| 1 | U35735 | −1 | Human RACH1 (RACH1) mRNA |

Table 10 provides the findings for the top 2 genes found by SVM using all 42 BPH/G4. Taken together, the expression of these two genes is indicative of the severity of the disease.

TABLE 10

| GAN | Synonyms | Possible function/link to prostate cancer |
|---|---|---|
| M16938 | HOXC8 | Hox genes encode transcriptional regulatory proteins that are largely responsible for establishing the body plan of all metazoan organisms. There are hundreds of papers in PubMed reporting the role of HOX genes in various cancers. HOXC5 and HOXC8 expression are selectively turned on in human cervical cancer cells compared to normal keratinocytes. Another homeobox gene (GBX2) may participate in metastatic progression in prostatic cancer. Another HOX protein (hoxb-13) was identified as an androgen-independent gene expressed in adult mouse prostate epithelial cells. The authors indicate that this provides a new potential target for developing therapeutics to treat advanced prostate cancer |
| U35735 | Jk<br>Kidd<br>RACH1<br>RACH2<br>SLC14A1<br>UT1<br>UTE | Overexpression of RACH2 in human tissue culture cells induces apoptosis. RACH1 is downregulated in breast cancer cell line MCF-7. RACH2 complements the RAD1 protein. RAM is implicated in several cancers.<br>Significant positive lod scores of 3.19 for linkage of the Jk (Kidd blood group) with cancer family syndrome (CFS) were obtained. CFS gene(s) may possibly be located on chromosome 2, where Jk is located. |

Table 11 shows the severity of the disease as indicated by the top 2 ranking genes selected by SVMs using all 42 BPH and G4 tissues.

TABLE 11

|  | HOXC8 Underexpressed | HOXC8 Overexpressed |
|---|---|---|
| RACH1 Overexpressed | Benign | N/A |
| RACH1 Underexpressed | Grade 3 | Grade 4 |

EXAMPLE 3

Prostate Cancer Study on Affymetrix Gene Expression Data (09-2004)

A set of Affymetrix microarray GeneChip® experiments from prostate tissues were obtained from Dr. Thomas A. Stamey at Stanford University. The data from samples obtained for the prostate cancer study are summarized in Table 12 (which represents the same data as in Table 3 but organized differently.) Preliminary investigation of the data included determining the potential need for normalizations. Classification experiments were run with a linear SVM on the separation of Grade 4 tissues vs. BPH tissues. In a 32×3-fold experiment, an 8% error rate could be achieved with a selection of 100 genes using the multiplicative updates technique (similar to RFE-SVM). Performances without feature selection are slightly worse but comparable. The gene most often selected by forward selection was independently chosen in the top list of an independent published study, which provided an encouraging validation of the quality of the data.

TABLE 12

| Prostate zone | Histological classification | No. of samples |
|---|---|---|
| Central (CZ) | Normal (NL) | 9 |
|  | Dysplasia (Dys) | 4 |
|  | Grade 4 cancer (G4) | 1 |
| Peripheral (PZ) | Normal (NL) | 13 |
|  | Dysplasia (Dys) | 13 |
|  | Grade 3 cancer (G3) | 11 |
|  | Grade 4 cancer (G4) | 18 |
| Transition (TZ) | Benign Prostate Hyperplasia (BPH) | 10 |
|  | Grade 4 cancer (G4) | 8 |
| Total |  | 87 |

As controls, normal tissues and two types of abnormal tissues are used in the study: BPH and Dysplasia.

To verify the data integrity, the genes were sorted according to intensity. For each gene, the minimum intensity across all experiments was taken. The top 50 most intense values were taken. Heat maps of the data matrix were made by sorting the lines (experiments) according to zone, grade, and time processed. No correlation was found with zone or grade, however, there was a significant correlation with the time the sample was processed. Hence, the arrays are poorly normalized.

In other ranges of intensity, this artifact is not seen. Various normalization techniques were tried, but no significant improvements were obtained. It has been observed by several authors that microarray data are log-normal distributed. A qqplot of all the log of the values in the data matrix confirms that the data are approximately log-normal distributed. Nevertheless, in preliminary classification experiments, there was not a significant advantage of taking the log.

Tests were run to classify BPH vs. G4 samples. There were 10 BPH samples and 27 G4 samples. 32×3 fold experiments were performed in which the data was split into 3 subsets 32 times. Two of the subsets were used for training while the third was used for testing. The results were averaged. A feature selection was performed for each of the 32×3 data splits; the features were not selected on the entire dataset.

A linear SVM was used for classification, with ridge parameter 0.1, adjusted for each class to balance the number of samples per class. Three feature selection methods were used: (1) multiplicative updates down to 100 genes (MU100); (2) forward selection with approximate gene orthogonalisation up to 2 genes (FS2); and (3) no gene selection (NO).

The data was either raw or after taking the log (LOG). The genes were always standardized (STD: the mean over all samples is subtracted and the result is divided by the standard deviation; mean and stdev are computed on training data only, the same coefficients are applied to test data).

The results for the performances for the BPH vs. G4 separation are shown in Table 13 below, with the standard errors are shown in parentheses. "Error rate" is the average number of misclassification errors; "Balanced errate" is the average of the error rate of the positive class and the error rate of the negative class; "AUC" is the area under the ROC (receiver operating characteristic) curves that plots the sensitivity (error rate of the positive class, G4) as a function of the specificity (error rate of the negative class, BPH).

It was noted that the SVM performs quite well without feature selection, and MU 100 performs similarly, but slightly better. The number of features was not adjusted—100 was chosen arbitrarily.

TABLE 13

| Preprocessing | Feat. Select. | Error rate | Balanced errate | AUC |
|---|---|---|---|---|
| Log + STD | MU 100 | 8.09 (0.66) | 11.68 (1.09) | 98.93 (0.2) |
| Log + STD | FS 2 | 13.1 (1.1) | 15.9 (1.3) | 92.02 (1.15) |
| Log + STD | No selection | 8.49 (0.71) | 12.37 (1.13) | 97.92 (0.33) |
| STD | No selection | 8.57 (0.72) | 12.36 (1.14) | 97.74 (0.35) |

In Table 13, the good AUC and the difference between the error rate and the balanced error rate show that the bias of the classifier must be optimized to obtained a desired tradeoff between sensitivity and specificity.

Two features are not enough to match the best performances, but do quite well already.

It was determined which features were selected most often with the FS 2 method. The first gene (3480) was selected 56 times, while the second best one (5783) was selected only 7 times. The first one is believed to be relevant to cancer, while the second one has probably been selected for normalization purposes. It is interesting that the first gene (Hs.79389) is among the top three genes selected in another independent study (Febbo-Sellers, 2003).

The details of the two genes are as follows:

Gene 3480: gb:NM_006159.1/DEF=Homo sapiens nel (chicken)-like 2 (NELL2), mRNA. /FEA=mRNA / GEN=NELL2/PROD=nel (chicken)-like2/DB_XREF=gi: 5453765/UG=Hs.79389 nel (chicken)-like 2/FL=gb: D83018.1 gb:NM_006159.1

Gene 5783: gb:NM_018843.1/DEF=Homo sapiens mitochondrial carrier family protein(LOC55972), mRNA. / FEA=mRNA /GEN=LOC55972/PROD=mitochondrial carrier family protein /DB_XREF=gi: 10047121/ UG=Hs.172294 mitochondrial carrier family protein / FL=gb:NM_018843.1 gb:AF125531.1.

EXAMPLE 4

Prostate Cancer Study from Affymetrix Gene Expression Data (10-2004)

This example is a continuation of the analysis of Example 3 above on the Stamey prostate cancer microarray data. PSA has long been used as a biomarker of prostate cancer in serum, but is no longer useful. Other markers have been studied in immunohistochemical staining of tissues, including p27, Bcl-2, E-catherin and P53. However, to date, no marker has gained acceptance for use in routine clinical practice.

The gene rankings obtained correlate with those of the Febbo paper, confirming that the top ranking genes found from the Stamey data have a significant intersection with the genes found in the Febbo study. In the top 1000 genes, about 10% are Febbo genes. In comparison, a random ordering would be expected to have less than 1% are Febbo genes.

BPH is not by itself an adequate control. When selecting genes according to how well they separate grade 4 cancer tissues (G4) from BPH, one can find genes that group all non-BPH tissues with the G4 tissues (including normal, dysplasia and grade 3 tissues). However, when BPH is excluded from the training set, genes can be found that correlate well with disease severity. According to those genes, BPH groups with the low severity diseases, leading to a conclusion that BPH has its own molecular characteristics and that normal adjacent tissues should be used as controls.

TZG4 is less malignant than PZG4. It is known that TZ cancer has a better prognosis than PZ cancer. The present analysis provides molecular confirmation that TZG4 is less malignant than PZG4. Further, TZG4 samples group with the less malignant samples (grade 3, dysplasia, normal, or BPH) than with PZG4. This differentiated grouping is emphasized in genes correlating with disease progression (normal<dysplasia<g3<g4) and selected to provide good separation of TZG4 from PZG4 (without using an ordering for TZG4 and PZG4 in the gene selection criterion).

Ranking criteria implementing prior knowledge about disease malignancy are more reliable. Ranking criteria validity was assessed both with p values and with classification performance. The criterion that works best implements a tissue ordering normal<dysplasia<G3<G4 and seeks a good separation TZG4 from PZG4. The second best criterion implements the ordering normal<dysplasia<G3<TZG4<PZG4.

Comparing with other studies may help reducing the risk of overfitting. A subset of 7 genes was selected that ranked high in the present study and that of Febbo et al. 2004. Such genes yield good separating power for G4 vs. other tissues. The training set excludes BPH samples and is used both to select genes and train a ridge regression classifier. The test set includes 10 BPH and 10 G4 samples (½ from the TZ and ½ from the PZ). Success was evaluated with the area under the ROC curve ("AUC") (sensitivity vs. specificity) on test examples. AUCs between 0.96 and 1 are obtained, depending on the number of genes. Two genes are of special interest (GSTP1 and PTGDS) because they are found in semen and could be potential biomarkers that do not require the use of biopsied tissue.

The choice of the control may influence the findings (normal tissue or BPH). as may the zones from which the tissues originate. The first test sought to separate Grade 4 from BPH. Two interesting genes were identified by forward selection as gene 3480 (NELL2) and gene 5783(LOC55972). As explained in Example 3, gene 3480 is the informative gene, and it is believed that gene 5783 helps correct local on-chip variations. Gene 3480, which has Unigene cluster id. Hs.79389, is a Nel-related protein, which has been found at high levels in normal tissue by Febbo et al.

All G4 tissues seem intermixed regardless of zone. The other tissues are not used for gene selection and they all fall on the side of G4. Therefore, the genes found characterize BPH, not G4 cancer, such that it is not sufficient to use tissues of G4 and BPH to find useful genes to characterize G4 cancer.

For comparison, two filter methods were used: the Fisher criterion and the shrunken centroid criterion (Tibshirani et al, 2002). Both methods found gene 3480 to be highly informative (first or second ranking). The second best gene is 5309, which has Unigene cluster ID Hs. 100431 and is described as small inducible cytokine B subfamily (Cys-X-Cys motif). This gene is highly correlated to the first one.

The Fisher criterion is implemented by the following routine:
A vector x containing the values of a given feature for all patt_num samples
cl_num classes, k=1, 2, . . . cl_num, grouping the values of x
mu_val(k) is the mean of the x values for class k
var_val(k) is the variance of the x values for class k
patt_per_class(k) is the number of elements of class k
Unbiased_within_var is the unbiased pooled within class variance, i.e., we make a weighted average of var_val(k) with coefficients patt_per_class(k)/(patt_num--cl_num)
Unbiased_between_var=var(mu_val); % Divides by cl_num-1 then
Fisher_crit=Unbiased_between_var /Unbiased_within_ var Although the shrunken centroid criterion is somewhat more complicated than the Fisher criterion, it is quite similar. In both cases, the pooled within class variance is used to normalize the criterion. The main difference is that instead of ranking according to the between class variance (that is, the average deviation of the class centroids to the overall centroid), the shrunken centroid criterion uses the maximum deviation of any class centroid to the global centroid. In doing so, the criterion seeks features that well separate at least one class, instead of features that well separate all classes (on average).

The other small other differences are:
A fudge factor is added to Unbiased_within_std=sqrt(Unbiased_within_var) to prevent divisions by very small values. The fudge factor is computed as:
fudge=mean(Unbiased_within_std); the mean being taken over all the features.
Each class is weighted according to its number of elements cl_elem(k). The
deviation for each class is weighted by 1/sqrt(1/cl_elem(k)+1/patt_num).
Similar corrections could be applied to the Fisher criterion.

The two criteria are compared using pvalues. The Fisher criterion produces fewer false positive in the top ranked features. It is more robust, however, it also produces more redundant features. It does not find discriminant features for the classes that are least abundant or hardest to separate.

Also for comparison, the criterion of Golub et al., also known as signal to noise ratio, was used. This criterion is used in the Febbo paper to separate tumor vs. normal tissues. On this data that the Golub criterion was verified to yield a similar ranking as the Pearson correlation coefficient. For simplicity, only the Golub criterion results are reported. To mimic the situation, three binary separations were run: (G3+4 vs. all other tissues), (G4 vs. all other tissues), and (G4 vs. BPH). As expected, the first gene selected for the G4 vs. BPH is 3480, but it does not rank high in the G3+4 vs. all other and G4 vs. all other.

Compared to a random ranking, the genes selected using the various criteria applied are enriched in Febbo genes, which cross-validates the two study. For the multiclass criteria, the shrunken centroid method provides genes that are more different from the Febbo genes than the Fisher criterion. For the two-class separations, the tumor vs normal (G3+4 vs others) and the G4 vs. BPH provide similar Febbo enrichment while the G4 vs. all others gives gene sets that depart more from the Febbo genes. Finally, it is worth noting that the initial enrichment up to 1000 genes is of about 10% of Febbo genes in the gene set. After that, the enrichment decreases. This may be due to the fact that the genes are identified by their Unigene IDs and more than one probe is attributed to the same Id. In any case, the enrichment is very significant compared to the random ranking.

A number of probes do not have Unigene numbers. Of 22,283 lines in the Affymetrix data, 615 do not have Unigene numbers and there are only 14,640 unique Unigene numbers. In 10,130 cases, a unique matrix entry corresponds to a particular Unigene ID. However, 2,868 Unigene IDs are represented by 2 lines, 1,080 by 3 lines, and 563 by more than 3 lines. One Unigene ID covers 13 lines of data. For example, Unigene ID Hs.20019, identifies variants of Homo sapiens hemochromatosis (HFE) corresponding to GenBank accession numbers: AF115265.1, NM_000410.1, AF144240.1, AF150664.1, AF149804.1, AF144244.1, AF115264.1, AF144242.1, AF144243.1, AF144241.1, AF079408.1, AF079409.1, and (consensus) BG402-460.

The Unigene IDs of the paper of Febbo et al. (2003) were compared using the U95AV2 Affymetrix array and the IDs found in the U133A array under study. The Febbo paper reported 47 unique Unigene IDs for tumor high genes, 45 of which are IDs also found in the U133A array. Of the 49 unique Unigene IDs for normal high genes, 42 are also found in the U133A array. Overall, it is possible to see cross-correlations between the findings. There is a total of 96 Febbo genes that correspond to 173 lines (some genes being repeated) in the current matrix.

Based on the current results, one can either conclude that the "normal" tissues that are not BPH and drawn near the cancer tissues are on their way to cancer, or that BPH has a unique molecular signature that, although it may be considered "normal", makes it unfit as a control. A test set was created using 10 BPH samples and 10 grade 4 samples. Naturally, all BPH are in the TZ. The grade 4 are ½ in the TZ and ½ in the PZ.

Gene selection experiments were performed using the following filter methods:
(1)—Pearson's correlation coefficient to correlate with disease severity, where disease severity is coded as normal=1, dysplasia=2, grade3=3, grade4=4.
(2)—Fisher's criterion to separate the 4 classes (normal, dysplasia, grade3, grade4) with no consideration of disease severity.
(3)—Fisher's criterion to separate the 3 classes (PZ, CZ, TZ)
(4)—Relative Fisher criterion by computing the ratio of the between class variances of the disease severity and the zones, in an attempt to de-emphasize the zone factor.
(5)—Fisher's criterion to separate 8 classes corresponding to all the combinations of zones and disease severity found in the training data.
(6)—Using the combination of 2 rankings: the ranking of (1) and a ranking by zone for the grade 4 samples only. The idea is to identify genes that separate TZ from PZ cancers that have a different prognosis.

For each experiment, scatter plots were analyzed for the two best selected genes, the heat map of the 50 top ranked genes was reviewed, and p values were compared. The conclusions are as follows:

The Pearson correlation coefficient tracking disease severity (Experiment (1)) gives a similar ranking to the Fisher criterion, which discriminates between disease classes without ranking according to severity. However, the Pearson criterion has slightly better p values and, therefore, may give fewer false positives. The two best genes found by the Pearson criterion are gene 6519, ranked $6^{th}$ by the Fisher criterion, and gene 9457, ranked $1^{st}$ by the Fisher criterion. The test set examples are nicely separated, except for one outlier.

The zonal separation experiments were not conclusive because there are only 3 TZ examples in the training set and no example of CZ in the test set. Experiment (3) revealed a good separation of PZ and CZ on training data. TZ was not very well separated. Experiments (4) and (5) did not show very significant groupings. Experiment (6) found two genes that show both disease progression and that TZ G4 is grouped with "less severe diseases" than PZ G4, although that constraint was not enforced. To confirm the latter finding, the distance for the centroids of PZG4 and TZG4 were compared to control samples. Using the test set only (controls are BPH), 63% of all the genes show that TZG4 is closer to the control than PZG4. That number increases to 70% if the top 100 genes of experiment (6) are considered. To further confirm, experiment (6) was repeated with the entire dataset (without splitting between training and test). TZG4 is closer to normal than PZG4 for most top ranked genes. In the first 15 selected genes, 100% have TZG4 closer to normal than PZG4. This finding is significant because TZG4 has better prognosis than PZG4.

Classification experiments were performed to assess whether the appropriate features had been selected using the following setting:

The data were split into a training set and a test set. The test set consists of 20 samples: 10 BPH, 5 TZG4 and 5 PZG4. The training set contains the rest of the samples from the data set, a total of 67 samples (9 CZNL, 4 CZDYS, 1 CZG4, 13 PZNL, 13 PZDYS, 11PZG3, 13 PZG4, 3 TZG4). The training set does not contain any BPH.

Feature selection was performed on training data only. Classification was performed using linear ridge regression. The ridge value was adjusted with the leave-one-out error estimated using training data only. The performance criterion was the area under the ROC curve (AUC), where the ROC curve is a plot of the sensitivity as a function of the specificity. The AUC measures how well methods monitor the tradeoff sensitivity/specificity without imposing a particular threshold.

P values are obtained using a randomization method proposed by Tibshirani et al. Random "probes" that have a distribution similar to real features (gene) are obtained by randomizing the columns of the data matrix, with samples in lines and genes in columns. The probes are ranked in a similar manner as the real features using the same ranking criterion. For each feature having a given score s, where a larger score is better, a p value is obtained by counting the fraction of probes having a score larger than s. The larger the number of probes, the more accurate the p value.

For most ranking methods, and for forward selection criteria using probes to compute p values does not affect the ranking. For example, one can rank the probes and the features separately for the Fisher and Pearson criteria.

P values measure the probability that a randomly generated probe imitating a real gene, but carrying no information, gets a score larger or equal to s. Considering a single gene, if it has a score of s, the p value test can be used to test whether to reject the hypothesis that it is a random meaningless gene by setting a threshold on the p value, e.g., 0.0. The problem is that there are many genes of interest (in the present study, N=22, 283.) Therefore, it becomes probable that at least one of the genes having a score larger than s will be meaningless. Considering many genes simultaneously is like doing multiple testing in statistics. If all tests are independent, a simple correction known as the Bonferroni correction can be performed by multiplying the p values by N. This correction is conservative when the test are not independent.

From p values, one can compute a "false discovery rate" as FDR(s)=pvalue(s)*N/r, where r is the rank of the gene with score s, pvalue(s) is the associated p value, N is the total number of genes, and pvalue(s)*N is the estimated number of meaningless genes having a score larger than s. FDR estimates the ratio of the number of falsely significant genes over the number of genes call significant.

Of the classification experiments described above, the method that performed best was the one that used the combined criteria of the different classification experiments. In general, imposing meaningful constraints derived from prior knowledge seems to improve the criteria. In particular, simply applying the Fisher criterion to the G4 vs. all-the-rest separation (G4vsAll) yields good separation of the training examples, but poorer generalization than the more constrained criteria. Using a number of random probes equal to the number of genes, the G4vsAll identifies 170 genes before the first random probe, multiclass Fisher obtains 105 and the Pearson criterion measuring disease progression gets 377. The combined criteria identifies only 8 genes, which may be attributed to the different way in which values are computed. With respect to the number of Febbo genes found in the top ranking genes, G4 vs All has 20, multiclass Fisher 19, Pearson 19, and the combined criteria 8. The combined criteria provide a characterization of zone differentiation. On the other hand, the top 100 ranking genes found both by Febbo and by criteria G4 vs All, Fisher or Pearson have a high chance of having some relevance to prostate cancer. These genes are listed in Table 14.

TABLE 14

| Order Num | Unigene ID | Fisher | Pearson | G4 vs ALL | AUC | Description |
| --- | --- | --- | --- | --- | --- | --- |
| 12337 | Hs.7780 | 11 | 6 | 54 | 0.96 | cDNA DKFZp56A072 |
| 893 | Hs.226795 | 17 | 7 | 74 | 0.99 | Glutathione S-transferase pi (GSTP1) |
| 5001 | Hs.823 | 41 | 52 | 72 | 0.96 | Hepsin (transmembrance protease, serine 1) (HPN) |
| 1908 | Hs.692 | 62 | 34 | 111 | 0.96 | Tumor-associated calcium signal transducer 1 (TACSTD1) |
| 5676 | Hs.2463 | 85 | 317 | 151 | 1 | Angiopoietin 1 (ANGPT1) |
| 12113 | Hs.8272 | 181 | 93 | 391 | 1 | Prostaglandin D2 synthase (21 kD, brain) (PTGDS) |
| 12572 | Hs.9651 | 96 | 131 | 1346 | 0.99 | RAS related viral oncogene homolog (RRAS) |

Table 14 shows genes found in the top 100 as determined by the three criteria, Fisher, Pearson and G4vsALL, that were also reported in the Febbo paper. In the table, Order num is the order in the data matrix. The numbers in the criteria columns indicate the rank. The genes are ranked according to the sum of the ranks of the 3 criteria. Classifiers were trained with increasing subset sizes showing that a test AUC of 1 is reached with 5 genes.

The published literature was checked for the genes listed in Table 14. Third ranked Hepsin has been reported in several papers on prostate cancer: Chen et al. (2003) and Febbo et al. (2003) and is picked up by all criteria. Polymorphisms of second ranked GSTP1 (also picked by all criteria) are connected to prostate cancer risk (Beer et al, 2002). The fact that GSTP1 is found in semen (Lee (1978)) makes it a potentially interesting marker for non-invasive screening and monitoring. The clone DKFZp564A072, ranked first, is cited is several gene expression studies.

Fourth ranked Gene TACSTD1 was also previously described as more-highly expressed in prostate adenocarcinoma (see Lapointe et al, 2004 and references therein). Angiopoietin (ranked fifth) is involved in angiogenesis and known to help the blood irrigation of tumors in cancers and, in particular, prostate cancer (see e.g. Cane, 2003). Prostaglandin D2 synthase (ranked sixth) has been reported to be linked to prostate cancer in some gene expression analysis papers, but more interestingly, prostaglandin D synthase is found in semen (Tokugawa, 1998), making it another biomarker candidate for non-invasive screening and monitoring. Seventh ranked RRAS is an oncogene, so it makes sense to find it in cancer, however, its role in prostate cancer has not been documented.

A combined criterion was constructed for selecting genes according to disease severity NL<DYS<G3<G4 and simultaneously tries to differentiate TZG4 from PZG4 without ordering them. This following procedure was used:

Build an ordering using the Pearson criterion with encoded target vector having values NL=1, DYS=2, G3=3, G4=4 (best genes come last.)

Build an ordering using the Fisher criterion to separate TZG4 from PZG$ (best genes come last.)
Obtain a combined criterion by adding for each gene its ranks obtained with the first and second criterion.
Sort according to the combined criterion (in descending order, best first).

P values can be obtained for the combined criterion as follows:
Unsorted score vectors for real features (genes) and probes are concatenated for both criteria (Pearson and Fisher).
Genes and probes are sorted together for both criteria, in ascending order (best last).
The combined criterion is obtained by summing the ranks, as described above.

For each feature having a given combined criterion value s (larger values being better), a p value is obtained by counting the fraction of probes a having a combined criterion larger than s.

Note that this method for obtaining p values disturbs the ranking, so the ranking that was obtained without the probes listed in Table 15 was used.

A listing of genes obtained with the combined criterion are shown in Table 15. The ranking is performed on training data only. "Order num" designates the gene order number in the data matrix; p values are adjusted by the Bonferroni correction; "FDR" indicates the false discovery rate; "Test AUC" is the area under the ROC curve computed on the test set; and "Cancer cor" indicates over-expression in cancer tissues.

TABLE 15

| Rank | Order num | Unigene ID | P value | FDR | Test AUC | Cancer cor | Gene description |
|---|---|---|---|---|---|---|---|
| 1 | 3059 | Hs.771 | <0.1 | <0.01 | 0.96 | −1 | gb: NM_002863.1 /DEF = *Homo sapiens* phosphorylase, /UG = Hs.771 phosphorylase, glycogen; liver |
| 2 | 13862 | Hs.66744 | <0.1 | <0.01 | 0.96 | 1 | Consensus includes gb: X99268.1/DEF = H./FL = gb: NM_000474.1 |
| 3 | 13045 | Hs.173094 | <0.1 | <0.01 | 1 | −1 | Consensus includes gb: AI096375/FEA = EST |
| 4 | 5759 | Hs.66052 | <0.1 | <0.01 | 0.97 | −1 | gb: NM_001775.1/DEF = *Homo sapiens* CD38 |
| 5 | 18621 | Hs.42824 | <0.1 | <0.01 | 0.95 | −1 | gb: NM_018192.1/DEF = *Homo sapiens* hypothetical |
| 6 | 3391 | Hs.139851 | <0.1 | <0.01 | 0.94 | −1 | gb: NM_001233.1/DEF = *Homo sapiens* caveolin |
| 7 | 18304 | Hs.34045 | <0.1 | <0.01 | 0.95 | 1 | gb: NM_017955.1/DEF = *Homo sapiens* hypothetical |
| 8 | 14532 | Hs.37035 | <0.1 | <0.01 | 1 | 1 | Consensus includes gb: AI738662/FEA = EST |
| 9 | 3577 | Hs.285754 | 0.1 | 0.01 | 1 | −1 | Consensus includes gb: BG170541/FEA = EST |
| 10 | 9010 | Hs.180446 | 0.1 | 0.01 | 1 | 1 | gb: L38951.1/DEF = *Homo sapiens* importin |
| 11 | 13497 | Hs.71465 | 0.1 | 0.01 | 1 | −1 | Consensus includes gb: AA639705/FEA = EST |
| 12 | 19488 | Hs.17752 | 0.1 | 0.01 | 1 | 1 | gb: NM_015900.1/DEF = *Homo sapiens* phosph phospholipase A1alpha/FL = gb: AF035268.1 |
| 13 | 8838 | Hs.237825 | 0.1 | 0.01 | 1 | 1 | gb: AF069765.1/DEF = *Homo sapiens* signal gb: NM_006947.1 |
| 14 | 14347 | Hs.170250 | 0.1 | 0.01 | 1 | 1 | Consensus includes gb: K02403.1/DEF = Human |
| 15 | 2300 | Hs.69469 | 0.2 | 0.01 | 1 | 1 | gb: NM_006360.1/DEF = *Homo sapiens* dendritic |
| 16 | 10973 | Hs.77899 | 0.2 | 0.01 | 1 | −1 | gb: Z24727.1/DEF = *H. sapiens* tropomyosin |
| 17 | 11073 | Hs.0 | 0.2 | 0.01 | 1 | 1 | gb: Z25434.1/DEF = *H. sapiens* protein-serinethreonine |
| 18 | 22193 | Hs.165337 | 0.2 | 0.01 | 1 | 1 | Consensus includes gb: AW971415/FE |
| 19 | 12742 | Hs.237506 | 0.2 | 0.01 | 1 | −1 | Consensus includes gb: AK023253.1/DEF = |
| 20 | 21823 | Hs.9614 | 0.3 | 0.01 | 1 | 1 | Consensus includes gb: AA191576/FEA = EST |
| 21 | 13376 | Hs.246885 | 0.3 | 0.01 | 1 | −1 | Consensus includes gb: W87466/FEA = EST |
| 22 | 6182 | Hs.77899 | 0.3 | 0.01 | 1 | −1 | gb: NM_000366.1/DEF = *Homo sapiens* tropomyosin |
| 23 | 3999 | Hs.1162 | 0.4 | 0.02 | 1 | 1 | gb: NM_002118.1/DEF = *Homo sapiens* major II, DM beta/FL = gb: NM_002118.1 gb: U15085.1 |
| 24 | 1776 | Hs.168670 | 0.7 | 0.03 | 1 | −1 | gb: NM_002857.1/DEF = *Homo sapiens* peroxisomal gb: AB018541.1 |
| 25 | 4046 | Hs.82568 | 0.7 | 0.03 | 1 | −1 | gb: NM_000784.1/DEF = *Homo sapiens* cytochrome cerebrotendinous xanthomatosis), polypeptide |
| 26 | 6924 | Hs.820 | 0.8 | 0.03 | 1 | 1 | gb: NM_004503.1/DEF = *Homo sapiens* homeo |
| 27 | 2957 | Hs.1239 | 0.9 | 0.03 | 1 | −1 | gb: NM_001150.1/DEF = *Homo sapiens* alanyl/DB_XREF = gi: 4502094/UG = Hs.1239 alanyl |
| 28 | 5699 | Hs.78406 | 1.3 | 0.05 | 1 | −1 | gb: NM_003558.1/DEF = *Homo sapiens* phosphatidylinositol phosphate 5-kinase, type I, beta/FL = gb: NM |
| 29 | 19167 | Hs.9238 | 1.4 | 0.05 | 1 | −1 | gb: NM_024539.1/DEF = *Homo sapiens* hypothetical |
| 30 | 4012 | Hs.172851 | 1.4 | 0.05 | 1 | −1 | gb: NM_001172.1/DEF = *Homo sapiens* arginase, gb: D86724.1 gb: U75667.1 gb: U82256.1 |
| 31 | 9032 | Hs.80658 | 1.4 | 0.05 | 1 | −1 | gb: U94592.1/DEF = Human uncoupling protein gb: U82819.1 gb: U94592.1 |
| 32 | 15425 | Hs.20141 | 1.5 | 0.05 | 1 | 1 | Consensus includes gb: AK000970.1/DEF = |
| 33 | 14359 | Hs.155956 | 1.6 | 0.05 | 1 | −1 | Consensus includes gb: NM_000662.1/DEF = acetyltransferase)/FL = gb: NM_000662.1 |
| 34 | 6571 | Hs.89691 | 1.6 | 0.05 | 1 | 1 | gb: NM_021139.1/DEF = *Homo sapiens* UDP polypeptide B4/FL = gb: NM_021139.1 gb: AF064200.1 |
| 35 | 13201 | Hs.301552 | 1.8 | 0.05 | 1 | 1 | Consensus includes gb: AK000478.1/DEF = |
| 36 | 21754 | Hs.292911 | 1.8 | 0.05 | 1 | −1 | Consensus includes gb: AI378979/FEA = EST |

TABLE 15-continued

| Rank | Order num | Unigene ID | P value | FDR | Test AUC | Cancer cor | Gene description |
|---|---|---|---|---|---|---|---|
| 37 | 5227 | Hs.31034 | 2 | 0.05 | 1 | −1 | Consensus includes gb: AL360141.1/DEF = |
| 38 | 18969 | Hs.20814 | 2.1 | 0.06 | 1 | 1 | gb: NM__015955.1/DEF = *Homo sapiens* CGI |
| 39 | 17907 | Hs.24395 | 2.2 | 0.06 | 1 | 1 | gb: NM__004887.1/DEF = *Homo sapiens* small small inducible cytokine subfamily B (Cys |
| 40 | 3831 | Hs.77695 | 2.3 | 0.06 | 1 | 1 | gb: NM__014750.1/DEF = *Homo sapiens* KIAA0008 |
| 41 | 10519 | Hs.4975 | 2.4 | 0.06 | 0.98 | 1 | gb: D82346.1/DEF = *Homo sapiens* mRNA |
| 42 | 2090 | Hs.150580 | 2.4 | 0.06 | 0.97 | −1 | gb: AF083441.1/DEF = *Homo sapiens* SUI1 |
| 43 | 9345 | Hs.75244 | 2.6 | 0.06 | 0.97 | −1 | gb: D87461.1/DEF = Human mRNA for KIAA0271 |
| 44 | 3822 | Hs.36708 | 2.7 | 0.06 | 0.97 | 1 | gb: NM__001211.2/DEF = *Homo sapiens* budding uninhibited by benzimidazoles 1 (yeast homolog) |
| 45 | 17999 | Hs.179666 | 2.9 | 0.06 | 0.97 | −1 | gb: NM__018478.1/DEF = *Homo sapiens* uncharacterized HSMNP1/FL = gb: BC001105.1 gb: AF220191.1 |
| 46 | 5070 | Hs.118140 | 2.9 | 0.06 | 0.96 | 1 | gb: NM__014705.1/DEF = *Homo sapiens* KIAA0716 |
| 47 | 20627 | Hs.288462 | 3 | 0.06 | 0.98 | −1 | gb: NM__025087.1/DEF = *Homo sapiens* hypothetical |
| 48 | 14690 | Hs.110826 | 3 | 0.06 | 0.99 | 1 | Consensus includes gb: AK027006.1/DEF = |
| 49 | 18137 | Hs.9641 | 3 | 0.06 | 0.98 | 1 | gb: NM__015991.1/DEF = *Homo sapiens* complement component 1, q subcomponent, alpha polypeptide-1 |
| 50 | 9594 | Hs.182278 | 3 | 0.06 | 0.98 | −1 | gb: BC000454.1/DEF = *Homo sapiens*, cal/FL = gb: BC000454.1 |

From Table 15, the combined criteria give an AUC of 1 between 8 and 40 genes. This indicates that subsets of up to 40 genes taken in the order of the criteria have a high predictive power. However, genes individually can also be judged for their predictive power by estimating p values. P values provide the probability that a gene is a random meaningless gene. A threshold can be set on that p value, e.g. 0.05.

Using the Bonferroni correction ensures that p values are not underestimated when a large number of genes are tested. This correction penalizes p values in proportion to the number of genes tested. Using 10*N probes (N=number of genes) the number of genes that score higher than all probes are significant at the threshold 0.1. Eight such genes were found with the combined criterion, while 26 genes were found with a p value<1.

It may be useful to filter out as many genes as possible before ranking them in order to avoid an excessive penalty. When the genes were filtered with the criterion that the standard deviation should exceed twice the mean (a criterion not involving any knowledge of how useful this gene is to predict cancer). This reduced the gene set to N'=571, but there were also only 8 genes at the significance level of 0.1 and 22 genes had p value<1.

The 8 first genes found by this method are given in Table 16. Genes over-expressed in cancer are under Rank 2, 7, and 8 (underlined). The remaining genes are under-expressed.

TABLE 16

| Rank | Unigene ID | Description and findings |
|---|---|---|
| 1 | Hs.771 | Phosphorylase, glycogen; liver (Hers disease, glycogen storage disease type VI) (PYGL). |
| <u>2</u> | <u>Hs.66744</u> | <u>B-HLH DNA binding protein. H-twist.</u> |
| 3 | Hs.173094 | KIAA1750 |
| 4 | Hs.66052 | CD38 antigen (p45) |
| 5 | Hs.42824 | FLJ10718 hypothetical protein |
| 6 | Hs.139851 | Caveolin 2 (CAV2) |
| <u>7</u> | <u>Hs.34045</u> | <u>FLJ20764 hypothetical protein</u> |
| <u>8</u> | <u>Hs.37035</u> | <u>Homeo box HB9</u> |

Genes were ranked using the Pearson correlation criterion, see Table 17, with disease progression coded as Normal=1, Dysplasia=2, Grade3=3, Grade4=4. The p values are smaller than in the genes of Table 15, but the AUCs are worse. Three Febbo genes were found, corresponding to genes ranked $6^{th}$, $7^{th}$ and $34^{th}$.

TABLE 17

| Rank | Order num | Unigene ID | Pvalue | FDR | Test AUC | Cancer cor | Febbo | Gene description |
|---|---|---|---|---|---|---|---|---|
| 1 | 6519 | Hs.243960 | <0.1 | <0.0003 | 0.85 | −1 | 0 | gb: NM__016250.1/DEF = Homo s |
| 2 | 9457 | Hs.128749 | <0.1 | <0.0003 | 0.93 | 1 | 0 | Consensus includes gb: AI796120 |
| 3 | 9976 | Hs.103665 | <0.1 | <0.0003 | 0.89 | −1 | 0 | gb: BC004300.1/DEF = *Homo sapiens*, |
| 4 | 9459 | Hs.128749 | <0.1 | <0.0003 | 0.87 | 1 | 0 | gb: AF047020.1/DEF = *Homo sapiens* gb: NM__014324.1 |
| 5 | 9458 | Hs.128749 | <0.1 | <0.0003 | 0.89 | 1 | 0 | Consensus includes gb: AA888 |
| 6 | 12337 | Hs.7780 | <0.1 | <0.0003 | 0.96 | 1 | 1 | Consensus includes gb: AV715767 |
| 7 | 893 | Hs.226795 | <0.1 | <0.0003 | 0.97 | −1 | 1 | gb: NM__000852.2/DEF = *Homo sapiens* |
| 8 | 19589 | Hs.45140 | <0.1 | <0.0003 | 0.98 | −1 | 0 | gb: NM__021637.1/DEF = *Homo sapiens* |
| 9 | 11911 | Hs.279009 | <0.1 | <0.0003 | 0.98 | −1 | 0 | Consensus includes gb: AI653730 |
| 10 | 17944 | Hs.279905 | <0.1 | <0.0003 | 0.96 | 1 | 0 | gb: NM__016359.1/DEF = *Homo sapiens* gb: AF290612.1 gb: AF090915.1 |
| 11 | 9180 | Hs.239926 | <0.1 | <0.0003 | 0.96 | −1 | 0 | Consensus includes gb: AV704962 |
| 12 | 18122 | Hs.106747 | <0.1 | <0.0003 | 0.96 | −1 | 0 | gb: NM__021626.1/DEF = *Homo sapiens* protein /FL = gb: AF282618.1 gb: NM__ |
| 13 | 12023 | Hs.74034 | <0.1 | <0.0003 | 0.96 | −1 | 0 | Consensus includes gb: AU14739 |
| 14 | 374 | Hs.234642 | <0.1 | <0.0003 | 0.96 | −1 | 0 | Cluster Incl. 74607: za55a01.s1 |
| 15 | 12435 | Hs.82432 | <0.1 | <0.0003 | 0.96 | −1 | 0 | Consensus includes b: AA135522 |

TABLE 17-continued

| Rank | Order num | Unigene ID | Pvalue | FDR | Test AUC | Cancer cor | Febbo | Gene description |
|---|---|---|---|---|---|---|---|---|
| 16 | 18598 | Hs.9728 | <0.1 | <0.0003 | 0.96 | −1 | 0 | gb: NM_016608.1/DEF = *Homo sapiens* |
| 17 | 3638 | Hs.74120 | <0.1 | <0.0003 | 0.97 | −1 | 0 | gb: NM_006829.1/DEF = *Homo sapiens* |
| 18 | 5150 | Hs.174151 | <0.1 | <0.0003 | 0.97 | −1 | 0 | gb: NM_001159.2/DEF = *Homo sapiens* |
| 19 | 1889 | Hs.195850 | <0.1 | <0.0003 | 0.97 | −1 | 0 | gb: NM_000424.1/DEF = *Homo sapiens*/DB_XREF = gi: 4557889/UG = Hs. |
| 20 | 3425 | Hs.77256 | <0.1 | <0.0003 | 0.97 | 1 | 0 | gb: NM_004456.1/DEF = *Homo sapiens*/FL = gb: U61145.1 gb: NM_004456.1 |
| 21 | 5149 | Hs.174151 | <0.1 | <0.0003 | 0.96 | −1 | 0 | gb: AB046692.1/DEF = *Homo sapiens* |
| 22 | 4351 | Hs.303090 | <0.1 | <0.0003 | 0.97 | −1 | 0 | Consensus includes gb: N26005 |
| 23 | 4467 | Hs.24587 | <0.1 | <0.0003 | 0.97 | −1 | 0 | gb: NM_005864.1/DEF = *Homo sapiens*/FL = gb: AB001466.1 gb: NM_005864.1 |
| 24 | 12434 | Hs.250723 | <0.1 | <0.0003 | 0.96 | −1 | 0 | Consensus includes gb: BF968134 |
| 25 | 12809 | Hs.169401 | <0.1 | <0.0003 | 0.95 | 1 | 0 | Consensus includes gb: AI358867 |
| 26 | 7082 | Hs.95197 | <0.1 | <0.0003 | 0.95 | −1 | 0 | gb: AB015228.1/DEF = *Homo sapiens* gb: AB015228.1 |
| 27 | 18659 | Hs.73625 | <0.1 | <0.0003 | 0.95 | 1 | 0 | gb: NM_005733.1/DEF = *Homo sapiens* (rabkinesin6)/FL = gb: AF070672.1 |
| 28 | 13862 | Hs.66744 | <0.1 | <0.0003 | 0.98 | 1 | 0 | Consensus includes gb: X99268.1 syndrome)/FL = gb: NM_000474 |
| 29 | 3059 | Hs.771 | <0.1 | <0.0003 | 0.98 | −1 | 0 | gb: NM_002863.1/DEF = *Homo sapiens*/DB_XREF = gi: 4506352/UG = Hs. |
| 30 | 15294 | Hs.288649 | <0.1 | <0.0003 | 0.98 | 1 | 0 | Consensus includes gb: AK0 |
| 31 | 9325 | Hs.34853 | <0.1 | <0.0003 | 0.99 | −1 | 0 | Consensus includes gb: AW157094 |
| 32 | 18969 | Hs.20814 | <0.1 | <0.0003 | 0.98 | 1 | 0 | gb: NM_015955.1/DEF = *Homo sapiens* |
| 33 | 4524 | Hs.65029 | <0.1 | <0.0003 | 0.96 | −1 | 0 | gb: NM_002048.1/DEF = *Homo sapiens* |
| 34 | 1908 | Hs.692 | <0.1 | <0.0003 | 0.97 | 1 | 1 | gb: NM_002354.1/DEF = *Homo sapiens* signal transducer 1/FL = gb: M32306.1 |
| 35 | 11407 | Hs.326776 | <0.1 | <0.0003 | 0.96 | −1 | 0 | gb: AF180519.1/DEF = *Homo sapiens* cds/FL = gb: AF180519.1 |
| 36 | 19501 | Hs.272813 | <0.1 | <0.0003 | 0.96 | −1 | 0 | gb: NM_017434.1/DEF = *Homo sapiens* |
| 37 | 11248 | Hs.17481 | <0.1 | <0.0003 | 0.96 | −1 | 0 | gb: AF063606.1/DEF = *Homo sapiens* |
| 38 | 5894 | Hs.80247 | <0.1 | <0.0003 | 0.95 | −1 | 0 | gb: NM_000729.2/DEF = *Homo sapiens* |
| 39 | 19455 | Hs.26892 | <0.1 | <0.0003 | 0.96 | −1 | 0 | gb: NM_018456.1/DEF = Homo sapie BM040/FL = gb: AF217516.1 gb: |
| 40 | 3448 | Hs.169401 | <0.1 | <0.0003 | 0.96 | 1 | 0 | Consensus includes gb: N33009 |
| 41 | 6666 | Hs.90911 | <0.1 | <0.0003 | 0.96 | −1 | 0 | gb: NM_004695.1/DEF = *Homo sapiens*/UG = Hs.90911 solute carrier family |
| 42 | 6924 | Hs.820 | <0.1 | <0.0003 | 0.98 | 1 | 0 | gb: NM_004503.1/DEF = *Homo sapiens* |
| 43 | 2169 | Hs.250811 | <0.1 | <0.0003 | 0.98 | −1 | 0 | Consensus includes gb: BG169673 |
| 44 | 12168 | Hs.75318 | <0.1 | <0.0003 | 0.98 | −1 | 0 | Consensus includes gb: AL565074 |
| 45 | 18237 | Hs.283719 | <0.1 | <0.0003 | 0.98 | −1 | 0 | gb: NM_018476.1/DEF = *Homo sapiens* HBEX2/FL = gb: AF220189.1 gb: |
| 46 | 5383 | Hs.182575 | <0.1 | <0.0003 | 0.98 | −1 | 0 | Consensus includes gb: BF223679 |
| 47 | 19449 | Hs.17296 | <0.1 | <0.0003 | 0.99 | −1 | 0 | gb: NM_023930.1/DEF = *Homo sapiens* gb: BC001929.1 gb: NM_023930.1 |
| 48 | 4860 | Hs.113082 | <0.1 | <0.0003 | 0.99 | −1 | 0 | gb: NM_014710.1/DEF = *Homo sapiens* |
| 49 | 17714 | Hs.5216 | <0.1 | <0.0003 | 0.99 | 1 | 0 | gb: NM_014038.1/DEF = *Homo sapiens* |
| 50 | 12020 | Hs.137476 | <0.1 | <0.0003 | 0.97 | −1 | 0 | Consensus includes gb: AL582836 |

The data is rich in potential biomarkers. To find the most promising markers, criteria were designed to implement prior knowledge of disease severity and zonal information. This allowed better separation of relevant genes from genes that coincidentally well separate the data, thus alleviating the problem of overfitting. To further reduce the risk of overfitting, genes were selected that were also found in an independent study Table 15. Those genes include well-known proteins involved in prostate cancer and some potentially interesting targets.

EXAMPLE 5

Prostate Cancer Gene Expression Microarray Data (11-2004)

Separations of class pairs were performed for "tumor (G3+4) vs. all other tissues". These separations are relatively easy and can be performed with fewer than 10 genes, however, hundreds of significant genes were identified.

Separations of "G4 vs. all others", "Dysplasia vs. all others", and "Normal vs. all others" are less easy (best AUCs between 0.75 and 0.85) and separation of "G3 vs. all others" is almost impossible in this data (AUC around 0.5). With over 100 genes, G4 can be separated from all other tissues with about 10% BER. Hundreds of genes separate G4 from all other tissues significantly, yet one cannot find a good separation with just a few genes.

Separations of "TZG4 vs. PZG4", "Normal vs. Dysplasia" and "G3 vs. G4" are also hard. 10×10-fold CV yielded very poor results. Using leave-one out CV and under 20 genes, we separated some pairs of classes: $ERR_{TZG4/PZG4} \approx 6\%$, $ERRN_{NL/Dys}$ and $ERR_{G3/G4} \approx 9\%$. However, due to the small sample sizes, the significance of the genes found for those separations is not good, shedding doubt on the results.

Pre-operative PSA was found to correlate poorly with clinical variables ($R^2 = 0.316$ with cancer volume, 0.025 with prostate weight, and 0.323 with CAvol/Weight). Genes were found with activity that correlated with pre-operative PSA either in BPH samples or G34 samples or both. Possible connections of those genes were found to cancer and/or prostate in the literature, but their relationship to PSA is not documented. Genes associated to PSA by their description do not have expression values correlated with pre-operative PSA. This illustrates that gene expression coefficients do not necessarily reflect the corresponding protein abundance.

Genes were identified that correlate with cancer volume in G3+4 tissues and with cure/fail prognosis. Neither are statistically significant, however, the gene most correlated with cancer volume has been reported in the literature as connected to prostate cancer. Prognosis information can be used in conjunction with grade levels to determine the significance of genes. Several genes were identified for separating G4 from non-G4 and G3 from G3 in the group the samples of patients with the poor prognosis in regions of lowest expression values.

The following experiments were performed using data consisting of a matrix of 87 lines (samples) and 22283 columns (genes) obtained from an Affymetrix U133A Gene-Chip®. The distributions of the samples of the microarray prostate cancer study are the same as those listed in Table 12.

Genes were selected on the basis of their individual separating power, as measured by the AUC (area under the ROC curve that plots sensitivity vs. specificity).

Similarly "random genes" that are genes obtained by permuting randomly the values of columns of the matrix are ranked. Where N is the total number of genes (here, N=22283, 40 times more random genes than real genes are used to estimate p values accurately ($N_r$=40*22283). For a given AUC value A, $n_r(A)$ is the number of random genes that have an AUC larger than A. The p value is estimated by the fraction of random genes that have an AUC larger than A, i.e.:

$$Pvalue=(1+n_r(A))/N_r$$

Adding 1 to the numerator avoids having zero p values for the best ranking genes and accounts for the limited precision due to the limited number of random genes. Because the pvalues of a large number of genes are measured simultaneously, correction must be applied to account for this multiple testing. As in the previous example, the simple Bonferroni correction is used:

$$Bonferroni\_pvalue=N*(1+n_r(A))/N_r$$

Hence, with a number of probes that is 40 times the number of genes, the p values are estimated with an accuracy of 0.025.

For a given gene of AUC value A, one can also compute the false discovery rate (FDR), which is an estimate of the ratio of the number of falsely significant genes over the number of genes called significant. Where n(A) is the number of genes found above A, the FDR is computed as the ratio of the p value (before Bonferroni correction) and the fraction of real genes found above A:

$$FDR=pvalue*N/n(A)=((1+n_r(A))*N)/(n(A)*N_r).$$

Linear ridge regression classifiers (similar to SVMs) were trained with 10×10-fold cross validation, i.e., the data were split 100 times into a training set and a test set and the average performance and standard deviation were computed. In these experiments, the feature selection is performed within the cross-validation loop. That is, a separate featuring ranking is performed for each data split. The number of features are varied and a separate training/testing is performed for each number of features. Performances for each number of features are averaged to plot performance vs. number of features. The ridge value is optimized separately for each training subset and number of features, using the leave-one—out error, which can be computed analytically from the training error. In some experiments, the 10×10-fold cross-validation was done by leave-one-out cross-validation. Everything else remains the same.

Using the rankings obtained for the 100 data splits of the machine learning experiments (also called "bootstraps"), average gene ranks are computed. Average gene rank carries more information in proportion to the fraction of time a gene was always found in the top N ranking genes. This last criterion is sometimes used in the literature, but the number of genes always found in the top N ranking genes appears to grows linearly with N.

The following statistics were computed for cross-validation (10 times 10-fold or leave-one-out) of the machine learning experiments:

AUC mean: The average area under the ROC curve over all data splits.

AUC stdev: The corresponding standard deviation. Note that the standard error obtained by dividing stdev by the square root of the number of data splits is inaccurate because sampling is done with replacements and the experiments are not independent of one another.

BER mean: The average BER over all data splits. The BER is the balanced error rate, which is the average of the error rate of examples of the first class and examples of the second class. This provides a measure that is not biased toward the most abundant class.

BER stdev: The corresponding standard deviation.

Pooled AUC: The AUC obtained using the predicted classification values of all the test examples in all data splits altogether.

Pooled BER: The BER obtained using the predicted classification values of all the test examples in all data splits altogether.

Note that for leave-one-out CV, it does not make sense to compute BER-mean because there is only one example in each test set. Instead, the leave-one-out error rate or the pooled BER is computed.

High classification accuracy (as measured by the AUC) can be achieved a small number of genes (3 or more) to provide an AUC above 0.90. If the experimental repeats were independent, the standard error of the mean obtained by dividing the standard deviation by 10 could be used as an error bar. A more reasonable estimate of the error bar may be obtained by dividing it by three to account for the dependencies between repeats.

The genes listed in the following tables are ranked according to their individual AUC computed with all the data. The first column is the rank, followed by the Gene ID (order number in the data matrix), and the Unigene ID. The column "Under Expr" is +1 if the gene is underexpressed and −1 otherwise. AUC is the ranking criterion. Pval is the pvalue computed with random genes as explained above. FDR is the false discovery rate. "Ave. rank" is the average rank of the feature when subsamples of the data are taken in a 10×10-fold cross-validation experiment in Tables 18, 21, 23, 25 & 27 and with leave-one-out in Tables 29, 31 & 33.

In the test to separate tumors (cancer G3 and G4) from other tissues, the results show that it is relatively easy to separate tumor from other tissues. The list of the top 50 tumor genes, both overexpressed and underexpressed in cancer, is shown in Table 18. A complete listing of the top 200 tumor genes is provided in FIGS. 4a-4d. The three best genes, Gene IDs no. 9457, 9458 and 9459 all have same Unigene ID. Additional description about the top three genes is provided in Table 19 below.

TABLE 18

| Rank | Gene ID | Unigene ID | Under Expr. In tumor | AUC | Pval | FDR | Ave. rank |
|---|---|---|---|---|---|---|---|
| 1 | 9459 | Hs.128749 | −1 | 0.9458 | 0.02 | 0.025 | 1.16 |
| 2 | 9458 | Hs.128749 | −1 | 0.9425 | 0.02 | 0.012 | 2.48 |
| 3 | 9457 | Hs.128749 | −1 | 0.9423 | 0.02 | 0.0083 | 2.51 |
| 4 | 11911 | Hs.279009 | 1 | 0.9253 | 0.02 | 0.0062 | 4.31 |
| 5 | 12337 | Hs.7780 | −1 | 0.9125 | 0.02 | 0.005 | 7.23 |
| 6 | 983 | Hs.226795 | 1 | 0.9076 | 0.02 | 0.0042 | 8.42 |
| 7 | 18792 | Hs.6823 | −1 | 0.9047 | 0.02 | 0.0036 | 10.04 |
| 8 | 1908 | Hs.692 | −1 | 0.9044 | 0.02 | 0.0031 | 10.03 |
| 9 | 19589 | Hs.45140 | 1 | 0.9033 | 0.02 | 0.0028 | 10.47 |
| 10 | 6519 | Hs.243960 | 1 | 0.8996 | 0.02 | 0.0025 | 12.67 |
| 11 | 17714 | Hs.5216 | −1 | 0.8985 | 0.02 | 0.0023 | 13.93 |
| 12 | 18122 | Hs.106747 | 1 | 0.8985 | 0.02 | 0.0021 | 13.86 |
| 13 | 18237 | Hs.283719 | 1 | 0.8961 | 0.02 | 0.0019 | 16.61 |
| 14 | 3059 | Hs.771 | 1 | 0.8942 | 0.02 | 0.0018 | 17.86 |
| 15 | 16533 | Hs.110826 | −1 | 0.8921 | 0.02 | 0.0017 | 19.44 |
| 16 | 18598 | Hs.9728 | 1 | 0.8904 | 0.02 | 0.0016 | 19.43 |
| 17 | 12434 | Hs.250723 | 1 | 0.8899 | 0.02 | 0.0015 | 20.19 |
| 18 | 4922 | Hs.55279 | 1 | 0.884 | 0.02 | 0.0014 | 27.23 |
| 19 | 13862 | Hs.66744 | −1 | 0.8832 | 0.02 | 0.0013 | 30.59 |
| 20 | 9976 | Hs.103665 | 1 | 0.8824 | 0.02 | 0.0012 | 30.49 |
| 21 | 18835 | Hs.44278 | −1 | 0.8824 | 0.02 | 0.0012 | 30.94 |
| 22 | 3331 | Hs.54697 | 1 | 0.8802 | 0.02 | 0.0011 | 32.35 |
| 23 | 18969 | Hs.20814 | −1 | 0.8797 | 0.02 | 0.0011 | 35.89 |
| 24 | 9373 | Hs.21293 | −1 | 0.8786 | 0.02 | 0.001 | 35.52 |
| 25 | 15294 | Hs.288649 | −1 | 0.8786 | 0.02 | 0.001 | 35.69 |
| 26 | 4497 | Hs.33084 | 1 | 0.8776 | 0.02 | 0.00096 | 37.77 |
| 27 | 5001 | Hs.823 | −1 | 0.8765 | 0.02 | 0.00093 | 40.25 |
| 28 | 9765 | Hs.22599 | 1 | 0.8765 | 0.02 | 0.00089 | 39.32 |
| 29 | 4479 | Hs.198760 | 1 | 0.8759 | 0.02 | 0.00086 | 40.82 |
| 30 | 239 | Hs.198760 | 1 | 0.8749 | 0.02 | 0.00083 | 43.04 |
| 31 | 6666 | Hs.90911 | 1 | 0.8749 | 0.02 | 0.00081 | 42.53 |
| 32 | 12655 | Hs.10587 | 1 | 0.8749 | 0.02 | 0.00078 | 41.56 |
| 33 | 19264 | Hs.31608 | −1 | 0.8743 | 0.02 | 0.00076 | 44.66 |
| 34 | 5923 | Hs.171731 | 1 | 0.8738 | 0.02 | 0.00074 | 44.3 |
| 35 | 1889 | Hs.195850 | 1 | 0.8727 | 0.02 | 0.00071 | 46.1 |
| 36 | 21568 | Hs.111676 | 1 | 0.8716 | 0.02 | 0.00069 | 48.3 |
| 37 | 3264 | Hs.139336 | −1 | 0.8714 | 0.02 | 0.00068 | 51.17 |
| 38 | 14738 | Hs.8198 | 1 | 0.8706 | 0.02 | 0.00066 | 52.7 |
| 39 | 1867 | Hs.234680 | 1 | 0.8695 | 0.02 | 0.00064 | 52.99 |
| 40 | 4467 | Hs.24587 | 1 | 0.8695 | 0.02 | 0.00062 | 52.25 |
| 41 | 9614 | Hs.8583 | 1 | 0.8695 | 0.02 | 0.00061 | 53.62 |
| 42 | 18659 | Hs.73625 | −1 | 0.8692 | 0.02 | 0.0006 | 56.86 |
| 43 | 20137 | Hs.249727 | 1 | 0.8692 | 0.02 | 0.00058 | 55.2 |
| 44 | 12023 | Hs.74034 | 1 | 0.869 | 0.02 | 0.00057 | 55.69 |
| 45 | 12435 | Hs.82432 | 1 | 0.869 | 0.02 | 0.00056 | 56.63 |
| 46 | 14626 | Hs.23960 | −1 | 0.8687 | 0.02 | 0.00054 | 58.95 |
| 47 | 7082 | Hs.95197 | 1 | 0.8684 | 0.02 | 0.00053 | 56.27 |
| 48 | 15022 | Hs.110826 | −1 | 0.8679 | 0.02 | 0.00052 | 59.51 |
| 49 | 20922 | Hs.0 | −1 | 0.8679 | 0.02 | 0.00051 | 59.93 |
| 50 | 4361 | Hs.102 | 1 | 0.8673 | 0.02 | 0.0005 | 60.94 |

TABLE 19

| Gene ID | Description |
|---|---|
| 9457 | gb: AI796120 /FEA = EST /DB_XREF = gi: 5361583 /DB_XREF = est: wh42f03.x1 /CLONE = IMAGE: 2383421 /UG = Hs.128749 alphamethylacyl-CoA racemase /FL = gb: AF047020.1 gb: AF158378.1 gb: NM_014324.1 |
| 9458 | gb: AA888589 /FEA = EST /DB_XREF = gi: 3004264 /DB_XREF = est: oe68e10.s1 /CLONE = IMAGE: 1416810 /UG = Hs.128749 alphamethylacyl-CoA racemase /FL = gb: AF047020.1 gb: AF158378.1 gb: NM_014324.1 |
| 9459 | gb: AF047020.1 /DEF = *Homo sapiens* alpha-methylacyl-CoA racemase mRNA, complete cds. /FEA = mRNA /PROD = alpha-methylacyl-CoA racemase /DB_XREF = gi: 4204096 /UG = Hs.128749 alpha-methylacyl-CoA racemase /FL = gb: AF047020.1 gb: AF158378.1 gb: NM_014324.1 |

This gene has been reported in numerous papers including Luo, et al., *Molecular Carcinogenesis*, 33(1): 25-35 (January 2002); Luo J, et al., *Abstract Cancer Res.*, 62(8): 2220-6 (2002 Apr. 15).

Table 20 shows the separation with varying number of features for tumor (G3+4) vs. all other tissues.

TABLE 20

| | feat. num. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 16 | 32 | 64 | 128 |
| 100 * AUC | 92.28 | 93.33 | 93.83 | 94 | 94.33 | 94.43 | 94.1 | 93.8 | 93.43 | 93.53 | 93.45 | 93.37 | 93.18 | 93.03 |
| 100 * AUCstd | 11.73 | 10.45 | 10 | 9.65 | 9.63 | 9.61 | 10.3 | 10.54 | 10.71 | 10.61 | 10.75 | 10.44 | 11.49 | 11.93 |
| BER (%) | 14.05 | 13.1 | 12.6 | 10.25 | 9.62 | 9.72 | 9.75 | 9.5 | 9.05 | 9.05 | 9.7 | 9.6 | 10.12 | 9.65 |
| BERstd (%) | 13.51 | 12.39 | 12.17 | 11.77 | 9.95 | 10.06 | 10.15 | 10.04 | 9.85 | 10.01 | 10.2 | 10.3 | 10.59 | 10.26 |

Using the same experimental setup, separations were attempted for G4 from non G4, G3 from non G3, Dysplasia from non-dys and Normal from non-Normal. These separations were less successful than the above-described tests, indicating that G3, dysplasia and normal do not have molecular characteristics that distinguish them easily from all other samples. Lists of genes are provided in Tables 21-37.

Table 21 lists the top 10 genes separating Grade 4 prostate cancer (G4) from all others.

TABLE 21

| Rank | Gene ID | Unigene ID | Under Expr. In G4 | AUC | Pval | FDR | Ave. rank |
|---|---|---|---|---|---|---|---|
| 1 | 5923 | Hs.171731 | 1 | 0.9204 | 0.02 | 0.025 | 3.25 |
| 2 | 18122 | Hs.106747 | 1 | 0.9136 | 0.02 | 0.012 | 6.17 |
| 3 | 19573 | Hs.232165 | 1 | 0.9117 | 0.02 | 0.0083 | 7.92 |
| 4 | 893 | Hs.226795 | 1 | 0.9099 | 0.02 | 0.0062 | 7.22 |
| 5 | 9889 | Hs.137569 | 1 | 0.9093 | 0.02 | 0.005 | 9.88 |
| 6 | 19455 | Hs.26892 | 1 | 0.908 | 0.02 | 0.0042 | 10.54 |
| 7 | 19589 | Hs.45140 | 1 | 0.9074 | 0.02 | 0.0036 | 10.54 |
| 8 | 18598 | Hs.9728 | 1 | 0.9062 | 0.02 | 0.0031 | 10.83 |
| 9 | 6519 | Hs.243960 | 1 | 0.9037 | 0.02 | 0.0028 | 12.79 |
| 10 | 11175 | Hs.137569 | 1 | 0.9031 | 0.02 | 0.0025 | 13.46 |

Table 22 below provides the details for the top two genes of this group.

TABLE 22

| Gene ID | Description |
|---|---|
| 5923 | gb: NM_015865.1 /DEF = *Homo sapiens* solute carrier family 14 (urea transporter), member 1 (Kidd blood group) (SLC14A1), mRNA. /FEA = mRNA /GEN = SLC14A1 /PROD = RACH1 /DB_XREF = gi: 7706676 /UG = Hs.171731 solute carrier family 14 (urea transporter), member 1 (Kidd blood group) /FL = gb: U35735.1 gb: NM_015865.1 |
| 18122 | gb: NM_021626.1 /DEF = *Homo sapiens* serine carboxypeptidase 1 precursor protein (HSCP1), mRNA. /FEA = mRNA /GEN = HSCP1 /PROD = serine carboxypeptidase 1 precursor protein /DB_XREF = gi: 11055991 /UG = Hs.106747 serine carboxypeptidase 1 precursor protein /FL = gb: AF282618.1 gb: NM_021626.1 gb: AF113214.1 gb: AF265441.1 |

The following provide the gene descriptions for the top two genes identified in each separation:

Table 23 lists the top 10 genes separating Normal prostate versus all others.

TABLE 23

| Rank | Gene ID | Unigene ID | Under Expr. in Normal | AUC | Pval | FDR | Ave. Rank |
|---|---|---|---|---|---|---|---|
| 1 | 6519 | Hs.243960 | −1 | 0.886 | 0.02 | 0.025 | 1.3 |
| 2 | 3448 | Hs.169401 | 1 | 0.8629 | 0.02 | 0.012 | 4.93 |
| 3 | 17900 | Hs.8185 | −1 | 0.8601 | 0.02 | 0.0083 | 6.17 |
| 4 | 6666 | Hs.90911 | −1 | 0.8552 | 0.02 | 0.0062 | 6.59 |
| 5 | 893 | Hs.226795 | −1 | 0.8545 | 0.02 | 0.005 | 7.22 |
| 6 | 6837 | Hs.159330 | −1 | 0.8545 | 0.02 | 0.0042 | 8.05 |
| 7 | 374 | Hs.234642 | −1 | 0.8483 | 0.02 | 0.0036 | 9.69 |
| 8 | 9976 | Hs.103665 | −1 | 0.8458 | 0.02 | 0.0031 | 11.62 |
| 9 | 3520 | Hs.2794 | −1 | 0.8399 | 0.02 | 0.0028 | 15.29 |
| 10 | 3638 | Hs.74120 | −1 | 0.8357 | 0.02 | 0.0025 | 18.17 |

The top two genes from Table 23 are described in detail in Table 24.

TABLE 24

| Gene ID | Description |
|---|---|
| 6519 | gb: NM_016250.1 /DEF = *Homo sapiens* N-myc downstream-regulated gene 2 (NDRG2), mRNA. /FEA = mRNA /GEN = NDRG2 /PROD = KIAA1248 protein /DB_XREF = gi: 10280619 /UG = Hs.243960 N-myc downstream-regulated gene 2 /FL = gb: NM_016250.1 gb: AF159092. |
| 3448 | gb: N33009 /FEA = EST /DB_XREF = gi: 1153408 /DB_XREF = est: yy31f09.s1 /CLONE = IMAGE: 272873 /UG = Hs.169401 apolipoprotein E /FL = gb: BC003557.1 gb: M12529.1 gb: K00396.1 gb: NM_000041.1 |

Table 25 lists the top 10 genes separating G3 prostate cancer from all others.

TABLE 25

| Rank | Gene ID | Unigene ID | Under Expr. in G3 | AUC | Pval | FDR | Ave. rank |
|---|---|---|---|---|---|---|---|
| 1 | 18446 | Hs.283683 | −1 | 0.8481 | 1 | 1.5 | 2.14 |
| 2 | 2778 | Hs.230 | −1 | 0.8313 | 1 | 1.8 | 8.14 |
| 3 | 16102 | Hs.326526 | 1 | 0.8212 | 1 | 2.2 | 10.71 |
| 4 | 12046 | Hs.166982 | 1 | 0.817 | 1 | 2.1 | 15.14 |
| 5 | 9156 | Hs.3416 | −1 | 0.8158 | 1 | 1.8 | 14.71 |
| 6 | 9459 | Hs.128749 | −1 | 0.8158 | 1 | 1.5 | 20.43 |
| 7 | 21442 | Hs.71819 | −1 | 0.8158 | 1 | 1.3 | 13.86 |
| 8 | 6994 | Hs.180248 | −1 | 0.814 | 1 | 1.3 | 11.71 |
| 9 | 17019 | Hs.128749 | −1 | 0.8116 | 1 | 1.3 | 23.14 |
| 10 | 9457 | Hs.128749 | −1 | 0.8074 | 1 | 1.3 | 34.71 |

The top two genes listed in Table 25 are described in detail in Table 26.

TABLE 26

| Gene ID | Description |
|---|---|
| 18446 | gb: NM_020130.1 /DEF = *Homo sapiens* chromosome 8 open reading frame 4 (C8ORF4), mRNA. /FEA = mRNA /GEN = C8ORF4 /PROD = chromosome 8 open reading frame 4 /DB_XREF = gi: 9910147 /UG = Hs.283683 chromosome 8 open reading frame 4 /FL = gb: AF268037.1 gb: NM_020130.1 |
| 2778 | gb: NM_002023.2 /DEF = *Homo sapiens* fibromodulin (FMOD), mRNA. /FEA = mRNA /GEN = FMOD /PROD = fibromodulin precursor /DB_XREF = gi: 5016093 /UG = Hs.230 fibromodulin /FL = gb: NM_002023.2 |

Table 27 shows the top 10 genes separating Dysplasia from everything else.

TABLE 27

| Rank | Gene ID | Unigene ID | Under Expr. in dysplasia | AUC | Pval | FDR | Ave. rank |
|---|---|---|---|---|---|---|---|
| 1 | 5509 | Hs.178121 | −1 | 0.8336 | 0.15 | 0.15 | 4.53 |
| 2 | 4102 | Hs.75426 | −1 | 0.8328 | 0.15 | 0.075 | 4.31 |
| 3 | 10777 | Hs.101047 | 1 | 0.8319 | 0.17 | 0.058 | 5.6 |
| 4 | 18814 | Hs.319088 | 1 | 0.8189 | 0.45 | 0.11 | 10.95 |
| 5 | 4450 | Hs.154879 | 1 | 0.8168 | 0.5 | 0.1 | 11.57 |
| 6 | 14885 | Hs.2554 | 1 | 0.8164 | 0.53 | 0.088 | 18.04 |
| 7 | 10355 | Hs.169832 | 1 | 0.8126 | 0.63 | 0.089 | 14.3 |
| 8 | 5072 | Hs.122647 | −1 | 0.8063 | 0.72 | 0.091 | 26.77 |
| 9 | 3134 | Hs.323469 | −1 | 0.805 | 0.8 | 0.089 | 22.76 |
| 10 | 15345 | Hs.95011 | 1 | 0.8017 | 1 | 0.11 | 29.3 |

Table 28 provides the details for the top two genes listed in Table 27.

TABLE 28

| Gene ID | Description |
|---|---|
| 5509 | gb: NM_021647.1 /DEF = *Homo sapiens* KIAA0626 gene product (KIAA0626), mRNA. /FEA = mRNA /GEN = KIAA0626 /PROD = KIAA0626 gene product /DB_XREF = gi: 11067364 /UG = Hs.178121 KIAA0626 gene product /FL = gb: NM_021647.1 gb: AB014526.1 |
| 4102 | gb: NM_003469.2 /DEF = *Homo sapiens* secretogranin II (chromogranin C) (SCG2), mRNA. /FEA = mRNA /GEN = SCG2 /PROD = secretogranin II precursor /DB_XREF = gi: 10800415 /UG = Hs.75426 secretogranin II (chromogranin C) /FL = gb: NM_003469.2 gb: M25756.1 |

Due to the small sample sizes, poor performance was obtained with 10×10-fold cross-validation. To avoid this problem, leave-one-out cross-validation was used instead. In doing so, the average AUC for all repeats cannot be reported because there is only one test example in each repeat. Instead, the leave-one-out error rate and the pooled AUC are evaluated. However, all such pairwise separations are difficult to achieve with high accuracy and a few features.

Table 29 lists the top 10 genes separating G3 from G4. Table 30 provides the details for the top two genes listed.

TABLE 29

| Rank | Gene ID | Unigene ID | (+) Expr. in G4; (−) Expr. in G3 | AUC | Pval | FDR | Ave. rank |
|---|---|---|---|---|---|---|---|
| 1 | 19455 | Hs.26892 | −1 | 0.9057 | 0.45 | 0.45 | 1.09 |
| 2 | 11175 | Hs.137569 | −1 | 0.8687 | 1 | 1.8 | 2.95 |
| 3 | 9156 | Hs.3416 | −1 | 0.8653 | 1 | 1.4 | 4 |
| 4 | 18904 | Hs.315167 | 1 | 0.8653 | 1 | 1.1 | 4.71 |
| 5 | 9671 | Hs.98658 | 1 | 0.8636 | 1 | 0.99 | 5.45 |
| 6 | 2338 | Hs.62661 | −1 | 0.8586 | 1 | 0.96 | 6.64 |
| 7 | 2939 | Hs.82906 | 1 | 0.8586 | 1 | 0.82 | 7.46 |
| 8 | 450 | Hs.27262 | 1 | 0.8552 | 1 | 0.8 | 8.44 |
| 9 | 18567 | Hs.193602 | 1 | 0.8535 | 1 | 0.85 | 9.49 |
| 10 | 5304 | Hs.252136 | −1 | 0.8519 | 1 | 0.77 | 10.67 |

TABLE 30

| Gene ID | Description |
|---|---|
| 19455 | gb: NM_018456.1 /DEF = *Homo sapiens* uncharacterized bone marrow protein BM040 (BM040), mRNA. /FEA = mRNA /GEN = BM040 /PROD = uncharacterized bone marrow protein BM040 /DB_XREF = gi: 8922098 /UG = Hs.26892 uncharacterized bone marrow protein BM040 /FL = gb: AF217516.1 gb: NM_018456.1 |
| 11175 | gb: AB010153.1 /DEF = *Homo sapiens* mRNA for p73H, complete cds. /FEA = mRNA /GEN = p73H /PROD = p73H /DB_XREF = gi: 3445483 |

TABLE 30-continued

| Gene ID | Description |
|---|---|
| | /UG = Hs.137569 tumor protein 63 kDa with strong homology to p53 /FL = gb: AB010153.1 |

Table 31 lists the top 10 genes for separating Normal prostate from Dysplasia. Details of the top two genes for performing this separation are provided in Table 32.

TABLE 31

| Rank | Gene ID | Unigene ID | (−) Expr. in NL; (+) Expr. in Dys | AUC | Pval | FDR | Ave. rank |
|---|---|---|---|---|---|---|---|
| 1 | 4450 | Hs.154879 | −1 | 0.9037 | 0.05 | 0.05 | 1.09 |
| 2 | 10611 | Hs.41682 | 1 | 0.8957 | 0.075 | 0.037 | 2.02 |
| 3 | 9048 | Hs.177556 | −1 | 0.8743 | 0.45 | 0.15 | 3.17 |
| 4 | 18069 | Hs.103147 | −1 | 0.8717 | 0.57 | 0.14 | 4.06 |
| 5 | 7978 | Hs.20815 | −1 | 0.8583 | 1 | 0.23 | 5.56 |
| 6 | 6837 | Hs.159330 | −1 | 0.8556 | 1 | 0.21 | 6.37 |
| 7 | 7229 | Hs.71816 | −1 | 0.8463 | 1 | 0.34 | 8.03 |
| 8 | 21059 | Hs.283753 | 1 | 0.8449 | 1 | 0.3 | 9.51 |
| 9 | 15345 | Hs.95011 | −1 | 0.8436 | 1 | 0.29 | 9.94 |
| 10 | 2463 | Hs.91251 | −1 | 0.8369 | 1 | 0.38 | 11.78 |

TABLE 32

| Gene ID | Description |
|---|---|
| 4450 | gb: NM_022719.1 /DEF = *Homo sapiens* DiGeorge syndrome critical region gene DGSI (DGSI), mRNA. /FEA = mRNA /GEN = DGSI /PROD = DiGeorge syndrome critical region gene DGSIprotein /DB_XREF = gi: 13027629 /UG = Hs.154879 DiGeorge syndrome critical region gene DGSI /FL = gb: NM_022719.1 |
| 10611 | gb: U30610.1 /DEF = Human CD94 protein mRNA, complete cds. /FEA = mRNA /PROD = CD94 protein /DB_XREF = gi: 1098616 /UG = Hs.41682 killer cell lectin-like receptor subfamily D, member 1 /FL = gb: U30610.1 gb: NM_002262.2 |

Table 33 lists the top 10 genes for separating peripheral zone G4 prostate cancer from transition zone G4 cancer. Table 34 provides the details for the top two genes in this separation.

TABLE 33

| Rank | Gene ID | Unigene ID | (−) Expr. in TZ; (+) Expr. In PZ | AUC | Pval | FDR | Ave. rank |
|---|---|---|---|---|---|---|---|
| 1 | 4654 | Hs.194686 | 1 | 0.9444 | 1 | 1.2 | 1.1 |
| 2 | 14953 | Hs.306423 | 1 | 0.9306 | 1 | 1.1 | 2.45 |
| 3 | 929 | Hs.279949 | −1 | 0.9167 | 1 | 1.7 | 4 |
| 4 | 6420 | Hs.274981 | 1 | 0.9167 | 1 | 1.3 | 4.84 |
| 5 | 7226 | Hs.673 | 1 | 0.9167 | 1 | 1 | 5.69 |
| 6 | 18530 | Hs.103291 | 1 | 0.9167 | 1 | 0.86 | 6.68 |
| 7 | 6618 | Hs.2563 | 1 | 0.9097 | 1 | 1.1 | 7.82 |
| 8 | 16852 | Hs.75626 | 1 | 0.9097 | 1 | 0.93 | 8.91 |
| 9 | 19242 | Hs.12692 | 1 | 0.9097 | 1 | 0.82 | 9.78 |
| 10 | 6106 | Hs.56294 | 1 | 0.9063 | 1 | 1 | 10.75 |

TABLE 34

| Gene ID | Description |
|---|---|
| 4654 | gb: NM__003951.2 /DEF = Homo sapiens solute carrier family 25 (mitochondrial carrier, brain), member 14 (SLC25A14), transcript variant long, nuclear gene encoding mitochondrial protein, mRNA. /FEA = mRNA /GEN = SLC25A14 /PROD = solute carrier family 25, member 14, isoformUCP5L /DB__XREF = gi: 6006039 /UG = Hs.194686 solute carrier family 25 (mitochondrial carrier, brain), member 14 /FL = gb: AF155809.1 gb: AF155811.1 gb: NM__022810.1 gb: AF078544.1 gb: NM__003951.2 |
| 14953 | gb: AK002179.1 /DEF = Homo sapiens cDNA FLJ11317 fis, clone PLACE1010261, moderately similar to SEGREGATION DISTORTER PROTEIN. /FEA = mRNA /DB__XREF = gi: 7023899 /UG = Hs.306423 Homo sapiens cDNA FLJ11317 fis, clone PLACE1010261, moderately similar to SEGREGATION DISTORTER PROTEIN |

As stated in an earlier discussion, PSA is not predictive of tissue malignancy. There is very little correlation of PSA and cancer volume (R2=0.316). The R2 was also computed for PSA vs. prostate weight (0.025) and PSA vs. CA/Weight (0.323). PSA does not separate well the samples in malignancy categories. In this data, there did not appear to be any correlation between PSA and prostate weight.

A test was conducted to identify the genes most correlated with PSA, in BPH samples or in G3/4 samples, which were found to be genes 11541 for BPH and 14523 for G3/4. The details for these genes are listed below in Table 35.

TABLE 35

| Gene ID | Description |
|---|---|
| 11541 | gb: AB050468.1 /DEF = Homo sapiens mRNA for membrane glycoprotein LIG-1, complete cds. /FEA = mRNA /GEN = lig-1 /PROD = membrane glycoprotein LIG-1 /DB__XREF = gi: 13537354 /FL = gb: AB050468.1 |
| 14523 | gb: AL046992 /FEA = EST /DB__XREF = gi: 5435048 /DB__XREF = est: DKFZp586L0417__r1 /CLONE = DKFZp586L0417 /UG = Hs.184907 G protein-coupled receptor 1 /FL = gb: NM__005279.1 |
| 5626 | gb: NM__006200.1 /DEF = Homo sapiens proprotein convertase subtilisinkexin type 5 (PCSK5), mRNA. /FEA = mRNA /GEN = PCSK5 /PROD = proprotein convertase subtilisinkexin type 5 /DB__XREF = gi: 11321618 /UG = Hs.94376 proprotein convertase subtilisinkexin type 5 /FL = gb: NM__006200.1 gb: U56387.2 |

Gene 11541 shows no correlation with PSA in G3/4 samples, whereas gene 14523 shows correlation in BPH samples. Thus, 11541 is possibly the result of some overfitting due to the fact that pre-operative PSAs are available for only 7 BPH samples. Gene 14523 appears to be the most correlated gene with PSA in all samples. Gene 5626, also listed in Table 35, has good correlation coefficients ($R_{BPH}^2$=0.44, $R_{G34}^2$=0.58).

Reports are found in the published literature indicating that G Protein-coupled receptors such as gene 14523 are important in characterizing prostate cancer. See, e.g. L. L. Xu, et al. *Cancer Research* 60, 6568-6572, Dec. 1, 2000.

For comparison, genes that have "prostate specific antigen" in their description (none had PSA) were considered:

Gene 4649: gb:NM__001648.1/DEF=Homo sapiens kallikrein 3, (prostate specific antigen) (KLK3), mRNA. /FEA=mRNA /GEN=KLK3/PROD=kallikrein 3, (prostate specific antigen)/DB_XREF=gi:4502172/ UG=Hs.171995 kallikrein 3, (prostate specific antigen)/ FL=gb:BC005307.1 gb:NM__001648.1 gb:U17040.1 gb:M26663.1; and Gene 4650: gb:U17040.1/DEF=Human prostate specific antigen precursor mRNA, complete cds. /FEA=mRNA / PROD=prostate specific antigen precursor / DB_XREF=gi:595945/UG=Hs.171995 kallikrein 3, (prostate specific antigen) /FL=gb:BC005307.1 gb:NM__001648.1 gb:U17040.1 gb:M26663.1. Neither of these genes had activity that correlates with preoperative PSA.

Another test looked at finding genes whose expression correlate with cancer volume in grade 3 and 4 cancer tissues. However, even the most correlated gene is not found significant with respect to the Bonferroni-corrected pvalue (pval=0.42). Table 36 lists the top nine genes most correlated with cancer volume in G3+4 samples. The details of the top gene are provided in Table 37.

TABLE 36

| Rank | Gene ID | Unigene ID | Sign corr. | Pearson | Pval | FDR |
|---|---|---|---|---|---|---|
| 1 | 8851 | Hs.217493 | −1 | 0.6582 | 0.43 | 0.43 |
| 2 | 6892 | Hs.2868 | −1 | 0.6282 | 1 | 0.51 |
| 3 | 21353 | Hs.283803 | 1 | 0.6266 | 1 | 0.36 |
| 4 | 7731 | Hs.182507 | −1 | 0.6073 | 1 | 0.53 |
| 5 | 4853 | Hs.86958 | −1 | 0.6039 | 1 | 0.46 |
| 6 | 622 | Hs.14449 | −1 | 0.5958 | 1 | 0.48 |
| 7 | 8665 | Hs.74497 | 1 | 0.5955 | 1 | 0.41 |
| 8 | 13750 | Hs.2014 | −1 | 0.579 | 1 | 0.6 |
| 9 | 15413 | Hs.177961 | −1 | 0.5775 | 1 | 0.56 |

TABLE 37

| Gene ID | Description |
|---|---|
| 8851 | gb: M62898.1 /DEF = Human lipocortin (LIP) 2 pseudogene mRNA, complete cdslike region. /FEA = mRNA /DB__XREF = gi: 187147 /UG = Hs.217493 annexin A2 /FL = gb: M62898.1 |

A lipocortin has been described in U.S. Pat. No. 6,395,715 entitled "Uteroglobin gene therapy for epithelial cell cancer". Using RT-PCR, under-expression of lipocortin in cancer compared to BPH has been reported by Kang JS et al., *Clin Cancer Res.* 2002 January; 8(1):117-23.

EXAMPLE 6

Prostate Cancer Comparative Study of Stamey Data (12-2004)

In this example sets of genes obtained with two different data sets are compared. Both data sets were generated by Dr. Thomas A. Stamey of Stanford University, the first in 2001 using Affymetrix HuGeneFL probe arrays ("Stamey 2001"), the second in 2003 using Affymetrix U133A chip ("Stamey 2003"). After matching the genes in both arrays, a set of about 2000 common genes was used in the study. Gene selection was performed on the data of both studies independently, then the resulting gene sets were compared. A remarkable agreement was found. In addition, classifiers were trained on one dataset and tested on the other. In the separation tumor (G3/4) vs. all other tissues, classification accuracies comparable to those obtained in previous reports were obtained by cross-validation on the second study: 10% error can be achieved with 10 genes (on the independent test set of the first study); by cross-validation, there was 8% error. In the separation BPH vs. all other tissues, there was also 10% error with 10 genes. The cross-validation results for BPH were overly optimistic (only one error), however this was not unexpected since there were only 10 BPH samples in the second study.

Tables of genes were selected by consensus of both studies.

The Stamey01 (first) data set consisted of 67 samples from 26 patients. The Affymetrix HuGeneFL probe arrays used have 7129 probes, representing ~6500 genes. The composition of the 2001 dataset (number of samples in parenthesis) is summarized in Table 38. Several grades and zones are represented, however, all TZ samples are BPH (no cancer), all CZ samples are normal (no cancer). Only the PZ contains a variety of samples. Also, many samples came from the same tissues.

TABLE 38

| Zone | | Histological classification |
|---|---|---|
| CZ | (3) | NL (3) |
| PZ | (46) | NL (5) |
| | | Stroma (1) |
| | | Dysplasia (3) |
| | | G3 (10) |
| | | G4 (27) |
| TZ | (18) | BPH (18) |
| Total | 67 | |

The Stamey03 (second) dataset consisted of a matrix of 87 lines (samples) and 22283 columns (genes) obtained from an Affymetrix U133A chip. The distribution of the samples of the microarray prostate cancer study is given as been provided previously in Table 12.

Genes that had the same Gene Accession Number (GAN) in the two arrays HuGeneFL and U133A were selected. The selection was further limited to descriptions that matched reasonably well. For that purpose, a list of common words was created. A good match corresponds to a pair of description having at least one common word, excluding these common words, short words (fewer that 3 letters) and numbers. The resulting set included 2346 genes.

Because the data from both studies had previously been normalized using different methods, it was re-normalized using the routine provided below. Essentially, the data is translated and scaled, the log is taken, the lines and columns are normalized; the outlier values are squashed. This preprocessing was selected based on a visual examination of the data.

For the 2001 study, a bias of −0.08 was used. For the 2003 study, the bias was 0. Visual examination revealed that these values stabilize the variance of both classes reasonably well.

The set of 2346 genes was ranked using the data of both studies independently, with the area under the ROC curve (AUC) being used as the ranking criterion. P values were computed with the Bonferroni correction and False discovery rate (FDR) was calculated.

Both rankings were compared by examining the correlation of the AUC scores. Cross-comparisons were done by selecting the top 50 genes in one study and examining how "enriched" in those genes were the lists of top ranking genes from the other study, varying the number of genes. This can be compared to a random ranking. For a consensus ranking, the genes were ranked according to their smallest score in the two studies.

Reciprocal tests were run in which the data from one study was used for training of the classifier which was then tested on the data from the other study. Three different classifiers were used: Linear SVM, linear ridge regression, and Golub's classifier (analogous to Naïve Bayes). For every test, the features selected with the training set were used. For comparison, the consensus features were also used.

Separation of all tumor samples (G3 and G4) from all others was performed, with the G3 and G4 samples being grouped into the positive class and all samples grouped into the negative class. The top 200 genes in each study of Tumor G3/4 vs. others are listed in the tables in FIGS. 5a-5o for the 2001 study and the 2003 study. The genes were ranked in two ways, using the data of the first study (2001) and using the data of the second study (2003)

Most genes ranking high in one study also rank high in the other, with some notable exceptions. These exceptions may correspond to probes that do not match in both arrays even though their gene identification and descriptions match. They may also correspond to probes that "failed" to work in one array.

Table 39 lists the top 50 genes resulting from the feature ranking by consensus between the 2001 study and the 2003 study Tumor G3/4 vs. others. A listing of the top 200 genes, including the 50 genes in Table 39, is provided in FIGS. 6a-6g. Ranking was performed according to a score that is the minimum of score0 and score1.

TABLE 39

| Rk | Unigene ID | Over Expr | Scor | Rk0 | Score0 | Rk1 | Score1 | Description |
|---|---|---|---|---|---|---|---|---|
| 1 | Hs.195850 | −1 | 0.8811 | 7 | 0.8811 | 2 | 0.8813 | Human keratin type II (58 kD) mRNA |
| 2 | Hs.171731 | −1 | 0.8754 | 1 | 0.9495 | 3 | 0.8754 | Human RACH1 (RACH1) mRNA |
| 3 | Hs.65029 | −1 | 0.8647 | 8 | 0.8802 | 5 | 0.8647 | Human gas1 gene |
| 4 | Hs.771 | −1 | 0.8532 | 15 | 0.8532 | 1 | 0.8953 | Human liver glycogen phosphorylase mRNA |
| 5 | Hs.79217 | 1 | 0.8532 | 16 | 0.8532 | 7 | 0.855 | Human pyrroline 5-carboxylate reductase mRNA |
| 6 | Hs.198760 | −1 | 0.8495 | 19 | 0.8495 | 4 | 0.869 | *H. sapiens* NF-H gene |
| 7 | Hs.174151 | −1 | 0.8448 | 4 | 0.8892 | 10 | 0.8448 | Human aldehyde oxidase (hAOX) mRNA |
| 8 | Hs.44 | −1 | 0.841 | 12 | 0.8685 | 14 | 0.841 | Human nerve growth factor (HBNF-1) mRNA |
| 9 | Hs.3128 | 1 | 0.841 | 2 | 0.9081 | 15 | 0.841 | Human RNA polymerase II subunit (hsRPB8) mRNA |
| 10 | Hs.34853 | −1 | 0.8314 | 5 | 0.8892 | 20 | 0.8314 | Human Id-related helix-loop-helix protein Id4 mRNA |
| 11 | Hs.113 | −1 | 0.8217 | 13 | 0.8658 | 24 | 0.8217 | Human cytosolic epoxide hydrolase mRNA |
| 12 | Hs.1813 | −1 | 0.8201 | 31 | 0.827 | 25 | 0.8201 | *Homo sapiens* synaptic vesicle amine transporter (SVAT) mRNA |
| 13 | Hs.2006 | −1 | 0.8099 | 40 | 0.8099 | 23 | 0.8255 | Human glutathione transferase M3 (GSTM3) mRNA |

TABLE 39-continued

| Rk | Unigene ID | Over Expr | Scor | Rk0 | Score0 | Rk1 | Score1 | Description |
|---|---|---|---|---|---|---|---|---|
| 14 | Hs.76224 | −1 | 0.8083 | 28 | 0.836 | 39 | 0.8083 | Human extracellular protein (S1-5) mRNA |
| 15 | Hs.27311 | 1 | 0.8056 | 11 | 0.8694 | 42 | 0.8056 | Human transcription factor SIM2 long form mRNA |
| 16 | Hs.77546 | −1 | 0.8008 | 14 | 0.8649 | 46 | 0.8008 | Human mRNA for KIAA0172 gene |
| 17 | Hs.23838 | 1 | 0.7982 | 50 | 0.7982 | 22 | 0.8287 | Human neuronal DHP-sensitive |
| 18 | Hs.10755 | −1 | 0.7955 | 53 | 0.7955 | 17 | 0.8373 | Human mRNA for dihydropyrimidinase |
| 19 | Hs.2785 | −1 | 0.7911 | 24 | 0.8414 | 51 | 0.7911 | *H. sapiens* gene for cytokeratin 17 |
| 20 | Hs.86978 | 1 | 0.7748 | 75 | 0.7748 | 70 | 0.7777 | *H. sapiens* mRNA for prolyl oligopeptidase |
| 21 | Hs.2025 | −1 | 0.7744 | 3 | 0.9027 | 73 | 0.7744 | Human transforming growth factor-beta 3 (TGF-beta3) mRNA |
| 22 | Hs.30054 | 1 | 0.7734 | 45 | 0.8054 | 74 | 0.7734 | Human coagulation factor V mRNA |
| 23 | Hs.155591 | −1 | 0.7723 | 52 | 0.7973 | 76 | 0.7723 | Human forkhead protein FREAC-1 mRNA |
| 24 | Hs.237356 | −1 | 0.7712 | 81 | 0.7712 | 61 | 0.7846 | Human intercrine-alpha (hIRH) mRNA |
| 25 | Hs.211933 | −1 | 0.7707 | 70 | 0.7784 | 80 | 0.7707 | Human (clones HT-[125 |
| 26 | Hs.75746 | 1 | 0.7691 | 78 | 0.7721 | 81 | 0.7691 | Human aldehyde dehydrogenase 6 mRNA |
| 27 | Hs.155597 | −1 | 0.7676 | 85 | 0.7676 | 78 | 0.7712 | Human adipsin/complement factor D mRNA |
| 28 | Hs.75111 | −1 | 0.7669 | 21 | 0.8432 | 85 | 0.7669 | Human cancellous bone osteoblast mRNA for serin protease with IGF-binding motif |
| 29 | Hs.75137 | −1 | 0.7664 | 37 | 0.8108 | 86 | 0.7664 | Human mRNA for KIAA0193 gene |
| 30 | Hs.76307 | −1 | 0.7658 | 86 | 0.7658 | 12 | 0.841 | Human mRNA for unknown product |
| 31 | Hs.79059 | −1 | 0.7653 | 44 | 0.8063 | 87 | 0.7653 | Human transforming growth factor-beta type III receptor (TGF-beta) mRNA |
| 32 | Hs.1440 | 1 | 0.7632 | 36 | 0.8108 | 92 | 0.7632 | Human gamma amino butyric acid (GABAA) receptor beta-3 subunit mRNA |
| 33 | Hs.66052 | −1 | 0.7626 | 60 | 0.7883 | 93 | 0.7626 | 1299-1305 |
| 34 | Hs.155585 | −1 | 0.7626 | 6 | 0.8838 | 94 | 0.7626 | Human transmembrane receptor (ror2) mRNA |
| 35 | Hs.153322 | −1 | 0.7589 | 35 | 0.8126 | 98 | 0.7589 | Human mRNA for phospholipase C |
| 36 | Hs.77448 | −1 | 0.7583 | 87 | 0.7658 | 99 | 0.7583 | Human pyrroline-5-carboxylate dehydrogenase (P5CDh) mRNA |
| 37 | Hs.190787 | −1 | 0.7568 | 94 | 0.7568 | 69 | 0.7782 | Human tissue inhibitor of metalloproteinase 4 mRNA |
| 38 | Hs.172851 | −1 | 0.7567 | 48 | 0.8 | 101 | 0.7567 | Human arginase type II mRNA |
| 39 | Hs.85146 | −1 | 0.7562 | 20 | 0.8459 | 103 | 0.7562 | Human erythroblastosis virus oncogene homolog 2 (ets-2) mRNA |
| 40 | Hs.10526 | −1 | 0.7556 | 17 | 0.8532 | 105 | 0.7556 | Human smooth muscle LIM protein (h-SmLIM) mRNA |
| 41 | Hs.81412 | −1 | 0.7551 | 61 | 0.7865 | 106 | 0.7551 | Human mRNA for KIAA0188 gene |
| 42 | Hs.180107 | 1 | 0.7541 | 96 | 0.7541 | 44 | 0.8024 | Human mRNA for DNA polymerase beta |
| 43 | Hs.245188 | −1 | 0.7519 | 56 | 0.7937 | 113 | 0.7519 | Human tissue inhibitor of metalloproteinases-3 mRNA |
| 44 | Hs.56145 | 1 | 0.7508 | 55 | 0.7946 | 114 | 0.7508 | Human mRNA for NB thymosin beta |
| 45 | Hs.620 | −1 | 0.7497 | 18 | 0.8523 | 115 | 0.7497 | Human bullous pemphigoid antigen (BPAG1) mRNA |
| 46 | Hs.83450 | −1 | 0.7495 | 101 | 0.7495 | 67 | 0.7803 | *Homo sapiens* laminin-related protein (LamA3) mRNA |
| 47 | Hs.687 | −1 | 0.7495 | 102 | 0.7495 | 26 | 0.8195 | Human lung cytochrome P450 (IV subfamily) BI protein |
| 48 | Hs.75151 | 1 | 0.7486 | 104 | 0.7486 | 8 | 0.8545 | Human GTPase activating protein (rap1GAP) mRNA |
| 49 | Hs.283749 | −1 | 0.7468 | 106 | 0.7468 | 110 | 0.7524 | Human mRNA for RNase 4 |
| 50 | Hs.74566 | −1 | 0.7433 | 26 | 0.8369 | 125 | 0.7433 | Human mRNA for dihydro-pyrimidinase related protein-3 |

Training of the classifier was done with the data of one study while testing used the data of the other study. The results are similar for the three classifiers that were tried: SVM, linear ridge regression and Golub classifier. Approximately 90% accuracy can be achieved in both cases with about 10 features. Better "cheating" results are obtained with the consensus features. This serves to validate the consensus features, but the performances cannot be used to predict the accuracy of a classifier on new data. An SVM was trained using the two best features of the 2001 study and the sample of the 2001 study as the training data. The samples from the 2003 study were used as test data to achieve an error rate of 16% is achieved. The tumor and non-tumor samples are well separated, but that, in spite of normalization, the distributions of the samples is different between the two studies.

The definitions of the statistics used in the various rankings are provided in Table 40.

TABLE 40

| Statistic | Description |
|---|---|
| AUC | Area under the ROC curve of individual genes, using training tissues. The ROC curve (receiver operating characteristic) is a plot of the sensitivity (error rate of the "positive" class) vs. the specificity (error rate of the "negative" class). Insignificant genes have an AUC close to 0.5. Genes with an AUC closer to one are overexpressed in cancer. Genes with an AUC closer to zero are underexpressed. |
| pval | Pvalue of the AUC, used as a test statistic to test the equality of the median of the two population (cancer and non-cancer.) The AUC is the Mann-Withney statistic. The test is equivalent to the Wilcoxon rank sum test. Small pvalues shed doubt on the null hypothesis of equality of the medians. Hence smaller values are better. To account to the multiple testing the pvalue may be Bonferroni corrected by multiplying it by the number of genes 7129. |
| FDR | False discovery rate of the AUC ranking. An estimate of the fraction of insignificant genes in the genes ranking higher than a given gene. It is equal the pvalue multiplied by the number of genes 7129 and divided by the rank. |
| Fisher | Fisher statistic characterizing the multiclass discriminative power for the histological classes (normal, BPH, dysplasia, grade 3, and grade 4.) The Fisher statistic is the ratio of the between-class variance to the within-class variance. Higher values indicate better discriminative power. The Fisher statistic can be interpreted as a signal to noise ratio. It is computed with training data only. |
| Pearson | Pearson correlation coefficient characterizing "disease progression", with histological classes coded as 0 = normal, 1 = BPH, 2 = dysplasia, 3 = grade 3, and 4 = grade 4.) A value close to 1 indicates a good correlation with disease progression. |
| FC | Fold change computed as the ratio of the average cancer expression values to the avarage of the other expression values. It is computed with training data only. A value near one indicates an insignificant gene. A large value indicates a gene overexpressed in cancer; a small value an underexpressed gene. |
| Mag | Gene magnitude. The average of the largest class expression value (cancer or other) relative to that of the ACTB housekeeping gene. It is computed with training data only. |
| tAUC | AUC of the genes matched by probe and or description in the test set. It is computed with test data only, hence not all genes have a tAUC. |

EXAMPLE 7

Genes Underexpressed in Prostate Cancer

DNA methylation plays an important role in determining whether some genes are expressed or not. By turning genes off that are not needed, DNA methylation is an essential control mechanism for the normal development and functioning of organisms. Alternatively, abnormal DNA methylation is one of the mechanisms underlying the changes observed with aging and development of many cancers.

Cancers have historically been linked to genetic changes caused by chromosomal mutations within the DNA. Mutations, hereditary or acquired, can lead to the loss of expression of genes critical for maintaining a healthy state. Evidence now supports that a relatively large number of cancers are caused by inappropriate DNA methylation, frequently near DNA mutations. In many cases, hyper-methylation of DNA incorrectly switches off critical genes, such as tumor suppressor genes or DNA repair genes, allowing cancers to develop and progress. This non-mutational process for controlling gene expression is described as epigenetics.

Because genes that are hypermethylated in tumor cells are strongly specific to the tissue of origin of the tumor, detection of such genes can be used to improve cancer detection, the assessment of cancer risk and response to therapy. DNA is stable and is found intact in readily available fluids (e.g., serum, sputum, semen, blood, and urine) and paraffin embedded tissues, which could lead to development of relatively simple yet highly specific tests for cancer. Because the abnormal DNA methylation contributes to gene silencing, it is desirable to identify genes that are underexpressed, or down-regulated, in cancer in a microarray gene expression analysis.

The following example used RFE to identify genes that are underexpressed in cancer and, therefore, could be used for either DNA methylation- or microarray-based tests for screening, predicting and/or monitoring prostate cancer.

Figure 7:
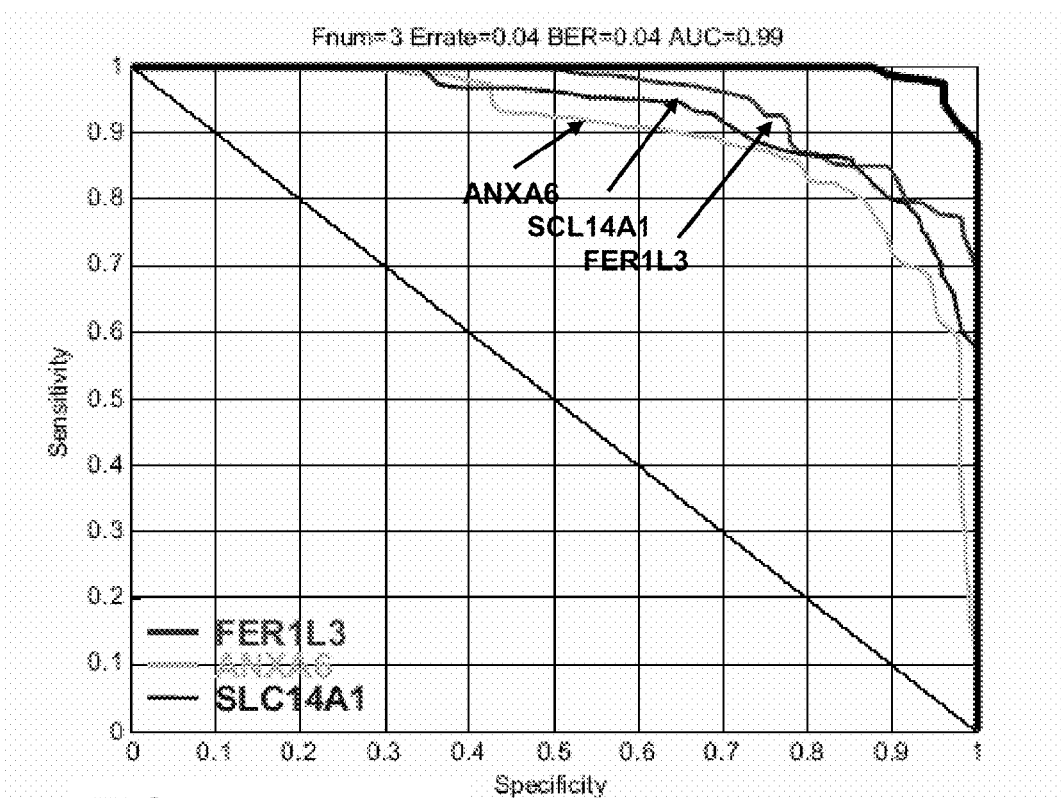
FIG. 7 is a plot of the ROC curves for each of the three top genes underexpressed in prostate cancer and the ROC of the combination (black) on training data
Figure 8:
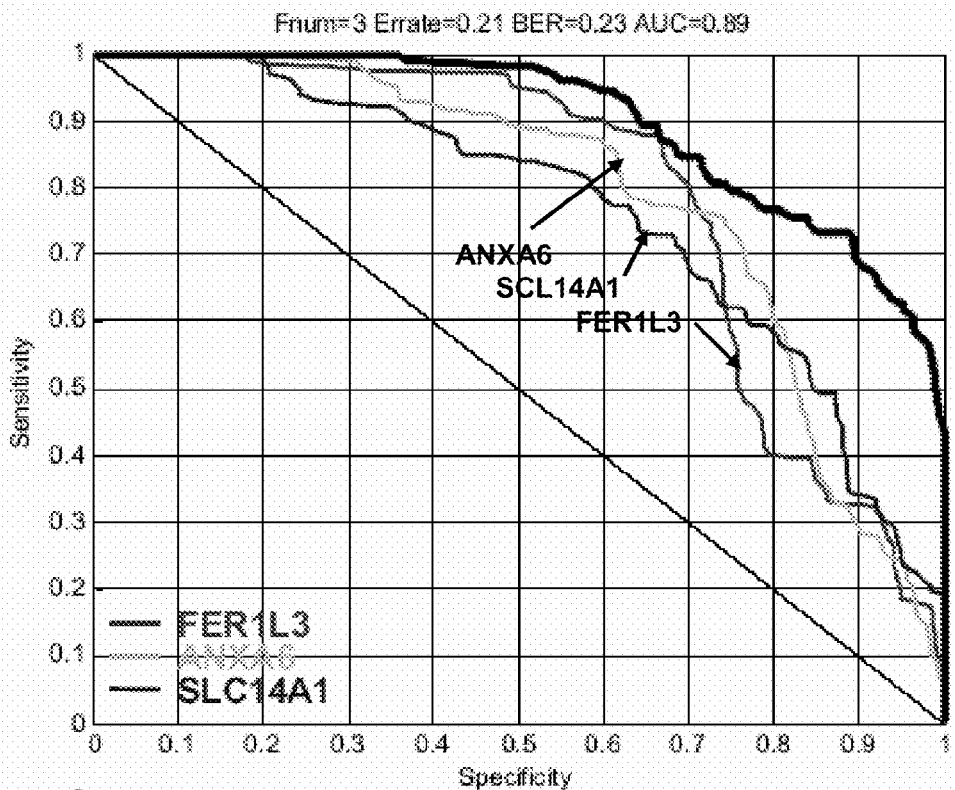
FIG. 8 is a plot of the ROC curves for the 3 top selected genes (color) and the ROC of the combination (black) on test data.

Table 41 lists the 33 top underexpressed ranked genes selected from the table provided in FIG. 4 (see also Table 18 above). Training of the regularized classifier was performed using the Stamey03 dataset (Table 12.) Testing was performed using the ONCOMINE data. (ONCOMINE, on the World Wide Web at oncomine.org, is a cancer microarray database and data-mining platform contains the entire dataset from eight prostate cancer microarray analyses published to date in worldwide scientific literature, comprising 135 normal prostate and 212 prostate adenocarcinoma samples.) The three top ranking genes obtained by RFE yield AUC=0.89. Those genes are SLC14A1 (SEQ ID NO. 1), FER1L3 (SEQ ID NO. 2), and ANXA6 (SEQ ID NO. 3). (See Table 42.) These genes perform well individually, each with an AUC of 0.86 or better, but their combination outperforms any individual gene, as indicated by the dark black line (uppermost) in both FIG. 7 and FIG. 8. The top 3 genes also outperformed a combination of four genes consisting of the three identified above plus GSTP1, which has been reported by Nelson et al. (U.S. Pat. No. 5,552,277, incorporated herein by reference) as a biomarker for diagnosis of prostate cancer. The combination of four genes yielded an AUC of 0.86.

TABLE 41

| Rank* | Gene ID | Unigene ID | AUC FC | Gene Symbol | Gene Title | Description | GenBank |
|---|---|---|---|---|---|---|---|
| 4 | 11911 | Hs.279009 | 0.9253 0.59 | MGP | matrix Gla protein | Matrix Gla protein gb: BC000454.1 /DEF = *Homo sapiens*, calmodulin 2 (phosphorylase kinase, delta), clone MGC: 8460, mRNA, complete cds. | NM_000900 |

TABLE 41-continued

| Rank* | Gene ID | Unigene ID | AUC FC | Gene Symbol | Gene Title | Description | GenBank |
|---|---|---|---|---|---|---|---|
| | | | | | | /FEA = mRNA /PROD = calmodulin 2 (phosphorylase kinase, delta) /DB_XREF = gi: 12653368 /UG = Hs.182278 calmodulin 2 (phosphorylase kinase, delta) /FL = gb: BC000454.1 | |
| 6 | 983 | Hs.226795 | 0.9076 0.54 | GSTP1 | glutathione S-transferase pi | gb: NM_000852.2 /DEF = Homo sapiens glutathione S-transferase pi (GSTP1), mRNA. /FEA = mRNA /GEN = GSTP1 /PROD = glutathione transferase /DB_XREF = gi: 6552334 /UG = Hs.226795 glutathione S-transferase pi /FL = gb: U62589.1 gb: U30897.1 gb: NM_000852.2 | NM_000852 |
| 9 | 19589 | Hs.45140 | 0.9033 0.49 | TMEM35 | transmembrane protein 35 | gb: NM_021637.1 /DEF = Homo sapiens hypothetical protein FLJ14084 (FLJ14084), mRNA. /FEA = mRNA /GEN = FLJ14084 /PROD = hypothetical protein FLJ14084 /DB_XREF = gi: 11056011 /UG = Hs.45140 hypothetical protein FLJ14084 /FL = gb: NM_021637.1 | NM_021637 |
| 10 | 6519 | Hs.243960 | 0.8996 0.47 | NDRG2 | NDRG family member 2 | gb: NM_016250.1 /DEF = Homo sapiens N-myc downstream-regulated gene 2 (NDRG2), mRNA. /FEA = mRNA /GEN = NDRG2 /PROD = KIAA1248 protein /DB_XREF = gi: 10280619 /UG = Hs.243960 N-myc downstream-regulated gene 2 /FL = gb: NM_016250.1 gb: AF159092.3 | NM_016250 |
| 12 | 18122 | Hs.106747 | 0.8985 0.61 | SCPEP1 | serine carboxypeptidase 1 | gb: NM_021626.1 /DEF = Homo sapiens serine carboxypeptidase 1 precursor protein (HSCP1), mRNA. /FEA = mRNA /GEN = HSCP1 /PROD = serine carboxypeptidase 1 precursor protein /DB_XREF = gi: 11055991 /UG = Hs.106747 serine carboxypeptidase 1 precursor protein /FL = gb: AF282618.1 gb: NM_021626.1 gb: AF113214.1 gb: AF265441.1 | NM_021626 |
| 13 | 18237 | Hs.283719 | 0.8961 | BEX1 | brain expressed, X-linked 1 | gb: NM_018476.1 /DEF = Homo sapiens uncharacterized hypothalamus protein HBEX2 (HBEX2), mRNA. /FEA = mRNA /GEN = HBEX2 /PROD = uncharacterized hypothalamus protein HBEX2 /DB_XREF = gi: 8923715 /UG = Hs.283719 uncharacterized hypothalamus protein HBEX2 /FL = gb: AF220189.1 gb: NM_018476.1 gb: AF183416.1 gb: AF237783.1 | NM_018476 |
| 14 | 3059 | Hs.771 | 0.8942 | PYGL | phosphorylase, glycogen; liver (Hers disease, glycogen storage disease type VI) | gb: NM_002863.1 /DEF = Homo sapiens phosphorylase, glycogen; liver (Hers disease, glycogen storage disease type VI) (PYGL), mRNA. /FEA = mRNA /GEN = PYGL /PROD = phosphorylase, glycogen; liver (Hers disease, glycogen storage disease type VI) /DB_XREF = gi: 4506352 /UG = Hs.771 phosphorylase, glycogen; liver (Hers disease, glycogen storage disease type VI) /FL = gb: M14636.1 gb: AF066858.1 gb: AF046785.1 gb: NM_002863.1 | NM_002863 |
| 16 | 18598 | Hs.9728 | 0.8904 | ARMCX1 | armadillo repeat containing, X-linked 1 | gb: NM_016608.1 /DEF = Homo sapiens ALEX1 protein (LOC51309), mRNA. /FEA = mRNA /GEN = LOC51309 /PROD = ALEX1 protein /DB_XREF = gi: 7706142 /UG = Hs.9728 ALEX1 protein /FL = gb: AF248963.1 gb: BC002691.1 gb: AB039670.1 gb: NM_016608.1 | NM_016608 |
| 17 | 12434 | Hs.250723 | 0.8899 | FRAP1 | FK506 binding protein 12-rapamycin associated protein 1 | gb: U88966.1 /DEF = Human protein rapamycin associated protein (FRAP2) gene, complete cds. /FEA = mRNA /GEN = FRAP2 /PROD = rapamycin associated protein FRAP2 /DB_XREF = gi: 3282238 /UG = Hs.250723 FK506 binding protein 12-rapamycin | NM_004958 |

TABLE 41-continued

| Rank* | Gene ID | Unigene ID | AUC FC | Gene Symbol | Gene Title | Description | GenBank |
|---|---|---|---|---|---|---|---|
| 18 | 4922 | Hs.55279 | 0.884 | SERPINB5 | serpin peptidase inhibitor, clade B (ovalbumin), member 5 | associated protein 1 /FL = gb: U88966.1 gb: NM__004958.1 gb: L34075.1 gb: NM__002639.1 /DEF = Homo sapiens serine (or cysteine) proteinase inhibitor, clade B (ovalbumin), member 5 (SERPINB5), mRNA. /FEA = mRNA /GEN = SERPINB5 /PROD = serine (or cysteine) proteinase inhibitor, clade B (ovalbumin), member 5 /DB__XREF = gi: 4505788 /UG = Hs.55279 serine (or cysteine) proteinase inhibitor, clade B (ovalbumin), member 5 /FL = gb: NM__002639.1 gb: U04313.1 | NM__002639 |
| 20 | 9976 | Hs.103665 | 0.8824 | VILL | villin-like | gb: BC004300.1 /DEF = Homo sapiens, Similar to villin-like, clone MGC: 10896, mRNA, complete cds. /FEA = mRNA /PROD = Similar to villin-like /DB__XREF = gi: 13279166 /UG = Hs.103665 villin-like /FL = gb: BC004300.1 | NM__015873 BC004300 |
| 22 | 3331 | Hs.54697 | 0.8802 | ARHGEF9 | Cdc42 guanine nucleotide exchange factor (GEF) 9 | Consensus includes gb: AI625739 /FEA = EST /DB__XREF = gi: 4650670 /DB__XREF = est: ty65g05.x1 /CLONE = IMAGE: 2283992 /UG = Hs.54697 Cdc42 guanine exchange factor (GEF) 9 /FL = gb: NM__015185.1 | NM__015185 |
| 26 | 4497 | Hs.33084 | 0.8776 | SLC2A5 | solute carrier family 2 (facilitated glucose/fructose transporter), member 5 | Consensus includes gb: BE560461 /FEA = EST /DB__XREF = gi: 9804181 /DB__XREF = est: 601346729F1 /CLONE = IMAGE: 3687631 /UG = Hs.33084 solute carrier family 2 (facilitated glucose transporter), member 5 /FL = gb: BC001820.1 gb: BC001692.1 gb: M55531.1 gb: NM__003039.1 | NM__003039 |
| 28 | 9765 | Hs.22599 | 0.8765 | MAGI2 | membrane associated guanylate kinase, WW and PDZ domain containing 2 | gb: NM__012301.1 /DEF = Homo sapiens atrophin-1 interacting protein 1; activin receptor interacting protein 1 (KIAA0705), mRNA. /FEA = mRNA /GEN = KIAA0705 /PROD = atrophin-1 interacting protein 1; activinreceptor interacting protein 1 /DB__XREF = gi: 6912461 /UG = Hs.22599 atrophin-1 interacting protein 1; activin receptor interacting protein 1 /FL = gb: AF038563.1 gb: NM__012301.1 | NM__012301 |
| 29 | 4479 | Hs.198760 | 0.8759 | NEFH | neurofilament, heavy polypeptide 200 kDa | gb: NM__021076.1 /DEF = Homo sapiens neurofilament, heavy polypeptide (200 kD) (NEFH), mRNA. /FEA = mRNA /GEN = NEFH /PROD = neurofilament, heavy polypeptide (200 kD) /DB__XREF = gi: 10835088 /UG = Hs.198760 neurofilament, heavy polypeptide (200 kD) /FL = gb: NM__021076.1 gb: AF203032.1 | NM__021076 |
| 30 | 239 | Hs.198760 | 0.8749 | NEFH | neurofilament, heavy polypeptide 200 kDa | gb: NM__021076.1 /DEF = Homo sapiens neurofilament, heavy polypeptide (200 kD) (NEFH), mRNA. /FEA = mRNA /GEN = NEFH /PROD = neurofilament, heavy polypeptide (200 kD) /DB__XREF = gi: 10835088 /UG = Hs.198760 neurofilament, heavy polypeptide (200 kD) /FL = gb: NM__021076.1 gb: AF203032.1 | NM__021076 |
| 31 | 6666 | Hs.90911 | 0.8749 | SLC16A5 | solute carrier family 16, member 5 (monocarboxylic acid transporter 6) | gb: NM__004695.1 /DEF = Homo sapiens solute carrier family 16 (monocarboxylic acid transporters), member 5 (SLC16A5), mRNA. /FEA = mRNA /GEN = SLC16A5 /PROD = solute carrier family 16 (monocarboxylic acidtransporters), member 5 /DB__XREF = gi: 4759115 /UG = Hs.90911 solute carrier family 16 (monocarboxylic acid transporters), member 5 /FL = gb: U59299.1 gb: NM__004695.1 | NM__004695 |
| 32 | 12655 | Hs.10587 | 0.8749 | DMN | desmuslin | Consensus includes gb: AK026420.1 /DEF = Homo sapiens cDNA: FLJ22767 fis, clone KAIA1191. /FEA = mRNA | NM__015286 NM__145728 |

TABLE 41-continued

| Rank* | Gene ID | Unigene ID | AUC FC | Gene Symbol | Gene Title | Description | GenBank |
|---|---|---|---|---|---|---|---|
| 34 | 5923 | Hs.171731 | 0.8738 0.24 | SLC14A1 | solute carrier family 14 (urea transporter), member 1 (Kidd blood group) | /DB_XREF = gi: 10439281 /UG = Hs.10587 KIAA0353 protein gb: NM_015865.1 /DEF = *Homo sapiens* solute carrier family 14 (urea transporter), member 1 (SLC14A1), mRNA. /FEA = mRNA /GEN = SLC14A1 /PROD = RACH1 /DB_XREF = gi: 7706676 /UG = Hs.171731 solute carrier family 14 (urea transporter), member 1 (Kidd blood group) /FL = gb: U35735.1 gb: NM_015865.1 | NM_015865 |
| 35 | 1889 | Hs.195850 | 0.8727 | KRT5 | keratin 5 (epidermolysis bullosa simplex, Dowling-Meara/Kobner/Weber-Cockayne types) | gb: NM_000424.1 /DEF = *Homo sapiens* keratin 5 (epidermolysis bullosa simplex, Dowling-MearaKobnerWeber-Cockayne types) (KRT5), mRNA. /FEA = mRNA /GEN = KRT5 /PROD = keratin 5 (epidermolysis bullosa simplex, Dowling-MearaKobnerWeber-Cockayne types) /DB_XREF = gi: 4557889 /UG = Hs.195850 keratin 5 (epidermolysis bullosa simplex, Dowling-MearaKobnerWeber-Cockayne types) /FL = gb: M21389.1 gb: NM_000424.1 | NM_000424 |
| 36 | 21568 | Hs.111676 | 0.8716 | HSPB8 | heat shock 22 kDa protein 8 | gb: AF133207.1 /DEF = *Homo sapiens* protein kinase (H11) mRNA, complete cds. /FEA = mRNA /GEN = H11 /PROD = protein kinase /DB_XREF = gi: 5901654 /UG = Hs.111676 protein kinase H11; small stress protein-like protein HSP22 /FL = gb: AF133207.1 | NM_014365 AF133207 |
| 38 | 14738 | Hs.8198 | 0.8706 | ZNF204 | zinc finger protein 204 | Consensus includes gb: AF033199.1 /DEF = *Homo sapiens* C2H2 zinc finger protein pseudogene, mRNA sequence. /FEA = mRNA /DB_XREF = gi: 3252864 /UG = Hs.8198 zinc finger protein 204 | NR_002722 |
| 39 | 1867 | Hs.234680 | 0.8695 0.52 | FER1L3 | fer-1-like 3, myoferlin (*C. elegans*) | gb: NM_013451.1 /DEF = *Homo sapiens* fer-1 (*C. elegans*)-like 3 (myoferlin) (FER1L3), mRNA. /FEA = mRNA /GEN = FER1L3 /PROD = fer-1 (*C. elegans*)-like 3 (myoferlin) /DB_XREF = gi: 7305052 /UG = Hs.234680 fer-1 (*C. elegans*)-like 3 (myoferlin) /FL = gb: AF182316.1 gb: NM_013451.1 | NM_013451 |
| 40 | 4467 | Hs.24587 | 0.8695 | EFS | embryonal Fyn-associated substrate | gb: NM_005864.1 /DEF = *Homo sapiens* signal transduction protein (SH3 containing) (EFS2), mRNA. /FEA = mRNA /GEN = EFS2 /PROD = signal transduction protein (SH3 containing) /DB_XREF = gi: 5031680 /UG = Hs.24587 signal transduction protein (SH3 containing) /FL = gb: AB001466.1 gb: NM_005864.1 | NM_005864 |
| 41 | 9614 | Hs.8583 | 0.8695 | APOBEC3C | apolipoprotein B mRNA editing enzyme, catalytic polypeptide-like 3C | gb: AF165520.1 /DEF = *Homo sapiens* phorbolin I protein (PBI) mRNA, complete cds. /FEA = mRNA /GEN = PBI /PROD = phorbolin I protein /DB_XREF = gi: 9294746 /UG = Hs.8583 similar to APOBEC1 /FL = gb: AF165520.1 | NM_014508 |
| 43 | 20137 | Hs.249727 | 0.8692 | FBXO17 | F-box protein 17 | gb: NM_024907.1 /DEF = *Homo sapiens* hypothetical protein FLJ11798 (FLJ11798), mRNA. /FEA = mRNA /GEN = FLJ11798 /PROD = hypothetical protein FLJ11798 /DB_XREF = gi: 13376364 /UG = Hs.249727 hypothetical protein FLJ11798 /FL = gb: NM_024907.1 | NM_024907 |
| 44 | 12023 | Hs.74034 | 0.869 | CAV1 | caveolin 1, caveolae protein, 22 kDa | Consensus includes gb: AU147399 /FEA = EST /DB_XREF = gi: 11008920 /DB_XREF = est: AU147399 /CLONE = MAMMA1000563 /UG = Hs.74034 *Homo sapiens* clone 24651 mRNA sequence | NM_001753 |

TABLE 41-continued

| Rank* | Gene ID | Unigene ID | AUC FC | Gene Symbol | Gene Title | Description | GenBank |
|---|---|---|---|---|---|---|---|
| 45 | 12435 | Hs.82432 | 0.869 | GPD1L | glycerol-3-phosphate dehydrogenase 1-like | Consensus includes gb: AA135522 /FEA = EST /DB_XREF = gi: 1696570 /DB_XREF = est: zl09d08.s1 /CLONE = IMAGE: 501423 /UG = Hs.82432 KIAA0089 protein | NM_015141 |
| 47 | 7082 | Hs.95197 | 0.8684 | ALDH1A2 | aldehyde dehydrogenase 1 family, member A2 | gb: NM_003888.1 /DEF = Homo sapiens retinaldehyde dehydrogenase 2 (RALDH2), mRNA. /FEA = mRNA /GEN = RALDH2 /PROD = retinaldehyde dehydrogenase 2 /DB_XREF = gi: 10835044 /UG = Hs.95197 aldehyde dehydrogenase 1 family, member A2 /FL = gb: NM_003888.1 gb: AB015226.1 gb: AB015227.1 gb: AB015228.1 | NM_003888 |
| 50 | 4361 | Hs.102 | 0.8673 | AMT | aminomethyl transferase | gb: NM_000481.1 /DEF = Homo sapiens aminomethyltransferase (glycine cleavage system protein T) (AMT), mRNA. /FEA = mRNA /GEN = AMT /PROD = aminomethyltransferase (glycine cleavage systemprotein T) /DB_XREF = gi: 4502082 /UG = Hs.102 aminomethyltransferase (glycine cleavage system protein T) /FL = gb: D13811.1 gb: NM_000481.1 | NM_000481 |
| 51 | 18392 | Hs.1227 | 0.8671 | ALAD | aminolevulinate, delta-, dehydratase | gb: BC000977.1 /DEF = Homo sapiens, aminolevulinate, delta-, dehydratase, clone MGC: 5057, mRNA, complete cds. /FEA = mRNA /PROD = aminolevulinate, delta-, dehydratase /DB_XREF = gi: 12654312 /UG = Hs.1227 aminolevulinate, delta-, dehydratase /FL = gb: BC000977.1 gb: M13928.1 gb: NM_000031.1 | NM_000031 |
| 52 | 5199 | Hs.118127 | 0.8657 | ACTC1 | actin, alpha, cardiac muscle 1 | gb: NM_005159.2 /DEF = Homo sapiens actin, alpha, cardiac muscle (ACTC), mRNA. /FEA = mRNA /GEN = ACTC /PROD = actin, alpha, cardiac muscle precursor /DB_XREF = gi: 10938011 /UG = Hs.118127 actin, alpha, cardiac muscle /FL = gb: NM_005159.2 | NM_005159 |
| 64 | 1051 | Hs.118796 | 0.862 | ANXA6 | annexin A6 | gb: NM_001155.2 /DEF = Homo sapiens annexin A6 (ANXA6), transcript variant 1, mRNA. /FEA = mRNA /GEN = ANXA6 /PROD = annexin VI isoform 1 /DB_XREF = gi: 4809274 /UG = Hs.118796 annexin A6 /FL = gb: J03578.1 gb: D00510.1 gb: NM_001155.2 | NM_001155 |

*Rank: from overall prostate marker table (FIG. 4)
FC = fold change

TABLE 42

| Rank | Gene ID | Unigene ID archival/current | AUC | Gene Symbol | Solubility | Gene Title | Description | GenBank SEQIDNO. |
|---|---|---|---|---|---|---|---|---|
| 34 | 5923 | Hs.171731 Hs.101307 | 0.8738 | SLC14A1 | Blood | solute carrier family 14 (urea transporter), member 1 (Kidd blood group) | gb: NM_015865.1 /DEF = Homo sapiens solute carrier family 14 (urea transporter), member 1 (Kidd blood group) (SLC14A1), mRNA. /FEA = mRNA /GEN = SLC14A1 /PROD = RACH1 /DB_XREF = gi: 7706676 /UG = Hs.171731 solute carrier family 14 (urea transporter), member 1 (Kidd blood group) /FL = gb: U35735.1 gb: NM_015865.1 | NM_015865 1 (DNA) 4 (protein) |

TABLE 42-continued

| Rank | Gene ID | Unigene ID archival/ current | AUC | Gene Symbol | Solubility | Gene Title | Description | GenBank SEQIDNO. |
|---|---|---|---|---|---|---|---|---|
| 39 | 1867 | Hs.234680 Hs.234680 | 0.8695 | FER1L3 | Semen | fer-1-like 3, myoferlin (*C. elegans*) | gb: NM_013451.1 /DEF = *Homo sapiens* fer-1 (*C. elegans*)-like 3 (myoferlin) (FER1L3), mRNA. /FEA = mRNA /GEN = FER1L3 /PROD = fer-1 (*C. elegans*)-like 3 (myoferlin) /DB_XREF = gi: 7305052 /UG = Hs.234680 fer-1 (*C. elegans*)-like 3 (myoferlin) /FL = gb: AF182316.1 gb: NM_013451.1 | NM_013451 2 (DNA) 5 (protein) |
| 64 | 1051 | Hs.118796 Hs.412117 | 0.862 | ANXA6 | Urine Semen Blood | annexin A6 | gb: NM_001155.2 /DEF = *Homo sapiens* annexin A6 (ANXA6), transcript variant 1, mRNA. /FEA = mRNA /GEN = ANXA6 /PROD = annexin VI isoform 1 /DB_XREF = gi: 4809274 /UG = Hs.118796 annexin A6 /FL = gb: J03578.1 gb: D00510.1 gb: NM_001155.2 | NM_001155 3 (DNA) 6 (protein) |

The preceding detailed description of the preferred embodiments disclosed methods for identification of biomarkers for prostate cancer using gene expression data from microarrays. RFE was used to identify a small number of biomarkers that should lead to the creation of inexpensive, accurate tests that may be used in conjunction with or in place of current diagnostic, prognostic and monitoring tests for prostate cancer by using gene expression or protein expression data. Preferred applications of the present invention will target proteins expressed by the identified genes that are detectable in serum or semen, thus providing non-invasive or minimally invasive screening for prostate cancer and monitoring of treatment.

Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

REFERENCES

Incorporated Herein by Reference

[1] Singh D, et al., Gene expression correlates of clinical prostate cancer behavior *Cancer Cell*, 2:203-9, Mar. 1, 2002.

[2] Febbo P., et al., Use of expression analysis to predict outcome after radical prostatectomy, *The Journal of Urology*, Vol. 170, pp. S11-S20, December 2003. Delineation of prognostic biomarkers in prostate cancer. Dhanasekaran S M, Barrette T R, Ghosh D, Shah R, Varambally S, Kurachi K, Pienta K J, Rubin M A, Chinnaiyan A M. Nature. 2001 Aug. 23; 412(6849):822-6.

[3] Comprehensive gene expression analysis of prostate cancer reveals distinct transcriptional programs associated with metastatic disease. LaTulippe E, Satagopan J, Smith A, Scher H, Scardino P, Reuter V, Gerald W L. Cancer Res. 2002 Aug. 1; 62(15):4499-506.

[4] Gene expression analysis of prostate cancers. Luo J H, Yu Y P, Cieply K, Lin F, Deflavia P, Dhir R, Finkelstein S, Michalopoulos G, Becich M. Mol Carcinog. 2002 January; 33(1):25-35

[5] Expression profiling reveals hepsin overexpression in prostate cancer. Magee J A, Araki T, Patil S, Ehrig T, True L, Humphrey P A, Catalona W J, Watson M A, Milbrandt J. Cancer Res. 2001 Aug. 1; 61(15):5692-6.

[6] Analysis of gene expression identifies candidate markers and pharmacological targets in prostate cancer. Welsh J B, Sapinoso L M, Su A I, Kern S G, Wang-Rodriguez J, Moskaluk C A, Frierson H F Jr, Hampton G M. Cancer Res. 2001 Aug. 15; 61(16):5974-8.

[7] Human prostate cancer and benign prostatic hyperplasia: molecular dissection by gene expression profiling. Luo J, Duggan D J, Chen Y, Sauvageot J, Ewing C M, Bittner M L, Trent J M, Isaacs W B. Cancer Res. 2001 Jun. 15; 61(12): 4683-8.

[8] A molecular signature of metastasis in primary solid tumors. Ramaswamy S, Ross K N, Lander E S, Golub T R. Nat Genet. 2003 January; 33(1):49-54. Epub 2002 Dec. 9.

[9] A compendium of gene expression in normal human tissues. Hsiao L L, Dangond F, Yoshida T, Hong R, Jensen R V, Misra J, Dillon W, Lee K F, Clark K E, Haverty P, Weng Z, Mutter G L, Frosch M P, Macdonald M E, Milford E L, Crum C P, Bueno R, Pratt R E, Mahadevappa M, Warrington J A, Stephanopoulos G, Stephanopoulos G, Gullans SR. Physiol Genomics. 2001 Dec. 21; 7(2):97-104.

[10] Molecular classification of human carcinomas by use of gene expression signatures. Su A I, Welsh J B, Sapinoso L M, Kern S G, Dimitrov P, Lapp H, Schultz P G, Powell S M, Moskaluk C A, Frierson H F Jr, Hampton GM. Cancer Res. 2001 Oct. 15; 61(20):7388-93.

[11] Gene expression analysis of prostate cancers. Jian-Hua Luo *, Yan Ping Yu, Kathleen Cieply, Fan Lin, Petrina Deflavia, Rajiv Dhir, Sydney Finkelstein, George Michalopoulos, Michael Becich.

[12] Transcriptional Programs Activated by Exposure of Human Prostate Cancer Cells to Androgen", Samuel E. DePrimo, Maximilian Diehn, Joel B. Nelson, Robert E.

Reiter, John Matese, Mike Fero, Robert Tibshirani, Patrick O. Brown, James D. Brooks. *Genome Biology*, 3(7) 2002

[13] A statistical method for identifying differential gene-gene co-expression patterns, Yinglei Lai, Baolin Wu, Liang Chen and Hongyu Zhao. *Bioinformatics vol*. 20 issue 17.

[14] Induction of the Cdk inhibitor p21 by LY83583 inhibits tumor cell proliferation in a p53-independent manner Dimitri Lodygin, Antje Menssen, and Heiko Hermeking, *J. Clin. Invest.* 110:1717-1727 (2002).

[15] Classification between normal and tumor tissues based on the pair-wise gene expression ratio. YeeLeng Yap, XueWu Zhang, M T Ling, XiangHong Wang, YC Wong, and Antoine Danchin BMC Cancer. 2004; 4: 72.

[16] Kishino H, Waddell P J. Correspondence analysis of genes and tissue types and finding genetic links from microarray data. Genome Inform Ser Workshop Genome Inform 2000; 11: 83-95.

[17] Proteomic analysis of cancer-cell mitochondria. Mukesh Verma, Jacob Kagan, David Sidransky & Sudhir Srivastava, *Nature Reviews Cancer* 3, 789-795 (2003);

[18] Changes in collagen metabolism in prostate cancer: a host response that may alter progression. Burns-Cox N, Avery N C, Gingell J C, Bailey A J. J. Urol. 2001 November; 166(5):1698-701.

[19] Differentiation of Human Prostate Cancer PC-3 Cells Induced by Inhibitors of Inosine 5'-Monophosphate Dehydrogenase. Daniel Floryk1, Sandra L. Tollaksen2, Carol S. Giometti2 and Eliezer Huberman1 Cancer Research 64, 9049-9056, Dec. 15, 2004.

[20] Epithelial Na, K-ATPase expression is down-regulated in canine prostate cancer; a possible consequence of metabolic transformation in the process of prostate malignancy Ali Mobasheri, Richard Fox, Iain Evans, Fay Cullingham, Pablo Martín-Vasallo and Christopher S Foster Cancer Cell International 2003, 3:8

What is claimed is:

1. A method for screening for the presence of prostate cancer in a patient comprising:
  detecting within a patient sample comprising prostate cells each polynucleotide of a combination of polynucleotides consisting of SLC14A1 (SEQ ID NO. 1), FER1L3 (SEQ ID NO. 2) and ANXA6 (SEQ ID NO. 3);
  comparing levels of the polynucleotides to a control sample comprising prostate cells taken from a control subject not having prostate cancer, wherein the patient sample and the control sample are of a same sample type;
  wherein decreased levels of each of the polynucleotides in the combination in the patient sample relative to the control sample are indicative of prostate cancer.

2. The method of claim 1, wherein the patient sample and the control sample each comprises serum containing prostate cells.

3. The method of claim 1, wherein the patient sample and the control sample each comprises semen containing prostate cells.

4. A method for screening for the presence of prostate cancer in a patient comprising:
  detecting within a patient sample containing prostate cells underexpression relative to a non-cancer control sample containing prostate cells of each polynucleotide of a combination of polynucleotides comprising SLC14A1 (SEQ ID NO. 1), FER1L3 (SEQ ID NO. 2) and ANXA6 (SEQ ID NO. 3), wherein the patient sample and the non-cancer control sample are of a same sample type.

5. The method of claim 4, wherein the patient sample and the non-cancer control sample each comprises serum.

6. The method of claim 4, wherein the patient sample and the non-cancer control sample each comprises semen.

* * * * *

SEQUENCE LISTING

```
<160> NUMBER OF SEQ ID NOS: 6

<210> SEQ ID NO 1
<211> LENGTH: 2722
<212> TYPE: DNA
<213> ORGANISM: Homo sapiens
<220> FEATURE:
<221> NAME/KEY: gene
<223> OTHER INFORMATION: Unigene: Hs.171731 (arch.); Hs.101307 (curr.)
      solute carrier family 14 (SLC14A1)
<300> PUBLICATION INFORMATION:
<308> DATABASE ACCESSION NUMBER: GenBank Accession: NM_015865
<309> DATABASE ENTRY DATE: 2006-11-17

<400> SEQUENCE: 1
agtaagcact ctcccttgtc gtggaggtgg gcaaatcttt atcagccact gccttctgct      60
gccaggaagc cagctagagt ggtctttaaa gaaaactggg catctcctgc tacttaaaat     120
caaaaactac ctaaaataaa gattatagag ccagaggaag agatagccat ggaggacagc     180
cccactatgg ttagagtgga cagccccact atggttaggg gtgaaaacca ggtttcgcca     240
tgtcaaggga gaaggtgctt ccccaaagct cttggctatg tcaccggtga catgaaagaa     300
cttgccaacc agcttaaaga caaacccgtg gtgctccagt tcattgactg gattctccgg     360
ggcatatccc aagtggtgtt cgtcaacaac cccgtcagtg gaatcctgat tctggtagga     420
cttcttgttc agaaccctg gtgggctctc actggctggc tgggaacagt ggtctccact     480
ctgatggccc tcttgctcag ccaggacagg tcattaatag catctgggct ctatggctac     540
aatgccaccc tggtgggagt actcatggct gtcttttcgg acaagggaga ctatttctgg     600
tggctgttac tccctgtatg tgctatgtcc atgacttgcc caatttttctc aagtgcattg     660 aattccatgc tcagcaaatg ggacctcccc gtcttcaccc tccctttcaa catggcgttg     720
tcaatgtacc tttcagccac aggacattac aatccgttct ttccagccaa actggtcata     780
cctataacta cagctccaaa tatctcctgg tctgacctca gtgccctgga gttgttgaaa     840
tctataccag tgggagttgg tcagatctat ggctgtgata atccatggac aggggcatt     900 ttcctgggag ccatcctact ctcctccca ctcatgtgcc tgcatgctgc cataggatca     960
ttgctgggca tagcagcggg actcagtctt tcagcccat ttgagaacat ctactttga    1020 ctctggggtt tcaacagctc tctggcctgc attgcaatgg gaggaatgtt catggcgctc    1080
acctggcaaa cccacctcct ggctcttggc tgtgccctgt tcacgcccta tctttggagtc    1140 ggcatggcaa actttatggc tgaggttgga ttgccagctt gtacctggcc cttctgtttg    1200
```

| | |
|---|---|
| gccacgctat tgttcctcat catgaccaca aaaaattcca acatctacaa gatgcccctc | 1260 |
| agtaaagtta cttatcctga agaaaaccgc atcttctacc tgcaagccaa gaaaagaatg | 1320 |
| gtggaaagcc ctttgtgaga acaagcccca tttgcagcca tggtcacgag tcatttctgc | 1380 |
| ctgactgctc cagctaactt ccagggtctc agcaaactgc tgttttcac gagtatcaac | 1440 |
| tttcatactg acgcgtctgt aatctgttct tatgctcatt ttgtatttc ctttcaactc | 1500 |
| caggaatatc cttgagcata tgagagtcac atccaggtga tgtgctctgg tatggaattt | 1560 |
| gaaaccccaa tggggccttg gcactaagac tggaatgtat ataaagtcaa agtgctccaa | 1620 |
| cagaaggagg aagtgaaaac aaactattag tatttattga tattcttggt gtttagctgg | 1680 |
| ctcgatgatg ttaacagtat taaaaattaa acccccataa acccaaccta agcctatgga | 1740 |
| atccacagtc acaaaatcga agttaaccca gaatctgtga taagcagctt ggcttttttt | 1800 |
| ttaaatcaat gcaagtacac cattatagcc agaatctgta tcacagaggt gcaagctgac | 1860 |
| agcagagctc agtccccact tcctgcaaac aatggcctgc accctatccc ttgtgtgtgt | 1920 |
| gacattctct catgggacaa tgttggggtt tttcagactg acaggactgc aagagggaga | 1980 |
| aaggaatttt gtcaatcaaa attattctgt attgcaactt ttctcagaga ttgcaaagga | 2040 |
| ttttttaggt agagattatt tttccttatg aaaaatgatc tgttttaaat gagataaaat | 2100 |
| aggagaagtt cctggcttaa cctgttctta catattaaag aaaagttact tactgtatt | 2160 |
| atgaaatact cagcttaggc attttacttt taacccctaa attgattttg taaatgccac | 2220 |
| aaatgcatag aattgttacc aacctccaaa gggctcttta aaatcatatt ttttattca | 2280 |
| tttgaggatg tcttataaag actgaaggca aaggtcagaa tgcttacggg tgttatttt | 2340 |
| ataagttgtt gaattcctta atttagaaaa gctcattatt ttttgcacac tcacaatatt | 2400 |
| ctctctcaga aatcaatggc atttgaacca ccaaaaagaa ataaagggct gagtgtggtg | 2460 |
| ctcacgcctg taatcccagc actttgggga gcccaggcgg gcagattgct tgaacccagg | 2520 |
| agttcaagac cagcctgggc agcatggtga aaccctgtat ctacaaaaaa tacaaaaatt | 2580 |
| agccaggcat ggtggtgggt gcctgtagtt ccagctactt gggaggctga ggtgggaaaa | 2640 |
| tgacttgagc ccaggaggag gaggctgcag tgagctaaga ttgcaccact gcactccaac | 2700 |
| ctgggtgaca agagtgaaac tg | 2722 |

```
<210> SEQ ID NO 2
<211> LENGTH: 6829
<212> TYPE: DNA
<213> ORGANISM: Homo sapiens
<220> FEATURE:
<223> OTHER INFORMATION: Unigene Hs.234680 (arch.); Hs.655728 (current)
      fer-1 (myoferlin)3 (FER1L3)
<300> PUBLICATION INFORMATION:
<308> DATABASE ACCESSION NUMBER: GenBank Accession:NM_013451
<309> DATABASE ENTRY DATE: 2002-03-26

<400> SEQUENCE: 2
```

| | |
|---|---|
| cttctctccc agggcggtgc gacccggagc tccagcgccc gagtctccac ttcgtttgct | 60 |
| gaaacttgct ttctaccagc taagaaccat gctgcgagtg attgtggaat ctgccagcaa | 120 |
| tatccctaaa acgaaatttg gcaagccgga tcctattgtt tctgtcattt ttaaggatga | 180 |
| gaaaagaaa acaaagaaag ttgataatga attgaaccct gtctgaatg agattttgga | 240 |
| gtttgacttg aggggtatac cactggactt tcatcttcc cttgggatta ttgtgaaaga | 300 |
| ttttgagaca attggacaaa ataaattaat tggcacggcg actgtagccc tgaaggacct | 360 |
| gactggtgac cagagcagat ccctgccgta caagctgatc tccctgctaa atgaaaaagg | 420 |

```
gcaagatact ggggccacca ttgacttggt gatcggctat gatccgcctt ctgctccaca      480
tccaaatgac ctgagcgggc ccagcgtgcc aggcatggga ggagatgggg aagaagatga      540
aggtgatgaa gacaggttgg acaatgcagt caggggccct gggcccaagg ggccagttgg      600
gacggtgtcg gaagctcagc ttgctcggag gctcaccaaa gtaaagaaca gccggcggat      660
gctgtcaaat aagccacagg acttccagat ccgcgtccga gtgattgagg ccgacagtt       720 aagtggtaac aacataaggc ctgtggtcaa agttcacgtc tgtggccaga cacaccgaac      780
aagaatcaag agaggaaaca acccttttt tgatgagttg tttttctaca atgtcaacat       840
gaccccttct gaattgatgg atgagatcat cagcatccgg gtttataatt ctcactctct      900
gcgggcagat tgtctgatgg gggaatttaa gattgatgtt ggatttgttt atgatgaacc      960
tggccatgct gtcatgagaa agtggcttct tctcaatgac ccggaagata ccagttcagg     1020
ttctaaaggt tatatgaaag tcagcatgtt tgtcctggga accggagatg agcctcctcc     1080
tgagagacga gatcgtgata atgacagtga tgatgtggag agtaatttgt tactccctgc     1140
tggcattgcc ctccggtggg tgaccttctt gctgaaaatc taccgagctg aggacatccc     1200
ccagatggat gatgccttct cacagacagt aaaggaaata tttggaggca atgcagataa     1260
gaaaaatctc gtggatcctt ttgtagaagt ttcctttgct ggaaaaaagg tttgtacaaa     1320
cataattgag aaaaatgcaa acccagagtg gaatcaggtc gtcaatcttc agatcaagtt     1380
tccttcagtg tgtgaaaaaa taaaactaac aatatatgac tgggaccgtc ttactaaaaa     1440
tgatgtagtt ggaacaacat atctacacct ctctaaaatt gctgcctctg gtggggaagt     1500
ggaagatttc tcatcttcgg gaactggggc tgcatcatat acagtaaaca caggagaaac     1560
agaggtaggc tttgttccaa cgtttggacc ttgttacctg aatctttatg gaagccccag     1620
ggagtacacg ggattcccag acccctatga tgagctgaat actggaaagg gggaaggagt     1680
tgcctacaga ggcaggatct tggttgaatt agccacttt cttgagaaga caccaccaga      1740
taaaaagctt gagcccattt caaatgatga cctgctggtt gttgagaaat accagcgaag     1800
gcggaagtac agcctgtctg ccgtgtttca ttcagccacc atgttgcaag atgttggtga     1860
ggccattcag tttgaagtca gcattgggaa ctatggcaac aagtttgaca ccacctgtaa     1920
gcctttggca tcaacaactc agtacagccg tgctgtattt gatggcaact actattata      1980 cttgccttgg gcccacacca agccagttgt taccctgact tcatactggg aggatattag     2040
tcatcgcctg gatgcggtga acactctcct agctatggca gaacggctgc aaacaaatat     2100
agaagctcta aaatcaggga tacaaggtaa aattcctgca aaccagctgg ctgaattgtg     2160
gctgaagctg atagatgaag ttatagaaga cacgagatac acgttgcctc tcacagaagg     2220
aaaagccaac gtcacagttc tcgatactca gatccgaaag ctgcggtcca ggtctctctc     2280
ccaaatacat gaggcggctg tgaggatgag gtcggaagcc acagatgtga agtccacact     2340
ggcagaaatt gaggactggc ttgataaatt aatgcagctg actgaagagc cacagaacag     2400
catgcctgac atcatcatct ggatgatccg gggagagaag agactggcct atgcacgaat     2460 tccgcacat caggtcttgt actccaccag tggtgagaat gcatctggaa atactgtgg      2520 gaaacccaa accatctttc tgaagtatcc acaggagaaa acaacgggc caaaggtgcc      2580 tgtggagttg cgagtgaaca tctggctagg cttaagtgct gtggagaaga gtttaacag     2640 cttcgcagaa ggaactttca ccgtctttgc tgaaatgtat gaaaatcaag ctctcatgtt     2700
tggaaaatgg ggtacttctg gattagtagg acgtcataag ttttctgatg tcacaggaaa     2760
aataaaactc aagagggaat tttttctgcc tccaaaaggc tgggaatggg aaggagagtg     2820
```

-continued

```
gatagttgat cctgaaagaa gcttgctgac tgaggcagat gcaggtcaca cggagttcac    2880
tgatgaagtc tatcagaacg agagccgcta ccccgggggc gactggaagc cggccgagga    2940 cacctcacacg gatgcgaacg gcgataaagc agcatcaccc agcgagttga cttgtcctcc    3000
aggttgggaa tgggaagatg atgcatggtc ttatgacata aatcgagcgg tggatgagaa    3060
aggctgggaa tatggaatca ccattcctcc tgatcataag cccaaatcct gggttgcagc    3120
agagaaaatg taccacactc atagacggcg aaggctggtc cgaaaacgca agaaagattt    3180
aacacagact gcttcaagca ccgcaagggc catggaggaa ttgcaagacc aagagggctg    3240
ggaatatgct tctctaattg gctggaaatt tcactggaaa caacgtagtt cagataccct    3300
ccgccgcaga cgctggagga gaaaaatggc tccttcagaa acacatggtg cagctgccat    3360 cttttaaactt gaaggtgccc ttggggcaga cactaccgaa gatggggatg agaagagcct    3420
ggagaaacag aagcacagtg ccaccactgt gttcggagca acaccccca ttgtttcctg    3480 caattttgac agagtctaca tctaccatct gcgctgctat gtctatcaag ccagaaacct    3540
cttggcttta gataaggata gcttttcaga tccatatgct catatctgtt cctccatcg    3600 gagcaaaacc actgagatca tccattcaac cctgaatccc acgtgggacc aaacaattat    3660
attcgatgaa gttgaaatct atggggaacc ccaaacagtt ctacagaatc acccaaagt    3720 tatcatgaac cttttgaca atgaccaagt gggcaaagat gaattttag gacgaagcat    3780 tttctctcct gtggtgaaac tgaactcaga aatggacatc acacccaaac ttctctggca    3840
cccagtaatg aatggagaca aagcctgcgg ggatgttctt gtaactgcag agctgattct    3900
gaggggcaag gatggctcca accttcccat tcttccccct caagggcgc caaatctata    3960 catggtcccc caggggatca ggcctgtggt ccagctcact gccattgaga ttctagcttg    4020
gggcttaaga aatatgaaaa acttccagat ggcttctatc acatcccca gtcttgttgt    4080 ggagtgtgga ggagaaaggg tggaatcggt ggtgatcaaa aaccttaaga agacacccaa    4140
ctttccaagt tctgttctct tcatgaaagt gttcttgccc aaggaggaat tgtacatgcc    4200
cccactggtg atcaaggtca tcgaccacag gcagtttggg cggaagcctg tcgtcggcca    4260
gtgcaccatc gagcgcctgg accgctttcg ctgtgaccct tatgcaggga agaggacat    4320 cgtcccacag ctcaaagcct cccttctgtc tgccccacca tgccgggaca tcgttatcga    4380
aatggaagac accaaaccat tactggcttc taagctgaca gaaaaggagg aagaaatcgt    4440
ggactggtgg agtaaatttt atgcttcctc aggggaacat gaaaaatgcg gacagtatat    4500
tcagaaaggc tattccaagc tcaagatata taattgtgaa ctagaaaatg tagcagaatt    4560
tgagggcctg acagacttct cagatacgtt caagttgtac cgaggcaagt cggatgaaaa    4620
tgaagatcct tctgtggttg gagagtttaa gggctccttt cggatctacc ctctgccgga    4680 tgacccccagc gtgccagccc ctcccagaca gtttcgggaa ttacctgaca gcgtcccaca    4740
ggaatgcacg gttaggattt acattgttcg aggcttagag ctccagcccc aggacaacaa    4800
tggcctgtgt gacccttaca taaaaataac actgggcaaa aaagtcattg aagaccgaga    4860
tcactacatt cccaacactc tcaacccagt ctttggcagg atgtacgaac tgagctgcta    4920
cttacctcaa gaaaaagacc tgaaaatttc tgtctatgat tatgacacct ttaccgggga    4980
tgaaaaagta ggagaaacaa ttattgatct ggaaaaccga ttcctttccc gctttgggtc    5040
ccactgcggc ataccagagg agtactgtgt ttctggagtc aatacctggc gagatcaact    5100
gagaccaaca cagctgcttc aaaatgtcgc cagattcaaa ggcttcccac aacccatcct    5160
ttccgaagat gggagtagaa tcagatatgg aggacgagac tacagcttgg atgaatttga    5220
```

| | |
|---|---|
| agccaacaaa atcctgcacc agcacctcgg ggcccctgaa gagcggcttg ctcttcacat | 5280 |
| cctcaggact caggggctgg tccctgagca cgtggaaaca aggactttgc acagcacctt | 5340 |
| ccagcccaac atttcccagg gaaaacttca gatgtgggtg gatgttttcc ccaagagttt | 5400 |
| ggggccacca ggccctcctt tcaacatcac accccggaaa gccaagaaat actacctgcg | 5460 |
| tgtgatcatc tggaacacca aggacgttat cttggacgag aaaagcatca caggagagga | 5520 |
| aatgagtgac atctacgtca aaggctggat tcctggcaat gaagaaaaca aacagaaaac | 5580 |
| agatgtccat tacagatctt tggatggtga agggaatttt aactggcgat tgtttttccc | 5640 |
| gtttgactac cttccagccg aacaactctg tatcgttgcg aaaaagagc atttctggag | 5700 |
| tattgaccaa acggaatttc gaatcccacc caggctgatc attcagatat gggacaatga | 5760 |
| caagttttct ctggatgact acttgggttt cctagaactt gacttgcgtc acacgatcat | 5820 |
| tcctgcaaaa tcaccagaga aatgcaggtt ggacatgatt ccggacctca agccatgaa | 5880 |
| ccccccttaaa gccaagacag cctccctctt tgagcagaag tccatgaaag gatggtggcc | 5940 |
| atgctacgca gagaaagatg gcgcccgcgt aatggctggg aaagtggaga tgacattgga | 6000 |
| aatcctcaac gagaaggagg ccgacgagag gccagccggg aaggggcggg acgaacccaa | 6060 |
| catgaacccc aagctggact accaaatcg accagaaacc tccttcctct ggttcaccaa | 6120 |
| cccatgcaag accatgaagt tcatcgtgtg gcgccgcttt aagtgggtca tcatcggctt | 6180 |
| gctgttcctg cttatcctgc tgctcttcgt ggccgtgctc ctctactctt tgccgaacta | 6240 |
| tttgtcaatg aagattgtaa agccaaatgt gtaacaaagg caaaggcttc atttcaagag | 6300 |
| tcatccagca atgagagaat cctgcctctg tagaccaaca tccagtgtga ttttgtgtct | 6360 |
| gagaccacac cccagtagca ggttacgcca tgtcaccgag ccccattgat tcccagaggg | 6420 |
| tcttagtcct ggaaagtcag gccaacaagc aacgtttgca tcatgttatc tcttaagtat | 6480 |
| taaaagttttt attttctaaa gtttaaatca tgttttttcaa aatatttttc aaggtggctg | 6540 |
| gttccattta aaatcatct ttttatatgt gtcttcggtt ctagacttca gcttttggaa | 6600 |
| attgctaaat agaattcaaa aatctctgca tcctgaggtg atatacttca tatttgtaat | 6660 |
| caactgaaag agctgtgcat tataaaatca gttagaatag ttagaacaat tcttatttat | 6720 |
| gcccacaacc attgctatat tttgtatgga tgtcataaaa gtctatttaa cctctgtaat | 6780 |
| gaaactaaat aaaaatgttt caccttttaaa aaaaaaaaa aaaaaaaaa | 6829 |

<210> SEQ ID NO 3
<211> LENGTH: 2915
<212> TYPE: DNA
<213> ORGANISM: Homo sapiens
<220> FEATURE:
<221> NAME/KEY: gene
<223> OTHER INFORMATION: Unigene: Hs.118796 (arch.); Hs.412117
      (curr.); annexin A6 (ANXA6)
<300> PUBLICATION INFORMATION:
<308> DATABASE ACCESSION NUMBER: GenBank Accession: NM_001155.2
<309> DATABASE ENTRY DATE: 1999-05-13

<400> SEQUENCE: 3

| | |
|---|---|
| ggctgtcctc ccggtccgcc ccgcgctgcg gttgctgctg ggctaacggg ctccgatcca | 60 |
| gcgagcgctg cgtcctcgag tccctgcgcc cgtgcgtccg tctgcgaccc gaggcctccg | 120 |
| ctgcgcgtgg attctgctgc gaaccggaga ccatggccaa accagcacag ggtgccaagt | 180 |
| accggggctc catccatgac ttcccaggct ttgaccccaa ccaggatgcc gaggctctgt | 240 |
| acactgccat gaagggcttt ggcagtgaca aggaggccat actggacata atcacctcac | 300 |

```
ggagcaacag gcagaggcag gaggtctgcc agagctacaa gtccctctac ggcaaggacc      360
tcattgctga tttaaagtat gaattgacgg gcaagtttga acggttgatt gtgggcctga      420
tgaggccacc tgcctattgt gatgccaaag aaattaaaga tgccatctcg ggcattggca      480
ctgatgagaa gtgcctcatt gagatcttgg cttcccggac caatgagcag atgcaccagc      540
tggtggcagc atacaaagat gcctacgagc gggacctgga ggctgacatc atcggcgaca      600
cctctggcca cttccagaag atgcttgtgg tcctgctcca gggaaccagg aggaggatg       660 acgtagtgag cgaggacctg gtacaacagg atgtccagga cctatacgag gcaggggaac      720
tgaaatgggg aacagatgaa gcccagttca tttacatctt gggaaatcgc agcaagcagc      780
atcttcggtt ggtgttcgat gagtatctga agaccacagg gaagccgatt gaagccagca      840
tccgagggga gctgtctggg gactttgaga agctaatgct ggccgtagtg aagtgtatcc      900
ggagcacccc ggaatatttt gctgaaaggc tcttcaaggc tatgaagggc ctggggactc      960
gggacaacac cctgatccgc atcatggtct cccgtagtga gttggacatg ctcgacattc     1020
gggagatctt ccggaccaag tatgagaagt ccctctacag catgatcaag aatgacacct     1080
ctggcgagta caagaagact ctgctgaagc tgtctggggg agatgatgat gctgctggcc     1140
agttcttccc ggaggcagcg caggtggcct atcagatgtg ggaacttagt gcagtggccc     1200
gagtagagct gaagggaact gtgcgcccag ccaatgactt caaccctgac gcagatgcca     1260
aagcgctgcg gaaagccatg aagggactcg ggactgacga agacacaatc atcgatatca     1320
tcacgcaccg cagcaatgtc cagcggcagc agatccggca gaccttcaag tctcactttg     1380
gccgggactt aatgactgac ctgaagtctg agatctctgg agacctggca aggctgattc     1440
tggggctcat gatgccaccg gcccattacg atgccaagca gttgaagaag gccatggagg     1500
gagccggcac agatgaaaag gctcttattg aaatcctggc cactcggacc aatgctgaaa     1560
tccgggccat caatgaggcc tataaggagg actatcacaa gtccctggag gatgctctga     1620
gctcagacac atctggccac ttcaggagga tcctcatttc tctggccacg gggcatcgtg     1680
aggagggagg agaaaacctg gaccaggcac gggaagatgc ccaggtggct gctgagatct     1740
tggaaatagc agacacacct agtggagaca aaacttcctt ggagacacgt ttcatgacga     1800
tcctgtgtac ccggagctat ccgcaccctcc ggagagtctt ccaggagttc atcaagatga     1860
ccaactatga cgtggagcac accatcaaga aggagatgtc tggggatgtc agggatgcat     1920
ttgtggccat tgttcaaagt gtcaagaaca agcctctctt ctttgccgac aaactttaca     1980
aatccatgaa gggtgctggc acagatgaga agactctgac caggatcatg gtatcccgca     2040
gtgagattga cctgctcaac atccggaggg aattcattga gaaatatgac aagtctctcc     2100
accaagccat tgagggtgac acctccggag acttcctgaa ggccttgctg gctctctgtg     2160
gtggtgagga ctagggccac agctttggcg ggcacttctg ccaagaaatg gttatcagca     2220
ccagccgcca tggccaagcc tgattgttcc agctccagag actaaggaag gggcaggggt     2280
ggggggaggg gttgggttgg gctcttatct tcagtggagc ttaggaaacg ctcccactcc     2340
cacgggccat cgagggccca gcacggctga gcggctgaaa aaccgtagcc atagatcctg     2400
tccacctcca ctcccctctg accctcaggc tttcccagct tcctcccctt gctacagcct     2460 ctgcccctggt ttgggctatg tcagatccaa aaacatcctg aacctctgtc tgtaaaatga     2520
gtagtgtctg tactttgaat gagggggttg gtggcagggg ccagttgaat gtgctgggcg     2580
gggtggtggg aaggatagta aatgtgctgg ggcaaactga caaatcttcc catccatttc     2640
accacccatc tccatccagg ccgcgctaga gtactggacc aggaatttgg atgcctgggt     2700
```

```
tcaaatctgc atctgccatg cacttgtttc tgaccttagg ccagccccct tccctccctg    2760
agtctctatt ttcttatcta caatgagaca gttggacaaa aaaatcttgg cttcccttct    2820
aacattaact tcctaaagta tgcctccgat tcattccctt gacactttt atttctaagg     2880 aagaaataaa aagagataca caaacacata aacac                               2915
```

<210> SEQ ID NO 4
<211> LENGTH: 389
<212> TYPE: PRT
<213> ORGANISM: Homo sapiens
<220> FEATURE:
<223> OTHER INFORMATION: solute carrier family 14(urea transporter), member 1 isoform 2
<300> PUBLICATION INFORMATION:
<308> DATABASE ACCESSION NUMBER: GenBank Accession: NP_056949
<309> DATABASE ENTRY DATE: 2006-11-17

<400> SEQUENCE: 4

```
Met Glu Asp Ser Pro Thr Met Val Arg Val Asp Ser Pro Thr Met Val
1               5                   10                  15

Arg Gly Glu Asn Gln Val Ser Pro Cys Gln Gly Arg Arg Cys Phe Pro
            20                  25                  30

Lys Ala Leu Gly Tyr Val Thr Gly Asp Met Lys Glu Leu Ala Asn Gln
        35                  40                  45

Leu Lys Asp Lys Pro Val Val Leu Gln Phe Ile Asp Trp Ile Leu Arg
    50                  55                  60

Gly Ile Ser Gln Val Val Phe Val Asn Asn Pro Val Ser Gly Ile Leu
65                  70                  75                  80

Ile Leu Val Gly Leu Leu Val Gln Asn Pro Trp Trp Ala Leu Thr Gly
                85                  90                  95

Trp Leu Gly Thr Val Val Ser Thr Leu Met Ala Leu Leu Leu Ser Gln
            100                 105                 110

Asp Arg Ser Leu Ile Ala Ser Gly Leu Tyr Gly Tyr Asn Ala Thr Leu
        115                 120                 125

Val Gly Val Leu Met Ala Val Phe Ser Asp Lys Gly Asp Tyr Phe Trp
    130                 135                 140

Trp Leu Leu Leu Pro Val Cys Ala Met Ser Met Thr Cys Pro Ile Phe
145                 150                 155                 160

Ser Ser Ala Leu Asn Ser Met Leu Ser Lys Trp Asp Leu Pro Val Phe
                165                 170                 175

Thr Leu Pro Phe Asn Met Ala Leu Ser Met Tyr Leu Ser Ala Thr Gly
            180                 185                 190

His Tyr Asn Pro Phe Phe Pro Ala Lys Leu Val Ile Pro Ile Thr Thr
        195                 200                 205

Ala Pro Asn Ile Ser Trp Ser Asp Leu Ser Ala Leu Glu Leu Leu Lys
    210                 215                 220

Ser Ile Pro Val Gly Val Gly Gln Ile Tyr Gly Cys Asp Asn Pro Trp
225                 230                 235                 240

Thr Gly Gly Ile Phe Leu Gly Ala Ile Leu Leu Ser Ser Pro Leu Met
                245                 250                 255

Cys Leu His Ala Ala Ile Gly Ser Leu Leu Gly Ile Ala Ala Gly Leu
            260                 265                 270

Ser Leu Ser Ala Pro Phe Glu Asn Ile Tyr Phe Gly Leu Trp Gly Phe
        275                 280                 285

Asn Ser Ser Leu Ala Cys Ile Ala Met Gly Gly Met Phe Met Ala Leu
    290                 295                 300

Thr Trp Gln Thr His Leu Leu Ala Leu Gly Cys Ala Leu Phe Thr Ala
```

```
                305                 310                 315                 320
Tyr Leu Gly Val Gly Met Ala Asn Phe Met Ala Glu Val Gly Leu Pro
                    325                 330                 335

Ala Cys Thr Trp Pro Phe Cys Leu Ala Thr Leu Leu Phe Leu Ile Met
                    340                 345                 350

Thr Thr Lys Asn Ser Asn Ile Tyr Lys Met Pro Leu Ser Lys Val Thr
                    355                 360                 365

Tyr Pro Glu Glu Asn Arg Ile Phe Tyr Leu Gln Ala Lys Lys Arg Met
                    370                 375                 380

Val Glu Ser Pro Leu
385

<210> SEQ ID NO 5
<211> LENGTH: 2061
<212> TYPE: PRT
<213> ORGANISM: Homo sapiens
<220> FEATURE:
<223> OTHER INFORMATION: myoferlin isoform a
<300> PUBLICATION INFORMATION:
<308> DATABASE ACCESSION NUMBER: GeneBank Ascession: NP_038479
<309> DATABASE ENTRY DATE: 2002-03-26

<400> SEQUENCE: 5

Met Leu Arg Val Ile Val Glu Ser Ala Ser Asn Ile Pro Lys Thr Lys
1               5                   10                  15

Phe Gly Lys Pro Asp Pro Ile Val Ser Val Ile Phe Lys Asp Glu Lys
                20                  25                  30

Lys Lys Thr Lys Lys Val Asp Asn Glu Leu Asn Pro Val Trp Asn Glu
            35                  40                  45

Ile Leu Glu Phe Asp Leu Arg Gly Ile Pro Leu Asp Phe Ser Ser Ser
        50                  55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
                100                 105                 110

Asp Thr Gly Ala Thr Ile Asp Leu Val Ile Gly Tyr Asp Pro Pro Ser
            115                 120                 125

Ala Pro His Pro Asn Asp Leu Ser Gly Pro Ser Val Pro Gly Met Gly
        130                 135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
                165                 170                 175

Gln Leu Ala Arg Arg Leu Thr Lys Val Lys Asn Ser Arg Arg Met Leu
                180                 185                 190

Ser Asn Lys Pro Gln Asp Phe Gln Ile Arg Val Arg Val Ile Glu Gly
            195                 200                 205

Arg Gln Leu Ser Gly Asn Asn Ile Arg Pro Val Val Lys Val His Val
        210                 215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
                260                 265                 270
```

```
Ala Asp Cys Leu Met Gly Glu Phe Lys Ile Asp Val Gly Phe Val Tyr
        275                 280                 285
Asp Glu Pro Gly His Ala Val Met Arg Lys Trp Leu Leu Leu Asn Asp
        290                 295                 300
Pro Glu Asp Thr Ser Ser Gly Ser Lys Gly Tyr Met Lys Val Ser Met
305                 310                 315                 320
Phe Val Leu Gly Thr Gly Asp Glu Pro Pro Glu Arg Arg Asp Arg
                325                 330                 335
Asp Asn Asp Ser Asp Asp Val Glu Ser Asn Leu Leu Leu Pro Ala Gly
                340                 345                 350
Ile Ala Leu Arg Trp Val Thr Phe Leu Leu Lys Ile Tyr Arg Ala Glu
        355                 360                 365
Asp Ile Pro Gln Met Asp Asp Ala Phe Ser Gln Thr Val Lys Glu Ile
        370                 375                 380
Phe Gly Gly Asn Ala Asp Lys Lys Asn Leu Val Asp Pro Phe Val Glu
385                 390                 395                 400
Val Ser Phe Ala Gly Lys Lys Val Cys Thr Asn Ile Ile Glu Lys Asn
                405                 410                 415
Ala Asn Pro Glu Trp Asn Gln Val Val Asn Leu Gln Ile Lys Phe Pro
        420                 425                 430
Ser Val Cys Glu Lys Ile Lys Leu Thr Ile Tyr Asp Trp Asp Arg Leu
        435                 440                 445
Thr Lys Asn Asp Val Val Gly Thr Thr Tyr Leu His Leu Ser Lys Ile
450                 455                 460
Ala Ala Ser Gly Gly Glu Val Glu Asp Phe Ser Ser Ser Gly Thr Gly
465                 470                 475                 480
Ala Ala Ser Tyr Thr Val Asn Thr Gly Glu Thr Glu Val Gly Phe Val
                485                 490                 495
Pro Thr Phe Gly Pro Cys Tyr Leu Asn Leu Tyr Gly Ser Pro Arg Glu
                500                 505                 510
Tyr Thr Gly Phe Pro Asp Pro Tyr Asp Glu Leu Asn Thr Gly Lys Gly
                515                 520                 525
Glu Gly Val Ala Tyr Arg Gly Arg Ile Leu Val Glu Leu Ala Thr Phe
        530                 535                 540
Leu Glu Lys Thr Pro Pro Asp Lys Lys Leu Glu Pro Ile Ser Asn Asp
545                 550                 555                 560
Asp Leu Leu Val Val Glu Lys Tyr Gln Arg Arg Lys Tyr Ser Leu
                565                 570                 575
Ser Ala Val Phe His Ser Ala Thr Met Leu Gln Asp Val Gly Glu Ala
                580                 585                 590
Ile Gln Phe Glu Val Ser Ile Gly Asn Tyr Gly Asn Lys Phe Asp Thr
        595                 600                 605
Thr Cys Lys Pro Leu Ala Ser Thr Thr Gln Tyr Ser Arg Ala Val Phe
        610                 615                 620
Asp Gly Asn Tyr Tyr Tyr Leu Pro Trp Ala His Thr Lys Pro Val
625                 630                 635                 640
Val Thr Leu Thr Ser Tyr Trp Glu Asp Ile Ser His Arg Leu Asp Ala
                645                 650                 655
Val Asn Thr Leu Leu Ala Met Ala Glu Arg Leu Gln Thr Asn Ile Glu
                660                 665                 670
Ala Leu Lys Ser Gly Ile Gln Gly Lys Ile Pro Ala Asn Gln Leu Ala
        675                 680                 685
Glu Leu Trp Leu Lys Leu Ile Asp Glu Val Ile Glu Asp Thr Arg Tyr
```

-continued

```
            690                 695                 700
Thr Leu Pro Leu Thr Glu Gly Lys Ala Asn Val Thr Val Leu Asp Thr
705                 710                 715                 720

Gln Ile Arg Lys Leu Arg Ser Arg Ser Leu Ser Gln Ile His Glu Ala
                725                 730                 735

Ala Val Arg Met Arg Ser Glu Ala Thr Asp Val Lys Ser Thr Leu Ala
                740                 745                 750

Glu Ile Glu Asp Trp Leu Asp Lys Leu Met Gln Leu Thr Glu Pro
                755                 760                 765

Gln Asn Ser Met Pro Asp Ile Ile Ile Trp Met Ile Arg Gly Glu Lys
770                 775                 780

Arg Leu Ala Tyr Ala Arg Ile Pro Ala His Gln Val Leu Tyr Ser Thr
785                 790                 795                 800

Ser Gly Glu Asn Ala Ser Gly Lys Tyr Cys Gly Lys Thr Gln Thr Ile
                805                 810                 815

Phe Leu Lys Tyr Pro Gln Glu Lys Asn Asn Gly Pro Lys Val Pro Val
                820                 825                 830

Glu Leu Arg Val Asn Ile Trp Leu Gly Leu Ser Ala Val Glu Lys Lys
                835                 840                 845

Phe Asn Ser Phe Ala Glu Gly Thr Phe Thr Val Phe Ala Glu Met Tyr
850                 855                 860

Glu Asn Gln Ala Leu Met Phe Gly Lys Trp Thr Ser Gly Leu Val
865                 870                 875                 880

Gly Arg His Lys Phe Ser Asp Val Thr Gly Lys Ile Lys Leu Lys Arg
                885                 890                 895

Glu Phe Phe Leu Pro Pro Lys Gly Trp Glu Trp Glu Gly Glu Trp Ile
                900                 905                 910

Val Asp Pro Glu Arg Ser Leu Leu Thr Glu Ala Asp Ala Gly His Thr
                915                 920                 925

Glu Phe Thr Asp Glu Val Tyr Gln Asn Glu Ser Arg Tyr Pro Gly Gly
                930                 935                 940

Asp Trp Lys Pro Ala Glu Asp Thr Tyr Thr Asp Ala Asn Gly Asp Lys
945                 950                 955                 960

Ala Ala Ser Pro Ser Glu Leu Thr Cys Pro Pro Gly Trp Glu Trp Glu
                965                 970                 975

Asp Asp Ala Trp Ser Tyr Asp Ile Asn Arg Ala Val Asp Glu Lys Gly
                980                 985                 990

Trp Glu Tyr Gly Ile Thr Ile Pro Pro Asp His Lys Pro Lys Ser Trp
                995                 1000                1005

Val Ala Ala Glu Lys Met Tyr His Thr His Arg Arg Arg Arg Leu Val
                1010                1015                1020

Arg Lys Arg Lys Lys Asp Leu Thr Gln Thr Ala Ser Ser Thr Ala Arg
1025                1030                1035                1040

Ala Met Glu Glu Leu Gln Asp Gln Glu Gly Trp Glu Tyr Ala Ser Leu
                1045                1050                1055

Ile Gly Trp Lys Phe His Trp Lys Gln Arg Ser Ser Asp Thr Phe Arg
                1060                1065                1070

Arg Arg Arg Trp Arg Arg Lys Met Ala Pro Ser Glu Thr His Gly Ala
                1075                1080                1085

Ala Ala Ile Phe Lys Leu Glu Gly Ala Leu Gly Ala Asp Thr Thr Glu
                1090                1095                1100

Asp Gly Asp Glu Lys Ser Leu Glu Lys Gln Lys His Ser Ala Thr Thr
1105                1110                1115                1120
```

-continued

```
Val Phe Gly Ala Asn Thr Pro Ile Val Ser Cys Asn Phe Asp Arg Val
            1125                1130                1135

Tyr Ile Tyr His Leu Arg Cys Tyr Val Tyr Gln Ala Arg Asn Leu Leu
        1140                1145                1150

Ala Leu Asp Lys Asp Ser Phe Ser Asp Pro Tyr Ala His Ile Cys Phe
        1155                1160                1165

Leu His Arg Ser Lys Thr Thr Glu Ile Ile His Ser Thr Leu Asn Pro
        1170                1175                1180

Thr Trp Asp Gln Thr Ile Ile Phe Asp Glu Val Glu Ile Tyr Gly Glu
1185                1190                1195                1200

Pro Gln Thr Val Leu Gln Asn Pro Pro Lys Val Ile Met Glu Leu Phe
            1205                1210                1215

Asp Asn Asp Gln Val Gly Lys Asp Glu Phe Leu Gly Arg Ser Ile Phe
            1220                1225                1230

Ser Pro Val Val Lys Leu Asn Ser Glu Met Asp Ile Thr Pro Lys Leu
            1235                1240                1245

Leu Trp His Pro Val Met Asn Gly Asp Lys Ala Cys Gly Asp Val Leu
        1250                1255                1260

Val Thr Ala Glu Leu Ile Leu Arg Gly Lys Asp Gly Ser Asn Leu Pro
1265                1270                1275                1280

Ile Leu Pro Pro Gln Arg Ala Pro Asn Leu Tyr Met Val Pro Gln Gly
            1285                1290                1295

Ile Arg Pro Val Val Gln Leu Thr Ala Ile Glu Ile Leu Ala Trp Gly
            1300                1305                1310

Leu Arg Asn Met Lys Asn Phe Gln Met Ala Ser Ile Thr Ser Pro Ser
        1315                1320                1325

Leu Val Val Glu Cys Gly Gly Glu Arg Val Glu Ser Val Val Ile Lys
        1330                1335                1340

Asn Leu Lys Lys Thr Pro Asn Phe Pro Ser Ser Val Leu Phe Met Lys
1345                1350                1355                1360

Val Phe Leu Pro Lys Glu Glu Leu Tyr Met Pro Pro Leu Val Ile Lys
            1365                1370                1375

Val Ile Asp His Arg Gln Phe Gly Arg Lys Pro Val Val Gly Gln Cys
        1380                1385                1390

Thr Ile Glu Arg Leu Asp Arg Phe Arg Cys Asp Pro Tyr Ala Gly Lys
        1395                1400                1405

Glu Asp Ile Val Pro Gln Leu Lys Ala Ser Leu Leu Ser Ala Pro Pro
        1410                1415                1420

Cys Arg Asp Ile Val Ile Glu Met Glu Asp Thr Lys Pro Leu Leu Ala
1425                1430                1435                1440

Ser Lys Leu Thr Glu Lys Glu Glu Ile Val Asp Trp Trp Ser Lys
            1445                1450                1455

Phe Tyr Ala Ser Ser Gly Glu His Glu Lys Cys Gly Gln Tyr Ile Gln
        1460                1465                1470

Lys Gly Tyr Ser Lys Leu Lys Ile Tyr Asn Cys Glu Leu Glu Asn Val
        1475                1480                1485

Ala Glu Phe Glu Gly Leu Thr Asp Phe Ser Asp Thr Phe Lys Leu Tyr
        1490                1495                1500

Arg Gly Lys Ser Asp Glu Asn Glu Asp Pro Ser Val Val Gly Glu Phe
1505                1510                1515                1520

Lys Gly Ser Phe Arg Ile Tyr Pro Leu Pro Asp Asp Pro Ser Val Pro
            1525                1530                1535

Ala Pro Pro Arg Gln Phe Arg Glu Leu Pro Asp Ser Val Pro Gln Glu
            1540                1545                1550
```

Cys Thr Val Arg Ile Tyr Ile Val Arg Gly Leu Glu Leu Gln Pro Gln
        1555                1560                1565

Asp Asn Asn Gly Leu Cys Asp Pro Tyr Ile Lys Ile Thr Leu Gly Lys
        1570                1575                1580

Lys Val Ile Glu Asp Arg Asp His Tyr Ile Pro Asn Thr Leu Asn Pro
1585                1590                1595                1600

Val Phe Gly Arg Met Tyr Glu Leu Ser Cys Tyr Leu Pro Gln Glu Lys
            1605                1610                1615

Asp Leu Lys Ile Ser Val Tyr Asp Tyr Asp Thr Phe Thr Arg Asp Glu
        1620                1625                1630

Lys Val Gly Glu Thr Ile Ile Asp Leu Glu Asn Arg Phe Leu Ser Arg
        1635                1640                1645

Phe Gly Ser His Cys Gly Ile Pro Glu Glu Tyr Cys Val Ser Gly Val
        1650                1655                1660

Asn Thr Trp Arg Asp Gln Leu Arg Pro Thr Gln Leu Leu Gln Asn Val
1665                1670                1675                1680

Ala Arg Phe Lys Gly Phe Pro Gln Pro Ile Leu Ser Glu Asp Gly Ser
            1685                1690                1695

Arg Ile Arg Tyr Gly Gly Arg Asp Tyr Ser Leu Asp Glu Phe Glu Ala
        1700                1705                1710

Asn Lys Ile Leu His Gln His Leu Gly Ala Pro Glu Glu Arg Leu Ala
        1715                1720                1725

Leu His Ile Leu Arg Thr Gln Gly Leu Val Pro Glu His Val Glu Thr
        1730                1735                1740

Arg Thr Leu His Ser Thr Phe Gln Pro Asn Ile Ser Gln Gly Lys Leu
1745                1750                1755                1760

Gln Met Trp Val Asp Val Phe Pro Lys Ser Leu Gly Pro Pro Gly Pro
            1765                1770                1775

Pro Phe Asn Ile Thr Pro Arg Lys Ala Lys Lys Tyr Tyr Leu Arg Val
            1780                1785                1790

Ile Ile Trp Asn Thr Lys Asp Val Ile Leu Asp Glu Lys Ser Ile Thr
        1795                1800                1805

Gly Glu Glu Met Ser Asp Ile Tyr Val Lys Gly Trp Ile Pro Gly Asn
        1810                1815                1820

Glu Glu Asn Lys Gln Lys Thr Asp Val His Tyr Arg Ser Leu Asp Gly
1825                1830                1835                1840

Glu Gly Asn Phe Asn Trp Arg Phe Val Phe Pro Phe Asp Tyr Leu Pro
            1845                1850                1855

Ala Glu Gln Leu Cys Ile Val Ala Lys Lys Glu His Phe Trp Ser Ile
        1860                1865                1870

Asp Gln Thr Glu Phe Arg Ile Pro Pro Arg Leu Ile Ile Gln Ile Trp
        1875                1880                1885

Asp Asn Asp Lys Phe Ser Leu Asp Asp Tyr Leu Gly Phe Leu Glu Leu
1890                1895                1900

Asp Leu Arg His Thr Ile Ile Pro Ala Lys Ser Pro Glu Lys Cys Arg
1905                1910                1915                1920

Leu Asp Met Ile Pro Asp Leu Lys Ala Met Asn Pro Leu Lys Ala Lys
            1925                1930                1935

Thr Ala Ser Leu Phe Glu Gln Lys Ser Met Lys Gly Trp Trp Pro Cys
            1940                1945                1950

Tyr Ala Glu Lys Asp Gly Ala Arg Val Met Ala Gly Lys Val Glu Met
        1955                1960                1965

Thr Leu Glu Ile Leu Asn Glu Lys Glu Ala Asp Glu Arg Pro Ala Gly

```
                   1970              1975              1980
Lys Gly Arg Asp Glu Pro Asn Met Asn Pro Lys Leu Asp Leu Pro Asn
1985                1990              1995              2000

Arg Pro Glu Thr Ser Phe Leu Trp Phe Thr Asn Pro Cys Lys Thr Met
              2005              2010              2015

Phe Ile Val Trp Arg Lys Arg Phe Lys Trp Val Ile Ile Gly Leu Leu
              2020              2025              2030

Phe Leu Leu Ile Leu Leu Leu Phe Val Ala Val Leu Leu Tyr Ser Leu
              2035              2040              2045

Pro Asn Tyr Leu Ser Met Lys Ile Val Lys Pro Asn Val
              2050              2055              2060

<210> SEQ ID NO 6
<211> LENGTH: 673
<212> TYPE: PRT
<213> ORGANISM: Homo sapiens
<220> FEATURE:
<223> OTHER INFORMATION: annexin VI isoform 1
<300> PUBLICATION INFORMATION:
<308> DATABASE ACCESSION NUMBER: GeneBank Ascession: NP_001146
<309> DATABASE ENTRY DATE: 1999-05-13

<400> SEQUENCE: 6

Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
                20                  25                  30

Met Lys Gly Phe Gly Ser Asp Lys Glu Ala Ile Leu Asp Ile Ile Thr
            35                  40                  45

Ser Arg Ser Asn Arg Gln Arg Gln Glu Val Cys Gln Ser Tyr Lys Ser
50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
                100                 105                 110

Lys Cys Leu Ile Glu Ile Leu Ala Ser Arg Thr Asn Glu Gln Met His
            115                 120                 125

Gln Leu Val Ala Ala Tyr Lys Asp Ala Tyr Glu Arg Asp Leu Glu Ala
130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175

Val Gln Gln Asp Val Gln Asp Leu Tyr Glu Ala Gly Glu Leu Lys Trp
                180                 185                 190

Gly Thr Asp Glu Ala Gln Phe Ile Tyr Ile Leu Gly Asn Arg Ser Lys
            195                 200                 205

Gln His Leu Arg Leu Val Phe Asp Glu Tyr Leu Lys Thr Thr Gly Lys
210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
                260                 265                 270
```

-continued

```
Thr Leu Ile Arg Ile Met Val Ser Arg Ser Glu Leu Asp Met Leu Asp
        275                 280                 285
Ile Arg Glu Ile Phe Arg Thr Lys Tyr Glu Lys Ser Leu Tyr Ser Met
        290                 295                 300
Ile Lys Asn Asp Thr Ser Gly Glu Tyr Lys Lys Thr Leu Leu Lys Leu
305                 310                 315                 320
Ser Gly Gly Asp Asp Ala Ala Gly Gln Phe Phe Pro Glu Ala Ala
                325                 330                 335
Gln Val Ala Tyr Gln Met Trp Glu Leu Ser Ala Val Ala Arg Val Glu
                340                 345                 350
Leu Lys Gly Thr Val Arg Pro Ala Asn Asp Phe Asn Pro Asp Ala Asp
            355                 360                 365
Ala Lys Ala Leu Arg Lys Ala Met Lys Gly Leu Gly Thr Asp Glu Asp
        370                 375                 380
Thr Ile Ile Asp Ile Ile Thr His Arg Ser Asn Val Gln Arg Gln Gln
385                 390                 395                 400
Ile Arg Gln Thr Phe Lys Ser His Phe Gly Arg Asp Leu Met Thr Asp
            405                 410                 415
Leu Lys Ser Glu Ile Ser Gly Asp Leu Ala Arg Leu Ile Leu Gly Leu
        420                 425                 430
Met Met Pro Pro Ala His Tyr Asp Ala Lys Gln Leu Lys Lys Ala Met
        435                 440                 445
Glu Gly Ala Gly Thr Asp Glu Lys Ala Leu Ile Glu Ile Leu Ala Thr
        450                 455                 460
Arg Thr Asn Ala Glu Ile Arg Ala Ile Asn Glu Ala Tyr Lys Glu Asp
465                 470                 475                 480
Tyr His Lys Ser Leu Glu Asp Ala Leu Ser Ser Asp Thr Ser Gly His
                485                 490                 495
Phe Arg Arg Ile Leu Ile Ser Leu Ala Thr Gly His Arg Glu Glu Gly
            500                 505                 510
Gly Glu Asn Leu Asp Gln Ala Arg Glu Asp Ala Gln Val Ala Ala Glu
        515                 520                 525
Ile Leu Glu Ile Ala Asp Thr Pro Ser Gly Asp Lys Thr Ser Leu Glu
        530                 535                 540
Thr Arg Phe Met Thr Ile Leu Cys Thr Arg Ser Tyr Pro His Leu Arg
545                 550                 555                 560
Arg Val Phe Gln Glu Phe Ile Lys Met Thr Asn Tyr Asp Val Glu His
                565                 570                 575
Thr Ile Lys Lys Glu Met Ser Gly Asp Val Arg Asp Ala Phe Val Ala
            580                 585                 590
Ile Val Gln Ser Val Lys Asn Lys Pro Leu Phe Phe Ala Asp Lys Leu
        595                 600                 605
Tyr Lys Ser Met Lys Gly Ala Gly Thr Asp Glu Lys Thr Leu Thr Arg
        610                 615                 620
Ile Met Val Ser Arg Ser Glu Ile Asp Leu Leu Asn Ile Arg Arg Glu
625                 630                 635                 640
Phe Ile Glu Lys Tyr Asp Lys Ser Leu His Gln Ala Ile Glu Gly Asp
            645                 650                 655
Thr Ser Gly Asp Phe Leu Lys Ala Leu Leu Ala Leu Cys Gly Gly Glu
        660                 665                 670
Asp
```